(12) United States Patent
Li et al.

(10) Patent No.: US 10,919,869 B2
(45) Date of Patent: Feb. 16, 2021

(54) THIAZOLE DERIVATIVE AND APPLICATIONS

(71) Applicant: EAST CHINA UNIVERSITY OF SCIENCE AND TECHNOLOGY, Shanghai (CN)

(72) Inventors: Honglin Li, Shanghai (CN); Yufang Xu, Shanghai (CN); Rui Wang, Shanghai (CN); Zhenjiang Zhao, Shanghai (CN); Wenlin Song, Shanghai (CN); Liuxin Xu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 16/302,564

(22) PCT Filed: May 17, 2017

(86) PCT No.: PCT/CN2017/084748
§ 371 (c)(1),
(2) Date: Nov. 16, 2018

(87) PCT Pub. No.: WO2017/198178
PCT Pub. Date: Nov. 23, 2017

(65) Prior Publication Data
US 2019/0292162 A1 Sep. 26, 2019

(30) Foreign Application Priority Data
May 17, 2016 (CN) .......................... 2016 1 0327056

(51) Int. Cl.
| C07D 277/50 | (2006.01) |
| A61P 19/02 | (2006.01) |
| A61P 37/00 | (2006.01) |
| A61P 33/00 | (2006.01) |
| A61K 31/426 | (2006.01) |
| A61P 35/00 | (2006.01) |
| A61P 17/06 | (2006.01) |
| A61P 31/04 | (2006.01) |

(52) U.S. Cl.
CPC .......... *C07D 277/50* (2013.01); *A61K 31/426* (2013.01); *A61P 17/06* (2018.01); *A61P 19/02* (2018.01); *A61P 31/04* (2018.01); *A61P 33/00* (2018.01); *A61P 35/00* (2018.01); *A61P 37/00* (2018.01)

(58) Field of Classification Search
CPC .................................................. C07D 277/50
See application file for complete search history.

(56) References Cited

U.S. PATENT DOCUMENTS 4,319,026 A * 3/1982 Hedrich ................. A01N 43/74
504/179
2012/0208855 A1 8/2012 McLean et al.

FOREIGN PATENT DOCUMENTS

| CN | 103006653 A | 4/2013 |
| WO | 2013/056684 A2 | 4/2013 |
| WO | 2013/056684 A3 | 4/2013 |
| WO | 2013075596 A1 | 5/2013 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
English Translation of the International Search Report corresponding to PCT/CN2017/084748 dated Aug. 10, 2017, 3 pages.
CAS STN Registry, RN49038-11-0 (Feb 2, 2003); 1 page.
Li, Shiliang et al., "Rational Design of Benzylidenehydrazinyl-Substituted Thiazole Derivatives as Potent Inhibitors of human Dihydroorotate Dehydrogenease with in Vivo Anti-arthritic Activity," *Scientific Reports* (Oct. 7, 2015); 5(14836):1-19.
Extended European Search Report corresponding to EP 17798741.9 dated Oct. 14, 2019; 10 pages.
Database Registry, Chemical Abstracts Service, Columbus, Ohio Apr. 3, 2008, XP002794554 Database accession No. 1011908-75-0 *abstract* (1 page).
Song, Wenlin et al., "Structure-based design of potent human dihydroorotate dehydrogenase inhibitors as anticancer agents," *Med. Chem. Commun.* (Jun. 13, 2016) 7(7):1441-1448.

* cited by examiner

*Primary Examiner* — Shawquia Jackson
(74) *Attorney, Agent, or Firm* — Mintz Levin Cohn Ferris Glovsky and Popeo PC

(57) ABSTRACT

A thiazole derivative serving as a DHODH inhibitor, and applications thereof. The present invention specifically relates to a compound represented by formula I, a pharmaceutical composition containing the compound represented by formula (I), and applications of the compound in the preparation of drugs for treating diseases mediated by the DHODH or drugs for inhibiting the DHODH.

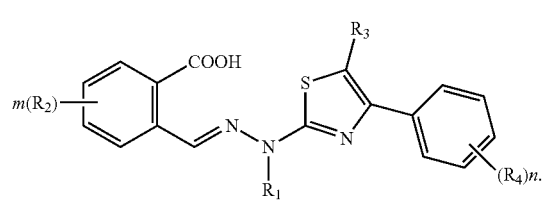

3 Claims, 1 Drawing Sheet

THIAZOLE DERIVATIVE AND APPLICATIONS

TECHNICAL FIELD

The present invention relates to the field of medicinal chemistry. In particular, the present invention relates to a novel thiazole derivative and a synthesis method thereof as well as its use as a dihydroorotate dehydrogenase (DHODH) inhibitor for treating DHODH-mediated diseases.

BACKGROUND

Dihydroorotate dehydrogenase (DHODH) is an iron-containing flavin-dependent mitochondrial enzyme, which is a key enzyme in the synthesis of pyrimidines in nucleic acids and catalyzes the fourth step-limiting reaction in the de novo biosynthetic pathway of pyrimidine. There are two ways to obtain pyrimidine nucleotides in humans, de novo synthesis and salvage synthesis. The resting lymphocytes in a human body mainly obtain pyrimidine nucleotides required for cell metabolism through the salvage synthesis pathway. However, under the immune activation state, the requirements of lymphocytes for pyrimidine nucleotides can reach 8 times or higher that those of resting lymphocytes. At this time, de novo synthesis pathway has to be initiated to supplement pyrimidine nucleotides, thereby achieving the proliferation of lymphocytes and completion of various immune functions. Therefore, de novo synthesis pathway of pyrimidine can be inhibited by inhibiting DHODH, thereby blocking the synthesis of neo-pyrimidine, causing disorders in DNA synthesis and inhibiting rapidly proliferation of human cells, such as, activated T-lymphocytes, B-lymphocytes, and tumor cells. Thus, dihydroorotate dehydrogenase (DHODH) inhibitors can be successfully developed into medicaments against rheumatic arthritis, tumor, organ transplant rejection, autoimmune diseases, such as psoriasis.

There are two main types of DHODH from different organisms: type I and type II. Type I DHODH is present in prokaryotes and in cells. These enzymes use some water-soluble molecules (such as fumaric acid and NAD+) as electron transporters in redox process; and type II DHODH is mainly located on mitochondrial inner membrane of mammals and some protozoa, and such enzymes utilize Flavin Mononucleotide (FMN) and Co-enzyme Q (CoQ, also known as ubiquinone) as electron transporters. Significantly different from type I DHODH, type II DHODH has a highly variable N-terminal extension for assisting binding of the enzyme to mitochondrial membrane, and the N-terminus forms a separate double α helix structure, thereby providing a binding site for steroids. Both human DHODH (hDHODH) and *Plasmodium falciparum* DHODH (Pf DHODH) belong to type II mitochondria-associated enzymes.

Kinetic studies have shown that the conversion of DHO (dihydroorotate) to OA (orotic acid) is a continuous "ping-pong" mechanism. The process is mainly accomplished by two half-reactions: firstly, dihydroorotate is oxidized to orotic acid under the catalysis of dihydroorotate dehydrogenase, and FMN accepts the hydrogen atom removed in the process and is oxidized to FMNH2. This half-reaction is the rate-limiting step of the catalytic reaction. Afterwards, FMNH2 is de-hydrogenated under the action of CoQ, re-reduced to FMN and returned to the cycle, as shown in the following reaction formula.

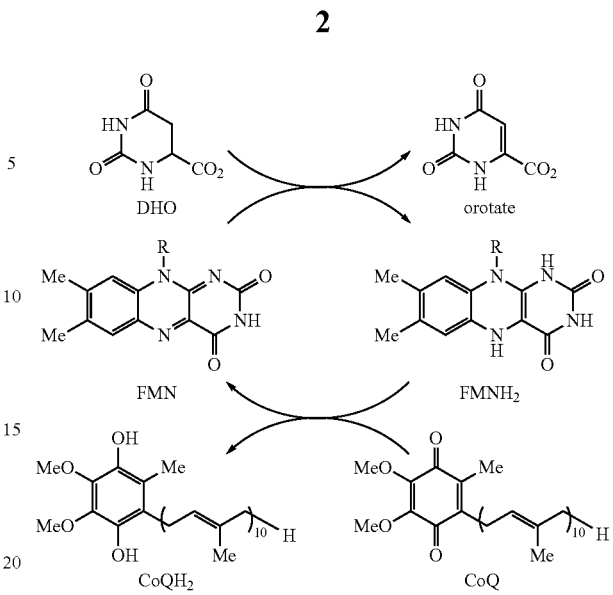

DHODH inhibitors can effectively reduce activities and numbers of immune-activated T-lymphocytes and B-lymphocytes, and can be successfully developed into a therapeutic medicament against tumors and autoimmune diseases, such as rheumatoid arthritis. At present, typical marketed DHODH inhibitors are mainly leflunomide, teriflunomide (A771726) and brequinar, the structural formulas of which are shown below.

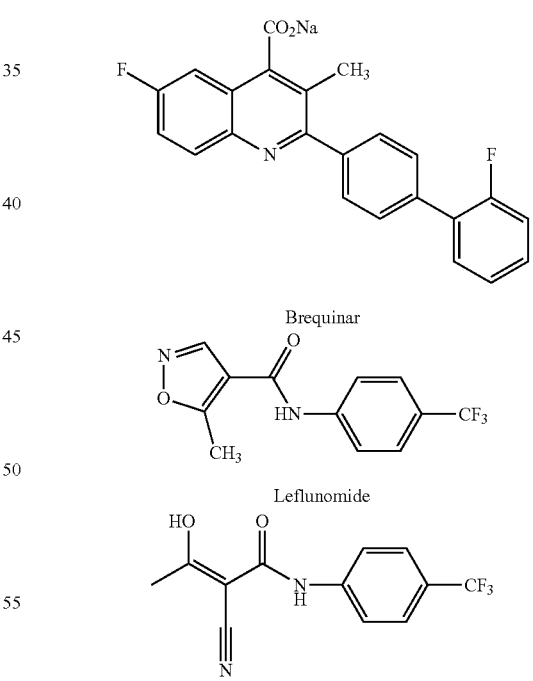

Leflunomide marketed in 1998 is an efficient inhibitor of DHODH, which blocks the cell signaling process by blocking the de novo synthesis pathway of pyrimidine and inhibiting the activity of tyrosine kinase. It is a novel isoxazole derivative with anti-inflammatory and immunosuppressive effects. It has been clinically used to treat rheumatoid arthritis, lupus erythematosus, multiple primary and secondary glomerular diseases, and to prevent graft rejection.

However, long-term use of Leflunomide can cause large side effects such as diarrhea, liver enzyme abnormalities, and rash due to its long half-life. Triflurane is an effective metabolite of Leflunomide. Brequinar has also entered Phase II clinical trials, but is limited by its narrow therapeutic window, and the clinical trials of Brequinar have found that when Brequinar is orally administered in combination with cyclosporine A or cisplatin, mucositis, white blood cell loss and thrombocytopenia may be caused.

Therefore, there is an urgent need in the art to find novel DHODH inhibitors, which are more efficient, safer and have better pharmacological properties.

SUMMARY OF THE INVENTION

It is an object of the present invention to provide a compound having a novel structure, high DHODH inhibitory activity, low toxicity, and good safety.

In a first aspect, a compound of formula I or a pharmaceutically acceptable salt or ester thereof is provided in the invention:

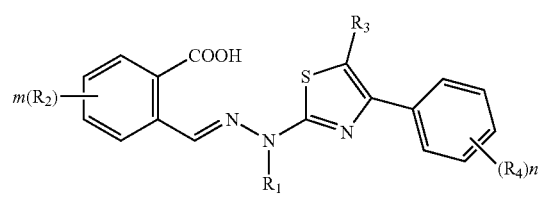

Wherein, $R_1$ is selected from the group consisting of: H, a substituted or unsubstituted $C_1$-$C_6$ alkyl, C3-C6 cycloalkyl;

$R_2$ is selected from the group consisting of: H, halogen, a substituted or unsubstituted C1-C6 alkyl, substituted or unsubstituted C1-C6 alkoxy, CN, $NO_2$, hydroxy, $NR^aR^b$;

$R^a$, $R^b$ are independently selected from H or C1-C6 alkyl;

$R_3$ is selected from the group consisting of H and a substituted or unsubstituted C1-C6 alkyl;

$R_4$ is selected from the group consisting of H and halogen;

m is an integer from 0 to 4;

n is an integer from 0 to 5;

wherein, when $R_2$ is H and $R_3$ is H, $R_1$ is not H.

In a specific embodiment, the compound is shown in Formula II:

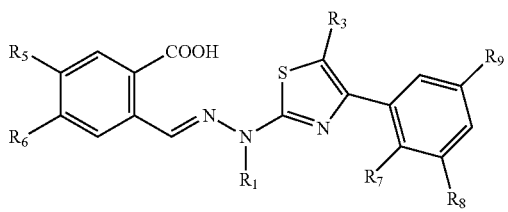

Wherein, $R_5$ and $R_6$ are independently selected from the group consisting of H, halogen, a substituted or unsubstituted C1-C6 alkyl, substituted or unsubstituted C1-C6 alkoxy, hydroxyl and $NH_2$;

$R_7$, $R_8$ and $R_9$ are independently selected from the group consisting of H and halogen;

$R_1$ and $R_3$ are as described above.

In a specific embodiment, $R_1$ is selected from a C1-C6 alkyl (preferably C1-C3 alkyl); $R_3$ is selected from H or a substituted or unsubstituted C1-C6 alkyl (preferably C1-C3 alkyl); $R_5$ and $R_6$ are independently selected from the group consisting of H, halogen (preferably F) and an unsubstituted or halogen (preferably F)-substituted C1-C3 alkyl; $R_7$ and $R_8$ are independently selected from the group consisting of H and halogen (preferably CO; and $R_9$ is H.

In a specific embodiment, $R_1$ is selected from the group consisting of: H, a C1-C6 alkyl, preferably C1-C3 alkyl; $R_3$ is selected from the group consisting of: H, a substituted or unsubstituted C1-C6 alkyl (preferably C1-C3 alkyl); $R_5$ is selected from the group consisting of: H, halogen (preferably F), an unsubstituted or halogen (preferably F)-substituted C1-C3 alkyl; $R_6$ is selected from the group consisting of: H, halogen (preferably F), hydroxyl, $NH_2$; $R_7$ and $R_8$ are independently selected from the group consisting of: H and halogen (preferably Cl); and $R_9$ is H.

In a second aspect, a compound or a pharmaceutically acceptable salt or ester thereof selected from the following group is provided in the invention:

| No. | Structure |
|-----|-----------|
| 1 | ![structure 1] |
| 2 | ![structure 2] |
| 3 | ![structure 3] |
| 4 | ![structure 4] |
| 5 | ![structure 5] |
| 6 | ![structure 6] |

-continued

| No. | Structure |
|---|---|
| 7 | 2-(COOH)C6H4-CH=N-N(CH2CH2OH)-thiazole-4-(2-Cl-C6H4) |
| 8 | 5-CF3-2-(COOH)C6H3-CH=N-N(CH3)-thiazole-4-(2-Cl-C6H4) |
| 8-1 | 5-CF3-2-(COOH)C6H3-CH=N-NH-thiazole-4-(2-Cl-C6H4) |
| 9 | 4-CH3-2-(COOH)C6H3-CH=N-N(CH3)-thiazole-4-(2-Cl-C6H4) |
| 9-1 | 4-CH3-2-(COOH)C6H3-CH=N-NH-thiazole-4-(2-Cl-C6H4) |
| 10 | 4-F-2-(COOH)C6H3-CH=N-N(CH3)-thiazole-4-(2-Cl-C6H4) |
| 10-1 | 4-F-2-(COOH)C6H3-CH=N-NH-thiazole-4-(2-Cl-C6H4) |
| 11 | 4-CH3-2-(COOH)C6H3-CH=N-N(CH3)-(4-methyl-5-phenylthiazol-2-yl) |
| 12 | 2-(COOH)C6H4-CH=N-N(CH3)-(4-methyl-5-phenylthiazol-2-yl) |
| 12-1 | 2-(COOH)C6H4-CH=N-NH-(4-methyl-5-phenylthiazol-2-yl) |
| 13 | 2-(COOH)C6H4-CH=N-N(CH3)-thiazole-4-methyl-5-(2-Cl-C6H4) |
| 14 | 2-(COOH)C6H4-CH=N-NH-thiazole-4-(2-Cl-C6H4)-5-ethyl |
| 15 | 2-(COOH)C6H4-CH=N-NH-thiazole-5-methyl-4-(2-Cl-C6H4) |
| 17 | 2-(COOH)C6H4-CH=N-NH-(4-methyl-5-phenylthiazol-2-yl) |
| 19 | 2-(COOH)C6H4-CH=N-N(CH3)-thiazole-4-(2,5-diCl-C6H3) |
| 20 | 2-(COOH)C6H4-CH=N-N(CH3)-(4-phenylthiazol-2-yl) |
| 21 | 2-(COOH)C6H4-CH=N-N(CH3)-thiazole-4-(3-Cl-C6H4) |

| No. | Structure |
|---|---|
| 22 | 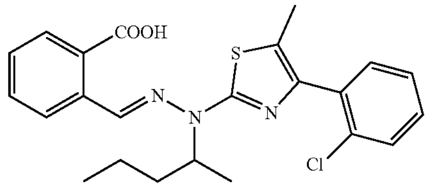 [SMILES: CCCC(C)N(/N=C/c1ccccc1C(=O)O)c1nc(-c2ccccc2Cl)c(C)s1] |
| 23 | 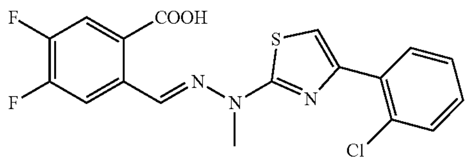 [SMILES: CN(/N=C/c1cc(F)c(F)cc1C(=O)O)c1nc(-c2ccccc2Cl)cs1] |
| 23-1 | 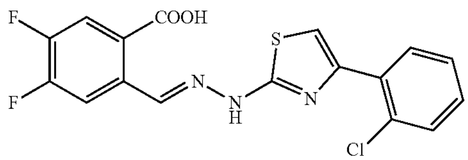 [SMILES: O=C(O)c1cc(F)c(F)cc1/C=N/Nc1nc(-c2ccccc2Cl)cs1] |
| 24 | 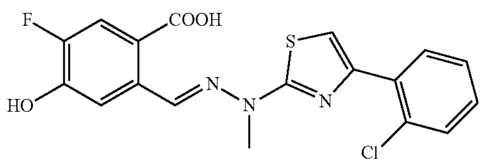 [SMILES: CN(/N=C/c1cc(O)c(F)cc1C(=O)O)c1nc(-c2ccccc2Cl)cs1] |
| 25 | 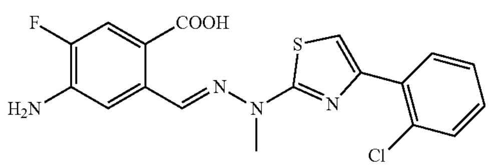 [SMILES: CN(/N=C/c1cc(N)c(F)cc1C(=O)O)c1nc(-c2ccccc2Cl)cs1] |
| 58 | 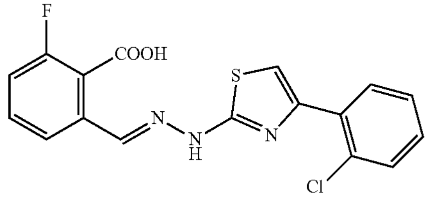 [SMILES: O=C(O)c1c(F)cccc1/C=N/Nc1nc(-c2ccccc2Cl)cs1] |
| A1 | 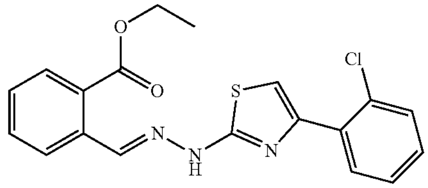 [SMILES: CCOC(=O)c1ccccc1/C=N/Nc1nc(-c2ccccc2Cl)cs1] |
| A2 | 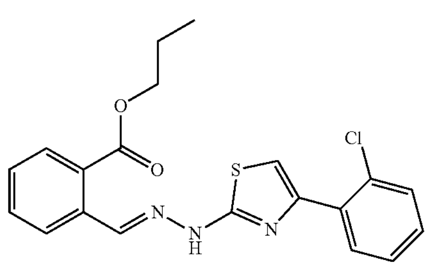 [SMILES: CCCOC(=O)c1ccccc1/C=N/Nc1nc(-c2ccccc2Cl)cs1] |
| A3 | |
| A4 | |
| A5 | |
| A6 | |
| A7 | |
| A8 | |

-continued

| No. | Structure |
|---|---|
| A9 | 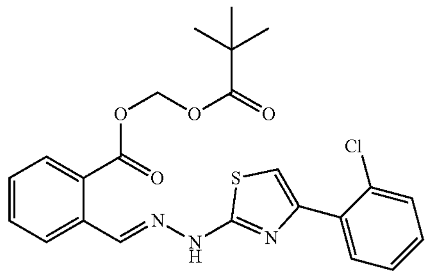 [SMILES: CC(C)(C)C(=O)OCOC(=O)c1ccccc1/C=N/Nc1nc(-c2ccccc2Cl)cs1] |
| A10 | 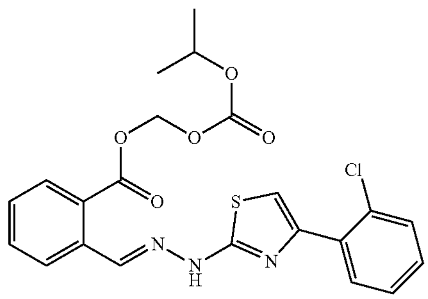 [SMILES: CC(C)OC(=O)OCOC(=O)c1ccccc1/C=N/Nc1nc(-c2ccccc2Cl)cs1] |
| A11 | 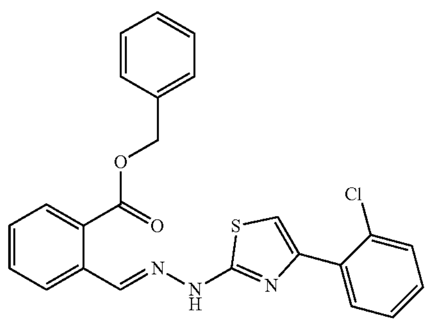 [SMILES: O=C(OCc1ccccc1)c1ccccc1/C=N/Nc1nc(-c2ccccc2Cl)cs1] |
| A12 | 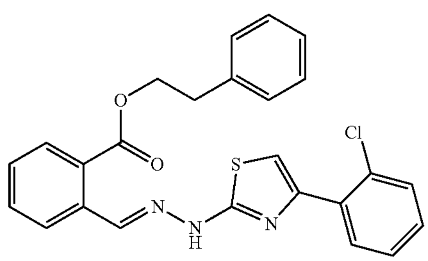 [SMILES: O=C(OCCc1ccccc1)c1ccccc1/C=N/Nc1nc(-c2ccccc2Cl)cs1] |
| A13 | 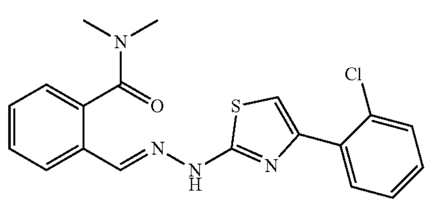 [SMILES: CN(C)C(=O)c1ccccc1/C=N/Nc1nc(-c2ccccc2Cl)cs1] |
| B1 | 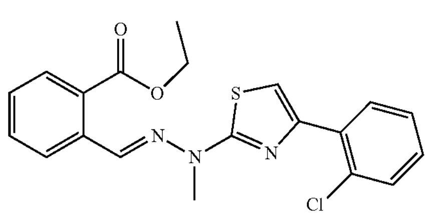 [SMILES: CCOC(=O)c1ccccc1/C=N/N(C)c1nc(-c2ccccc2Cl)cs1] |

-continued

| No. | Structure |
|---|---|
| B2 | 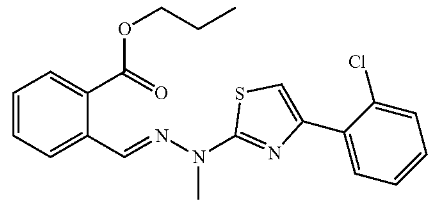 [SMILES: CCCOC(=O)c1ccccc1/C=N/N(C)c1nc(-c2ccccc2Cl)cs1] |
| B3 | 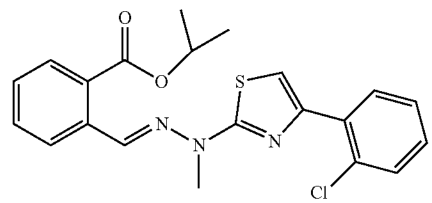 |
| B4 | 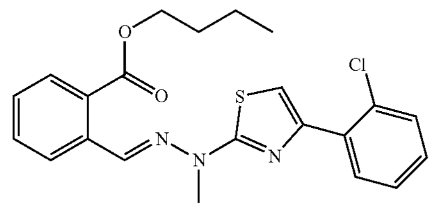 [SMILES: CCCCOC(=O)c1ccccc1/C=N/N(C)c1nc(-c2ccccc2Cl)cs1] |
| B5 | 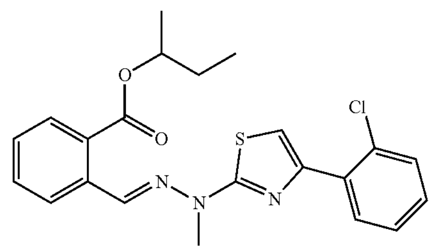 [SMILES: CCC(C)OC(=O)c1ccccc1/C=N/N(C)c1nc(-c2ccccc2Cl)cs1] |
| B6 | 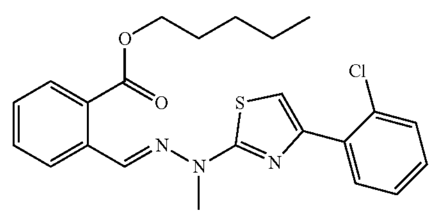 [SMILES: CCCCCOC(=O)c1ccccc1/C=N/N(C)c1nc(-c2ccccc2Cl)cs1] |
| B7 | 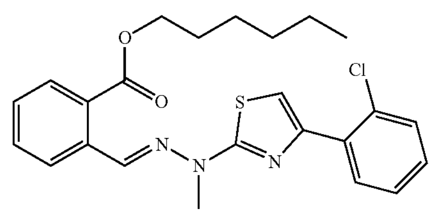 [SMILES: CCCCCCOC(=O)c1ccccc1/C=N/N(C)c1nc(-c2ccccc2Cl)cs1] |
| B8 | 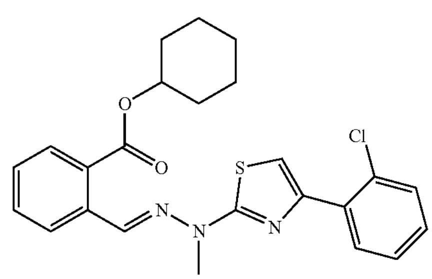 [SMILES: CN(/N=C/c1ccccc1C(=O)OC1CCCCC1)c1nc(-c2ccccc2Cl)cs1] |

| No. | Structure |
|---|---|
| B9 | 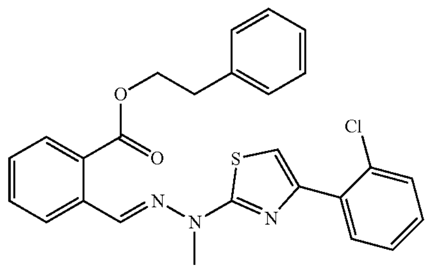 [SMILES: CN(/N=C/c1ccccc1C(=O)OCCc1ccccc1)c1nc(-c2ccccc2Cl)cs1] |
| B10 | 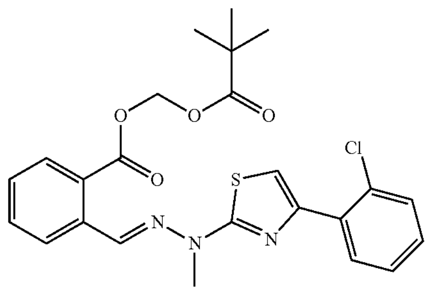 [SMILES: CN(/N=C/c1ccccc1C(=O)OCOC(=O)C(C)(C)C)c1nc(-c2ccccc2Cl)cs1] |
| B11 | 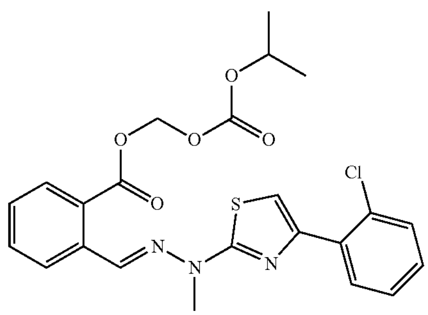 [SMILES: CC(C)OC(=O)OCOC(=O)c1ccccc1/C=N/N(C)c1nc(-c2ccccc2Cl)cs1] |
| B12 | 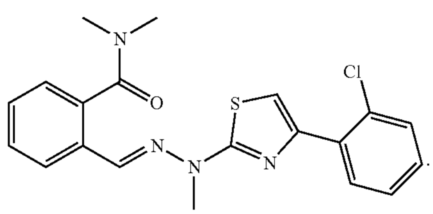 [SMILES: CN(C)C(=O)c1ccccc1/C=N/N(C)c1nc(-c2ccccc2Cl)cs1] |
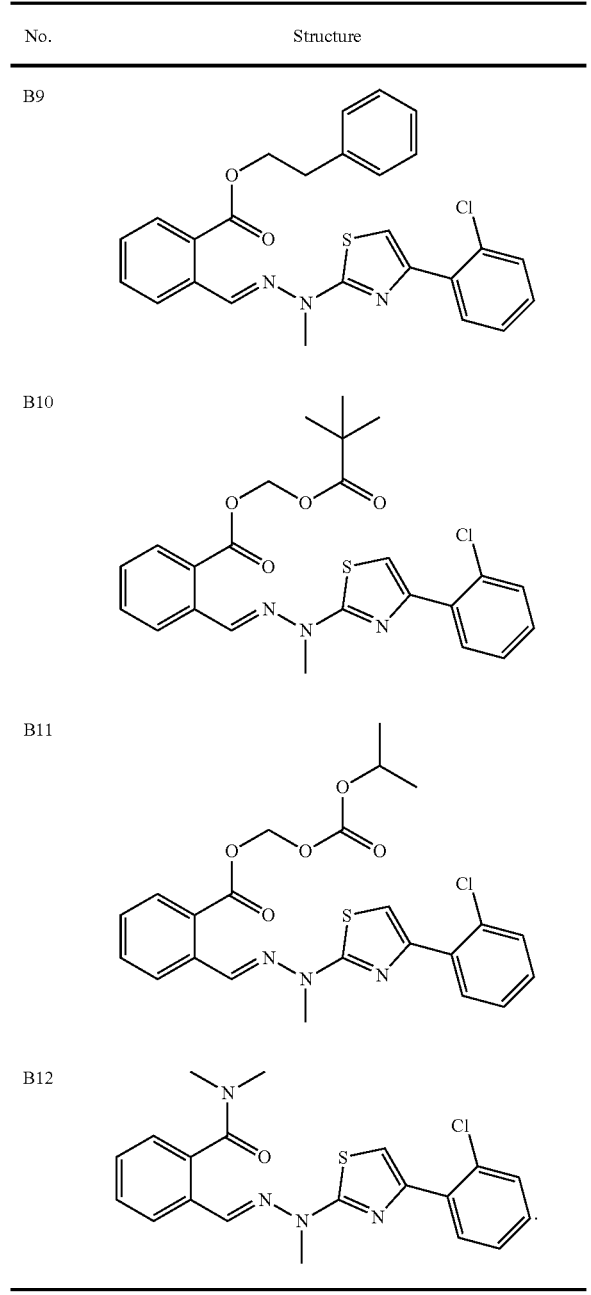
In a specific embodiment, a compound or a pharmaceutically acceptable salt or ester thereof selected from the following group is provided in the invention:
| No. | Structure |
|---|---|
| 1 | 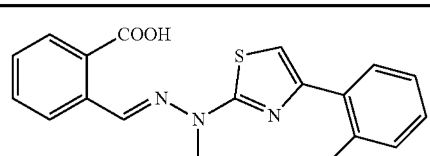 |
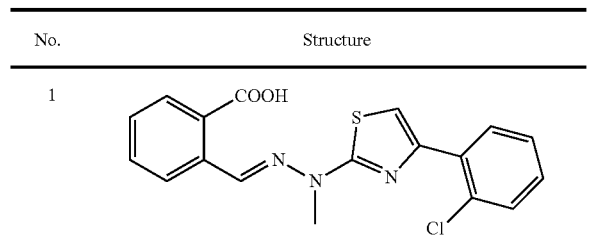
| No. | Structure |
|---|---|
| 3 | 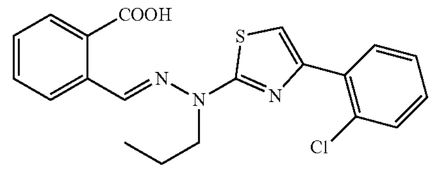 [SMILES: CCCN(/N=C/c1ccccc1C(=O)O)c1nc(-c2ccccc2Cl)cs1] |
| 8-1 | 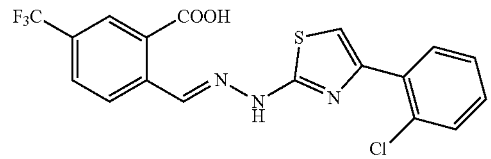 [SMILES: O=C(O)c1cc(C(F)(F)F)ccc1/C=N/Nc1nc(-c2ccccc2Cl)cs1] |
| 9 | 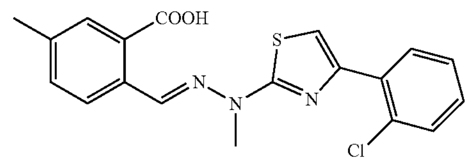 [SMILES: Cc1ccc(/C=N/N(C)c2nc(-c3ccccc3Cl)cs2)c(C(=O)O)c1] |
| 9-1 | 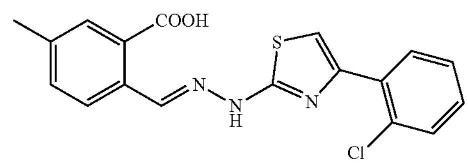 [SMILES: Cc1ccc(/C=N/Nc2nc(-c3ccccc3Cl)cs2)c(C(=O)O)c1] |
| 10 | 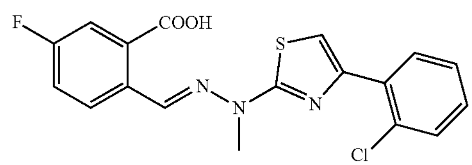 |
| 10-1 | 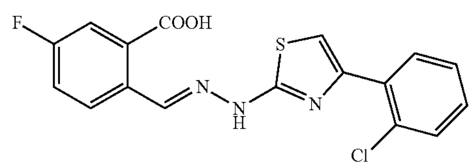 [SMILES: O=C(O)c1cc(F)ccc1/C=N/Nc1nc(-c2ccccc2Cl)cs1] |
| 11 | 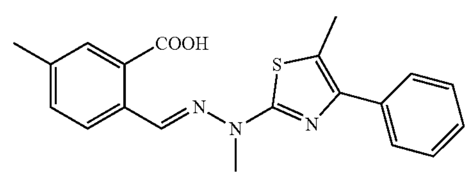 [SMILES: Cc1ccc(/C=N/N(C)c2nc(-c3ccccc3)c(C)s2)c(C(=O)O)c1] |
| 12 | 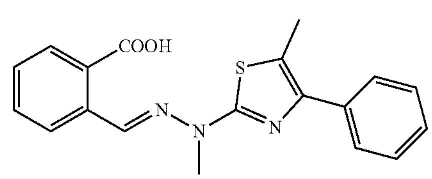 [SMILES: Cc1sc(N(C)/N=C/c2ccccc2C(=O)O)nc1-c1ccccc1] |
| 12-1 | 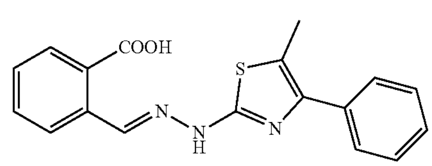 [SMILES: Cc1sc(N/N=C/c2ccccc2C(=O)O)nc1-c1ccccc1] |
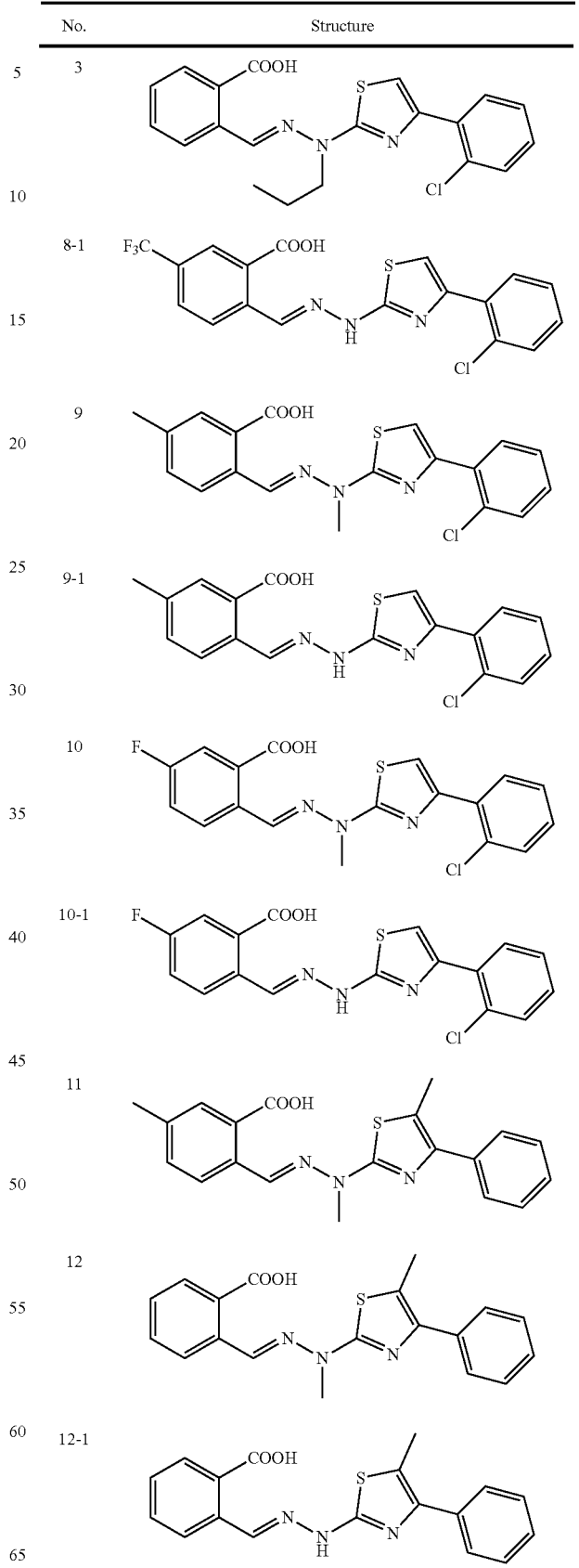

| No. | Structure |
|---|---|
| 21 | 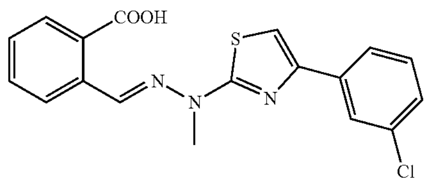 [SMILES: CN(/N=C/c1ccccc1C(=O)O)c1nc(-c2cccc(Cl)c2)cs1] |
| 22 | 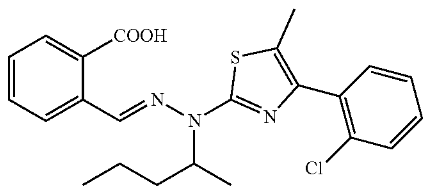 [SMILES: CCCC(C)N(/N=C/c1ccccc1C(=O)O)c1nc(-c2ccccc2Cl)c(C)s1] |
| 23 | 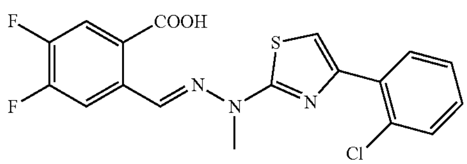 [SMILES: CN(/N=C/c1cc(F)c(F)cc1C(=O)O)c1nc(-c2ccccc2Cl)cs1] |
| 23-1 | 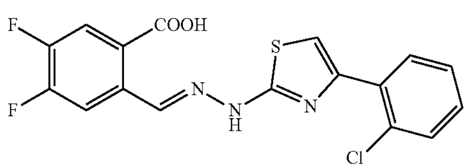 [SMILES: O=C(O)c1cc(F)c(F)cc1/C=N/Nc1nc(-c2ccccc2Cl)cs1] |
| A1 | 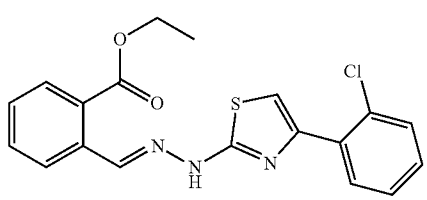 [SMILES: CCOC(=O)c1ccccc1/C=N/Nc1nc(-c2ccccc2Cl)cs1] |
| A2 | 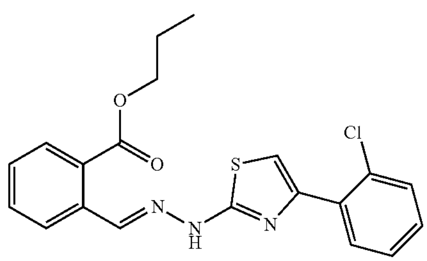 [SMILES: CCCOC(=O)c1ccccc1/C=N/Nc1nc(-c2ccccc2Cl)cs1] |
| A3 | 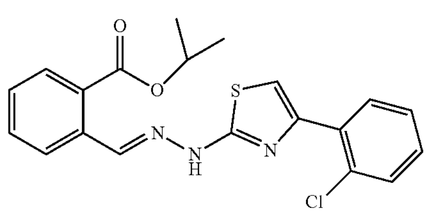 |

| No. | Structure |
|---|---|
| A4 | 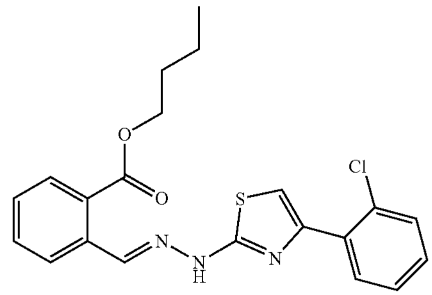 [SMILES: CCCCOC(=O)c1ccccc1/C=N/Nc1nc(-c2ccccc2Cl)cs1] |
| A5 | 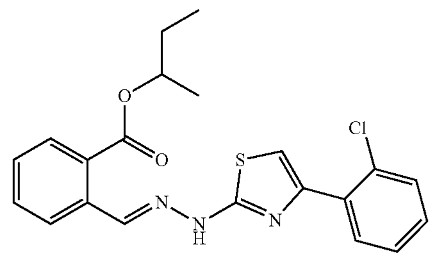 [SMILES: CCC(C)OC(=O)c1ccccc1/C=N/Nc1nc(-c2ccccc2Cl)cs1] |
| A6 | 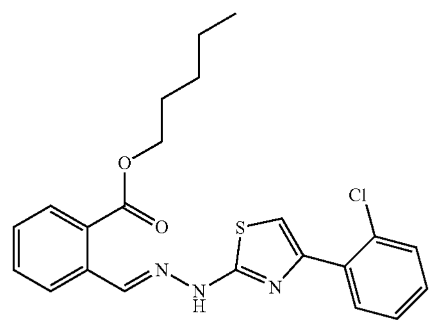 [SMILES: CCCCCOC(=O)c1ccccc1/C=N/Nc1nc(-c2ccccc2Cl)cs1] |
| A7 | 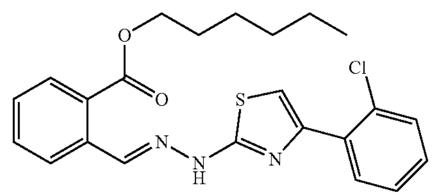 [SMILES: CCCCCCOC(=O)c1ccccc1/C=N/Nc1nc(-c2ccccc2Cl)cs1] |
| A8 | 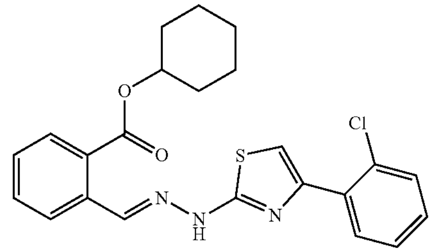 [SMILES: O=C(OC1CCCCC1)c1ccccc1/C=N/Nc1nc(-c2ccccc2Cl)cs1] |

| No. | Structure |
|---|---|
| A9 | 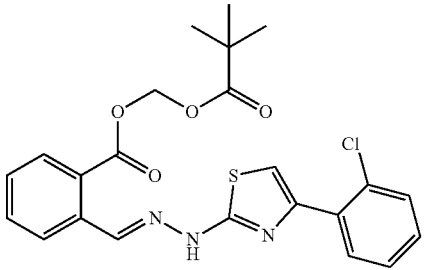 [SMILES: CC(C)(C)C(=O)OCOC(=O)c1ccccc1/C=N/Nc1nc(-c2ccccc2Cl)cs1] |
| A10 | 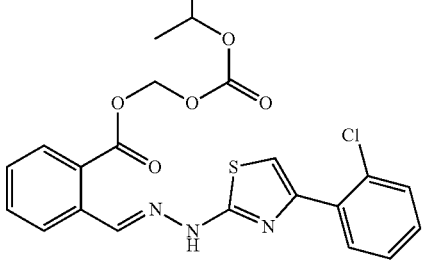 |
| A11 | 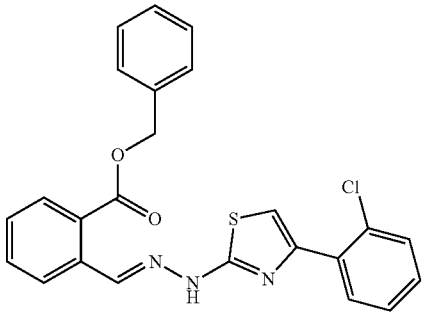 [SMILES: O=C(OCc1ccccc1)c1ccccc1/C=N/Nc1nc(-c2ccccc2Cl)cs1] |
| A12 | 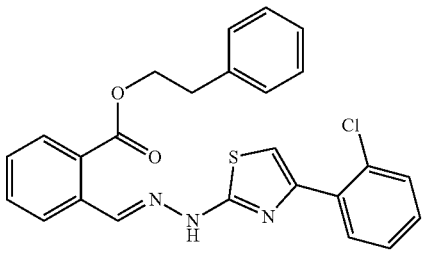 [SMILES: O=C(OCCc1ccccc1)c1ccccc1/C=N/Nc1nc(-c2ccccc2Cl)cs1] |
| A13 | 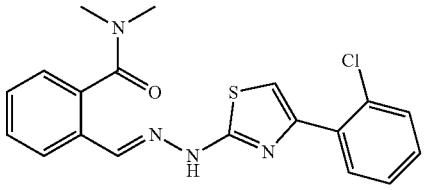 [SMILES: CN(C)C(=O)c1ccccc1/C=N/Nc1nc(-c2ccccc2Cl)cs1] |
| B1 | 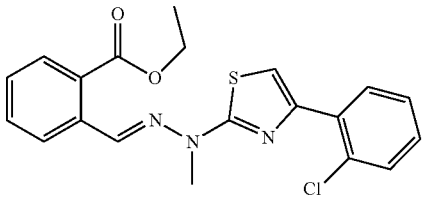 [SMILES: CCOC(=O)c1ccccc1/C=N/N(C)c1nc(-c2ccccc2Cl)cs1] |
| B2 | 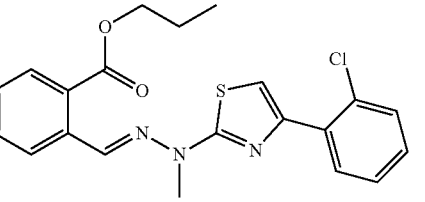 |
| B3 | 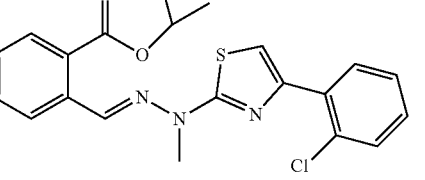 |
| B4 | 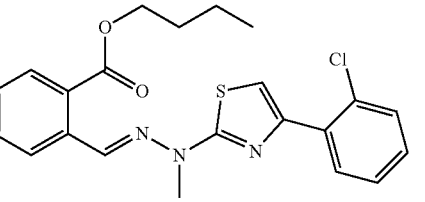 |
| B5 | 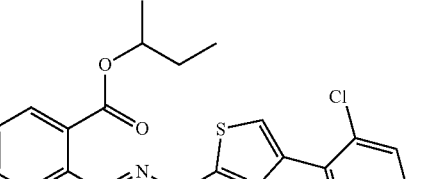 |
| B6 | 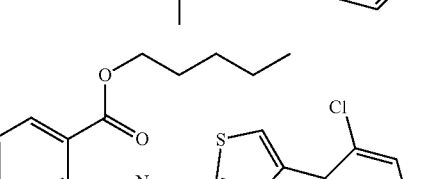 |
| B7 | 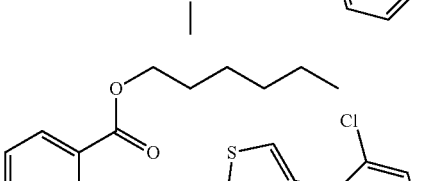 |
| B8 | 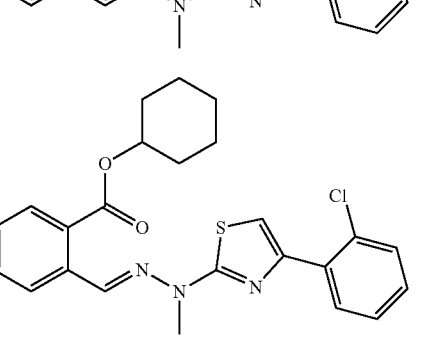 |

-continued

| No. | Structure |
|---|---|
| B9 | 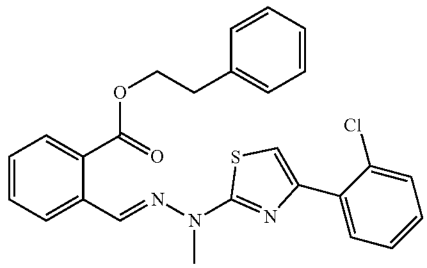 [SMILES: CN(/N=C/c1ccccc1C(=O)OCCc1ccccc1)c1nc(-c2ccccc2Cl)cs1] |
| B10 | 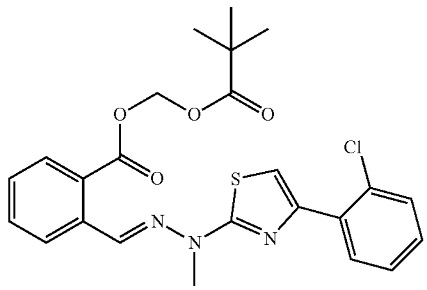 [SMILES: CN(/N=C/c1ccccc1C(=O)OCOC(=O)C(C)(C)C)c1nc(-c2ccccc2Cl)cs1] |
| B11 | 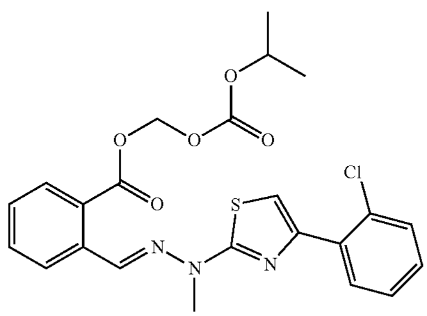 [SMILES: CC(C)OC(=O)OCOC(=O)c1ccccc1/C=N/N(C)c1nc(-c2ccccc2Cl)cs1] |
| B12 | 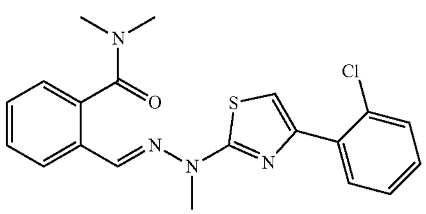 |

In a third aspect, a pharmaceutical composition is provided in the present invention, comprising a compound or a pharmaceutically acceptable salt or ester thereof of the first or second aspect of the present invention, and a pharmaceutically acceptable carrier or excipient.

In a preferred embodiment, the pharmaceutical composition is a dosage form suitable for oral administration, including but not limited to a tablet, solution, suspension, capsule, granule, powder.

In a fourth aspect, the use of a compound or a pharmaceutically acceptable salt or ester thereof of the first or second aspect of the invention is provided in the invention for preparing a medicament for treating DHODH-mediated diseases.

In a specific embodiment, the DHODH-mediated diseases include, but are not limited to, autoimmune diseases, bacterial infections, parasites and tumors.

In a specific embodiment, the autoimmune disease includes, but is not limited to, rheumatoid arthritis, organ transplant rejection, psoriasis.

In a fifth aspect, a method for treating DHODH-mediated diseases are provided in the present invention, comprising administering a compound or a pharmaceutically acceptable salt or ester thereof of the first or second aspect of the invention, or the pharmaceutical composition of the third aspect of the invention to a subject in need thereof.

It is to be understood that, within the scope of the present invention, various technical features of the present invention and the technical features specifically described hereinafter (as in the Examples) may be combined with each other to constitute new or preferred technical solutions, which will not described one by one herein.

MODES FOR CARRYING OUT THE INVENTION

Figure 1:
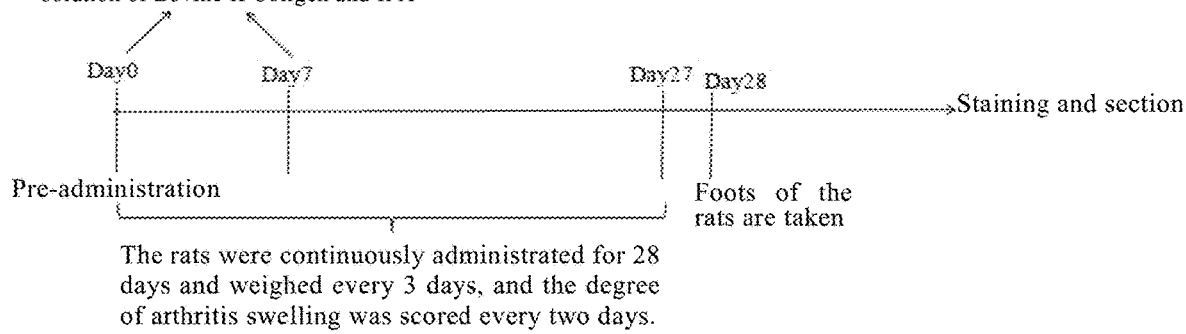
FIG. 1 is a schematic diagram of the rheumatoid arthritis experiment of Wistar rat (corresponding to Compound 1).

After extensive and intensive research, the inventors have unexpectedly discovered a series of thiazole derivatives, structural skeletons of which are completely different from those of highly active DHODH inhibitors reported in the literature (e.g., leflunomide, teriflamine, Brequinar). These compounds show significant DHODH inhibitory activities in testes at molecular, cellular and animal level, low toxicities, good safety and thus good prospects for being developed into medicaments. The present invention has been completed based the above discoveries.

Definition of Terms

Some groups mentioned herein are defined as follows:

As used herein, "alkyl" refers to a saturated branched or straight-chain alkyl in a carbon chain length of 1 to 10 carbon atoms, and a preferred alkyl includes an alkyl having from 2 to 8 carbon atoms, 1 to 6, 1 to 4 and 1-3 carbon atoms. Examples of alkyl include, but are not limited to, methyl, ethyl, n-propyl, isopropyl, n-butyl, isobutyl, heptyl and the like. The alkyl may be substituted by one or more substituents, for example halogen or haloalkyl. For example, the alkyl may be an alkyl substituted with 1 to 4 fluorine atoms, or the alkyl may be an alkyl substituted with a fluoroalkyl.

As used herein, "cycloalkyl" means a saturated alkyl with alicyclic structure, for example, a C3-C6 cycloalkyl. In a specific embodiment, the cycloalkyl includes, but is not limited to, cyclopropyl, cyclobutyl, cyclopentyl or cyclohexyl. The cycloalkyl described herein may be substituted or unsubstituted, including but not limited to, substituted with one or more halogen atoms, such as fluorine atoms.

As used herein, "amino" refers to a group of the formula "$NR_xR_y$", wherein Rx and $R_y$ may be independently selected from H or a $C_1$-$C_3$ alkyl or $C_1$-$C_3$ haloalkyl. In a specific embodiment, "amino" as used herein refers to $NH_2$.

As used herein, "halogen" refers to fluoro, chloro, bromo and iodo. In a preferred embodiment, the halogen is chlorine or fluorine; more preferably fluorine.

Compounds of the Invention

The present inventors have unexpectedly discovered a series of thiazole derivatives with novel structural skeletons, which exhibit significant DHODH inhibitory activity in tests at molecular, cellular and animal level, low toxicity, good safety, and thus good prospects for being developed into medicaments.

In a specific embodiment, the compound of the invention is shown in the following structural formula:

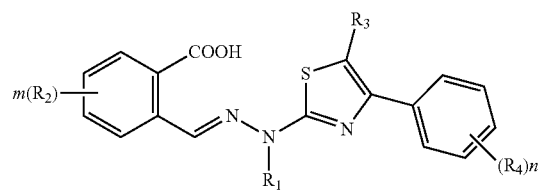

I wherein, $R_1$ is selected from the group consisting of: H, a substituted or unsubstituted C1-C6 alkyl and C3-C6 cycloalkyl;

$R_2$ is selected from the group consisting of: H, halogen, a substituted or unsubstituted C1-C6 alkyl, substituted or unsubstituted C1-C6 alkoxy, CN, $NO_2$, hydroxy, $NR^aR^b$;

$R^a$, $R^b$ are independently selected from H or C1-C6 alkyl;

$R_3$ is selected from the group consisting of: H, a substituted or unsubstituted C1-C6 alkyl;

$R_4$ is selected from H or halogen;

m is an integer from 0-4;

n is an integer from 0 to 5;

wherein, when $R_2$ is H and $R_3$ is H, $R_1$ is not H.

In a preferred embodiment, the compound of the invention is shown in Formula II:

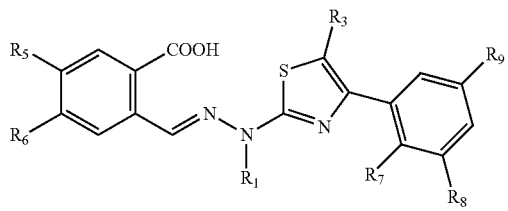

Wherein, $R_5$ and $R_6$ are independently selected from the group consisting of H, halogen, a substituted or unsubstituted C1-C6 alkyl, substituted or unsubstituted C1-C6 alkoxy, hydroxy, $NH_2$;

$R_7$, $R_8$ and $R_9$ are independently selected from H or halogen;

$R_1$ and $R_3$ are described as above.

In a further embodiment, $R_1$ is selected from a C1-C6 alkyl (preferably C1-C3 alkyl); $R_3$ is selected from the group consisting of H, a substituted or unsubstituted C1-C6 alkyl (preferably C1-C3 alkyl); $R_5$ and $R_6$ are independently selected from the group consisting of H, halogen (preferably F), an unsubstituted or halogen (preferably F)-substituted C1-C3 alkyl; $R_7$ and $R_8$ are independently selected from the group consisting of H and halogen (preferably CO; and $R_9$ is H; or, $R_1$ is selected from the group consisting of H and C1-C6 alkyl, preferably C1-C3 alkyl; $R_3$ is selected from the group consisting of H and substituted or unsubstituted C1-C6 alkyl (preferably C1-C3 alkyl); $R_5$ is selected from the group consisting of H and halogen (preferably F), an unsubstituted or halogen (preferably F)-substituted C1-C3 alkyl; $R_6$ is selected from the group consisting of H, halogen (preferably F), hydroxyl and $NH_2$; $R_7$ and $R_8$ are independently selected from H and halogen (preferably CO; and $R_9$ is H.

A pharmaceutical composition comprising a therapeutically effective amount of a compound or a pharmaceutically acceptable salt or ester thereof of the present invention, and a pharmaceutically acceptable carrier or excipient, based on the above compounds, is further provided in the present invention.

Examples of the pharmaceutically acceptable salt of a compound of the invention include, but are not limited to, inorganic and organic acid salts such as hydrochloride, hydrobromide, sulfate, citrate, lactate, tartrate, maleate, fumarate, mandelate and oxalate; and inorganic and organic base salts formed with bases such as sodium hydroxide, tris(hydroxymethyl)aminomethane (TRIS, tromethamine) and N-methyl glucosamine.

A pharmaceutically acceptable ester of a compound of the invention is a compound wherein the carboxyl of the compound of formula I is esterified, including but not limited to: an ester formed from a substituted or unsubstituted C1-C10 alkyl or cycloalkyl,

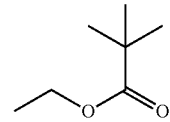

or

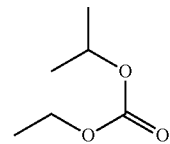

with the compound of formula I, wherein "substituted" means that a group is substituted with a group selected from phenyl or halogen. Typically, a pharmaceutically acceptable ester of a compound of the invention is selected from the group consisting of:

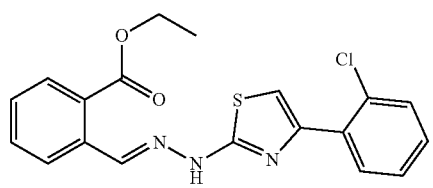

A1

-continued

A2, A3, A4, A5, A6, A7, A8, A9, A10, A11, A12, A13

B1 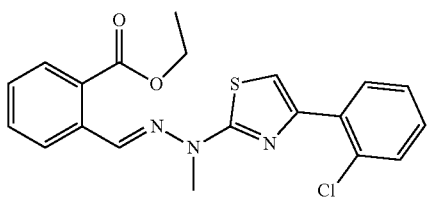

B2 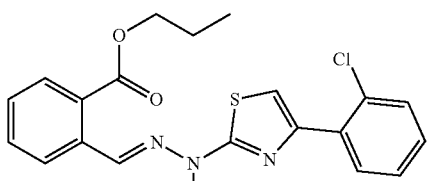

B3 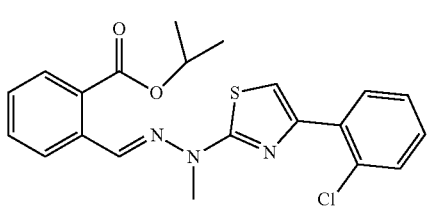

B4 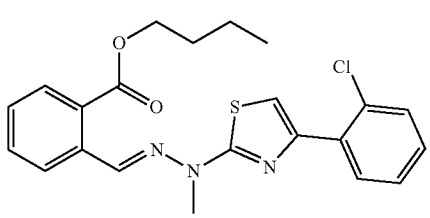

B5 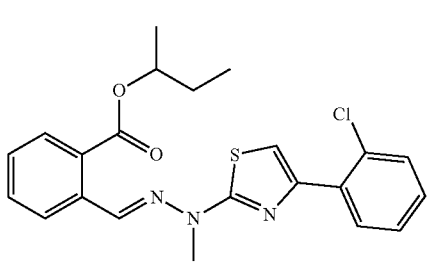

B6 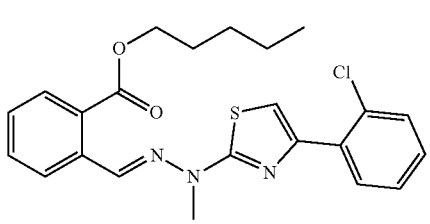

B7 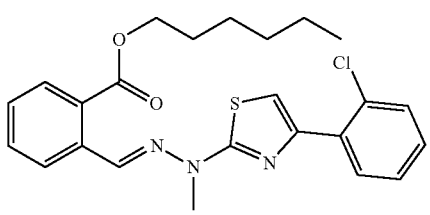

B8 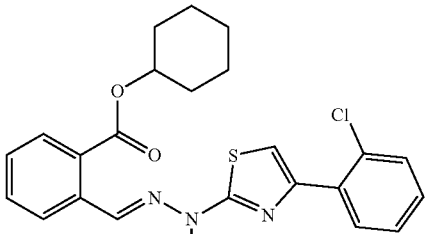

B9 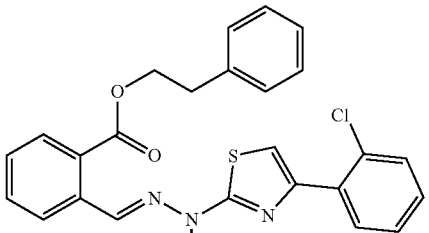

B10 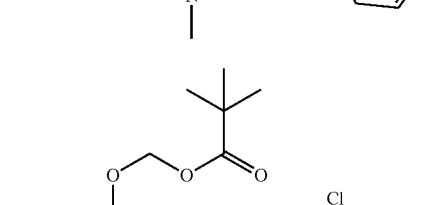

B11 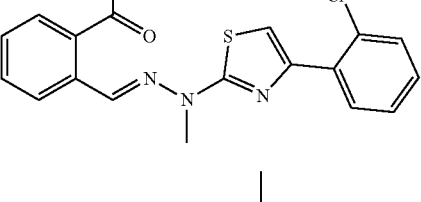

B12 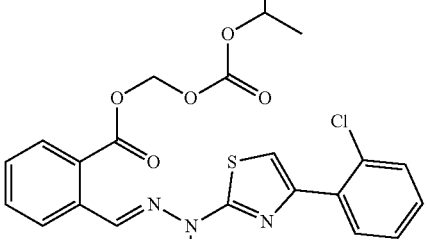

A skilled person in the art can determine the optimal dosage of each active ingredient in the pharmaceutical composition of the present invention, although the needs of each person vary. In general, the compound of the present invention or a pharmaceutically acceptable salt thereof is orally administered to a mammal in an amount of from about 0.0025 to 50 mg/kg body weight per day. However, it is preferably about 0.01 to 10 mg per kilogram for oral administration. For example, a unit oral dose can include from about 0.01 to 50 mg, preferably from about 0.1 to 10 mg, of a compound of the invention. The unit dose may be administered one or more times per day in one or more tablets, and each tablet contains from about 0.1 to 50 mg, preferably from about 0.25 to 10 mg of a compound of the invention or a solvate thereof.

The pharmaceutical composition of the present invention can be formulated into a dosage form suitable for various administration routes, including but not limited to, a dosage form suitable for parenteral, subcutaneous, intravenous, intramuscular, intraperitoneal, transdermal, oral, intrathecal, intracranial, intranasal or topical administration for treating tumors and other diseases. The administered amount is an amount effective to ameliorate or eliminate one or more conditions. For the treatment of a particular disease, an effective amount is a dosage sufficient to ameliorate or, in some way, alleviate symptoms associated with a disease. Such a dosage can be administered in a single dose or can be administered according to an effective therapeutic regimen. The administered amount may cure the disease, but usually is to improve symptoms of the disease. Repeated administrations are generally required to achieve the desired improvement in symptoms. The dosage of the drug will be determined according to the age, health and weight of a patient, the type of concurrent treatment, the frequency of treatment, and the desired therapeutic benefits.

The pharmaceutical preparation of the present invention can be administered to any mammal as long as they can obtain therapeutic effects of the compound of the present invention. The most important among these mammals is humans. The compounds of the invention or pharmaceutical compositions thereof are useful for treating a variety of DHODH-mediated diseases. Herein, DHODH-mediated diseases are autoimmune diseases, organ transplant rejection, bacterial infections, parasitic diseases or tumors. In a specific embodiment, the autoimmune disease is rheumatoid arthritis, lupus erythematosus or psoriasis.

The pharmaceutical preparations of the invention can be prepared in a known manner. For example, it is manufactured by a conventional mixing, granulating, tableting, dissolving, or freeze-drying process. When manufacturing oral formulations, the mixture can be selectively milled by combining solid auxiliary substances and the active compound. If necessary, after adding an appropriate amount of auxiliary substances, the mixture of granules is processed to obtain a tablet or tablet core.

Suitable auxiliary substances are, in particular, fillers, for example sugars, such as lactose or sucrose, mannitol or sorbitol; cellulose preparations or calcium phosphates, such as tricalcium phosphate or calcium hydrogen phosphate; and binders, such as starch pastes, including corn starch, wheat starch, rice starch, potato starch, gelatin, tragacanth, methyl cellulose, hydroxypropyl methyl cellulose, sodium carboxymethyl cellulose, or polyvinylpyrrolidone. If necessary, a disintegrating agent such as the above-mentioned starch, and carboxymethyl starch, crosslinked polyvinylpyrrolidone, agar, or alginic acid or a salt thereof such as sodium alginate may be added. Auxiliary substances can be, in particular, flow regulators and lubricants, for example, silica, talc, stearates such as calcium magnesium stearate, stearic acid or polyethylene glycol. If desired, the tablet core can be provided with a suitable coating that is resistant to gastric juice. For this purpose, a concentrated sugar solution can be applied. Such solutions may contain gum arabic, talc, polyvinylpyrrolidone, polyethylene glycol and/or titanium dioxide, lacquer solutions and suitable organic solvents or solvent mixtures. For preparing a gastric juice-resistant coating, a suitable cellulose solution such as cellulose acetate ortho-phthalate or hydroxypropyl methylcellulose ortho-phthalate can be used. A dye or pigment can be added to the coating of the tablet or tablet core for, for example, identification or for characterizing the combination of dosages of active ingredients.

Accordingly, a method for treating DHODH-mediated diseases is also provided in the present invention, which comprises administering to a subject in need thereof a compound of the invention or a pharmaceutical composition comprising a compound of the invention.

Methods of administration include, but are not limited to, various methods of administration well known in the art, which can be determined based on the actual circumstances of a patient. The methods include, but are not limited to, parenteral, subcutaneous, intravenous, intramuscular, intraperitoneal, transdermal, buccal, intrathecal, intracranial, nasal or topical administration.

The invention also encompasses the use of a compound of the invention in the manufacture of a medicament for treating DHODH-mediated diseases.

Further, a skilled person will, based on the common knowledge in the art and the contents of the present invention, appreciate that a compound of the present invention can form a salt or an ester due to the contained carboxyl, thereby forming a prodrug.

Advantages of the Invention

1. A series of structurally novel thiazole derivatives are firstly discovered in the present invention;
2. The compound of the present invention is a highly effective and low-toxic DHODH inhibitor, and thus has important academic value and practical significance.

Technical solutions of the present invention are further described below in combination with specific examples, but the following examples are not intended to limit the invention, and all methods of application according to the principles and technical means of the present invention shall fall within the scope of the invention. Experimental methods in the following examples which do not specify specific conditions are usually carried out according to conventional conditions or conditions recommended by manufacturers. Percentages and parts are calculated by weight unless otherwise stated.

Example 1

(E)-4-(2-chlorophenyl)-2-[1-methyl-2-(2-carboxybenzylidene)hydrazino]thiazole 1

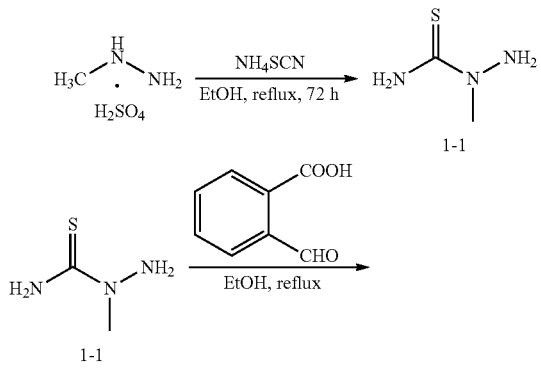

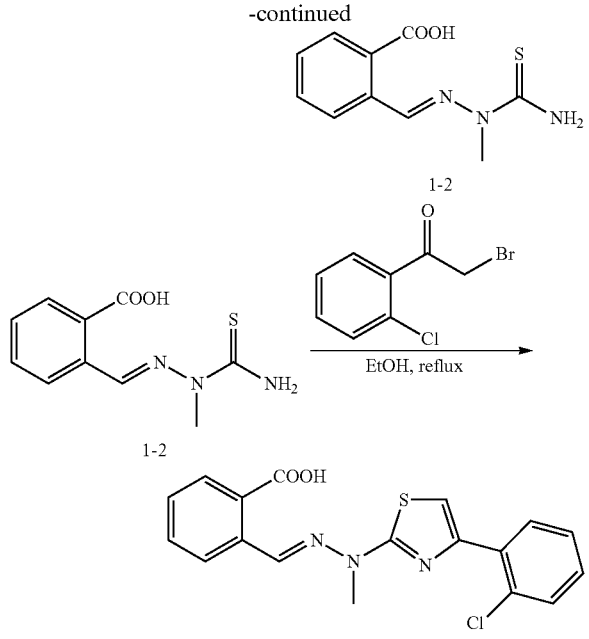

2-methylthiosemicarbazide (1-1)

2.5 g (17.3 mmol) of methyl hydrazine sulfate was weighed into a 250 ml single-mouth flask, 100 ml of ethanol was added, and 1.6 g (20.8 mmol) of ammonium thiocyanate was added with stirring. The reaction mixture was heated to reflux for 72 h. The reaction solution was cooled to room temperature and suction-filtered. The obtained filtrate was then evaporated to dryness and separated through silica gel column chromatography (DCM /MeOH=40:1) to give a second side product as white powdery solids (0.63 g, yield 34.2%). $^1$H NMR (400 MHz, DMSO-d6, ppm) δ 7.36 (s, 2H), 4.89 (s, 2H), 3.41 (s, 3H). GC-MS (EI) calcd for C2H7N3S [M]+105.0, found 105.0.

2-methyl-1-(2-carboxybenzylidene)thiosemicarbazide (1-2)

80 mg (0.76 mmol) of compound (1-1) was weighted into a 50 ml single-mouth flask, 20 ml of ethanol was added, and o-carboxybenzaldehyde (114 mg, 0.76 mmol) was added with stirring. The reaction mixture was heated to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give white powdery solids (100 mg, yield 56%). $^1$H NMR (400 MHz, DMSO-d6, ppm) δ 13.36 (br, 1H), 8.56 (s, 1H), 8.51 (s, 1H), 8.31 (d, J=7.8 Hz, 1H), 8.25 (s, 1H), 7.88 (d, J=8 Hz, 1H), 7.59 (t, J=7.2 Hz, 1H), 7.50 (t, J=7.2 Hz, 1H), 3.77 (s, 3H). LC-MS (ESI) calcd for C$_{10}$H$_{12}$N$_3$O$_2$S [M+H]$^+$ 238.1, found 238.1.

(E)-4-(2-chlorophenyl)-2-[1-methyl-2-(2-carboxybenzylidene)hydrazino]thiazole 1

100 mg (0.42 mmol) of compound (2) was weighed into a 50 ml single-mouth flask, 10 ml of ethanol was added, and 65 μL (0.42 mmol) of 2'-chloro-2-bromoacetophenone was added with stirring. The reaction mixture was warmed to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give yellow powdery solids (106 mg, yield 67.9%). Mp. 210.4-212.0° C. $^1$H NMR (400 MHz, DMSO-d6, ppm) δ 13.30 (s, 1H), 8.62 (s, 1H), 8.02 (d, J=7.6 Hz, 1H), 7.98-7.90 (m, 2H), 7.66 (t, J=7.6 Hz, 1H), 7.56-7.49 (m, 2H), 7.47 (s, 1H), 7.43 (td, J$_1$=7.4 Hz, J$_2$=1.2 Hz, 1H), 7.36 (td, J$_1$=7.6 Hz, J$_2$=1.6 Hz, 1H), 3.68 (s, 3H). $^{13}$C NMR (125 MHz, DMSO-d6, ppm) δ 168.98, 168.57, 147.11, 136.94, 135.17, 133.42, 132.48, 131.51, 131.09, 130.98, 130.75, 130.16, 129.45, 129.19, 127.63, 126.51, 111.41, 32.88. HRMS (ESI) calcd for C$_{18}$H$_{15}$N$_3$O$_2$SCl [M+H]$^+$ 372.0574, found 372.0575.

The inventors further synthesized following compounds using a similar method and corresponding starting materials:

(E)-4-(2-chlorophenyl)-2-[1-ethyl-2-(2-carboxybenzylidene)hydrazino]thiazole 2

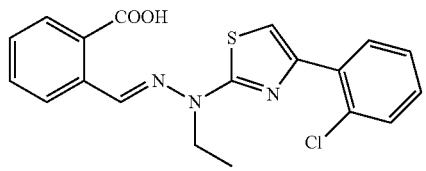 [SMILES: CCN(/N=C/c1ccccc1C(=O)O)c1nc(-c2ccccc2Cl)cs1]

Mp. 203.3-204.1° C. $^1$H NMR (500 MHz, DMSO-d$_6$, ppm) δ 13.32 (br, 1H), 8.64 (s, 1H), 7.98-7.91 (m, 3H), 7.66 (t, J=7.5 Hz, 1H), 7.56-7.46 (m, 2H), 7.45-7.39 (m, 2H), 7.34 (t, J=6.8 Hz, 1H), 4.32 (q, J=6.8 Hz, 2H), 1.27 (t, J=7.0 Hz, 3H). $^{13}$C NMR (125 MHz, DMSO-d$_6$, ppm) δ 168.56, 168.36, 147.34, 137.00, 135.42, 133.53, 132.50, 131.53, 131.12, 130.92, 130.72, 130.22, 129.42, 129.19, 127.62, 126.62, 111.22, 40.38, 10.33. HRMS (ESI) calcd for C$_{19}$H$_{17}$N$_3$O$_2$SCl [M+H]$^+$ 386.0730, found 386.0728.

(E)-4-(2-chlorophenyl)-2-[1-propyl-2-(2-carboxybenzylidene)hydrazino]thiazole 3

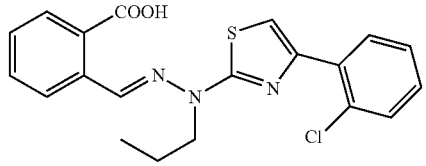 [SMILES: CCCN(/N=C/c1ccccc1C(=O)O)c1nc(-c2ccccc2Cl)cs1]

Mp. 172.6-173.4° C. $^1$H NMR (400 MHz, DMSO-d$_6$, ppm) δ 13.35 (br, 1H), 8.65 (s, 1H), 7.98 (d, J=8.0 Hz, 1H), 7.95-7.92 (m, 2H), 7.67 (t, J=7.2 Hz, 1H), 7.54 (d, J=8.0 Hz, 1H), 7.5 (t, J=7.6 Hz, 1H), 7.45-7.42 (m, 2H), 7.36 (t, J$_1$=7.6 Hz, J$_2$=1.6 Hz, 1H), 4.25 (t, J=7.2 Hz, 2H), 1.82-1.73 (m, 2H), 0.97 (t, J=7.4 Hz, 1H). $^{13}$C NMR (100 MHz, DMSO-d6, ppm) δ 168.54, 168.22 146.95, 136.63, 134.96, 133.17, 132.11, 131.10, 130.74, 130.55, 130.34, 129.82, 129.04, 128.80, 127.26, 126.09, 110.77, 46.31, 17.98, 11.17. HRMS (ESI) calcd for C20H19N3O2SCl [M+H]$^+$ 400.0887, found 400.0879.

(E)-4-(2-chlorophenyl)-2-[1-isopropyl-2-(2-carboxybenzylidene)hydrazino]thiazole 4

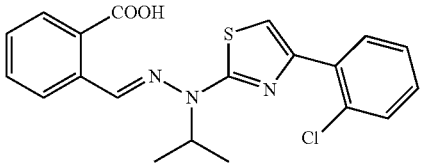 [SMILES: CC(C)N(/N=C/c1ccccc1C(=O)O)c1nc(-c2ccccc2Cl)cs1]

Mp. 185.4-187.0° C. $^1$H NMR (400 MHz, DMSO-d6, ppm) δ 13.35 (br, 1H), 8.91 (s, 1H), 7.99 (d, J=8.0 Hz, 1H), 7.95-7.92 (m, 2H), 7.67 (t, J=7.6 Hz, 1H), 7.54 (d, J=8.0 Hz, 1H), 7.52 (t, J=7.6 Hz, 1H), 7.46-7.42 (m, 2H), 7.36 (td, $J_1$=7.6 Hz, $J_2$=1.6 Hz, 1H), 5.22-5.11 (m, 1H), 1.57 (d, J=6.8 Hz, 6H). $^{13}$C NMR (100 MHz, DMSO-d$_6$, ppm) δ 168.22, 168.21, 146.90, 137.32, 135.23, 133.14, 132.07, 131.06, 130.64, 130.58, 130.39, 129.88, 128.97, 128.78, 127.28, 125.91, 111.12, 49.61, 18.07, 18.07. HRMS (ESI) calcd for $C_{20}H_{19}N_3O_2SCl$ [M+H]$^+$ 400.0887, found 400.0885.

(E)-4-(2-chlorophenyl)-2-[1-(2-butyl)-2-(2-carboxybenzylidene)hydrazino]thiazole 5

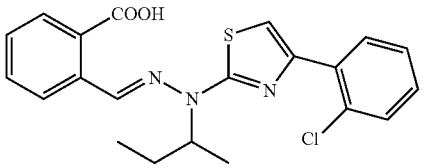 [SMILES: CCC(C)N(/N=C/c1ccccc1C(=O)O)c1nc(-c2ccccc2Cl)cs1]

Mp. 170.5-170.6° C. $^1$H NMR (400 MHz, DMSO-d$_6$, ppm) δ 13.32 (br, 1H), 8.91 (s, 1H), 7.99 (d, J=8.0 Hz, 1H), 7.95-7.90 (m, 2H), 7.67 (t, $J_1$=7.6 Hz, 1H), 7.55-7.48 (m, 2H), 7.46-7.42 (m, 2H), 7.36 (td, $J_1$=7.6 Hz, $J_2$=1.6 Hz, 1H), 5.00-4.93 (m, 1H), 2.35-2.24 (m, 1H), 1.92-1.81 (m, 1H), 1.54 (d, J=6.8 Hz, 3H), 0.88 (t, J=7.2 Hz, 3H). $^{13}$C NMR (100 MHz, DMSO-d$_6$, ppm) δ 168.66, 168.19, 146.97, 137.03, 135.24, 133.19, 132.13, 131.04, 130.67, 130.58, 130.39, 129.70, 128.98, 128.77, 127.29, 125.91, 111.04, 55.67, 25.26, 16.33, 11.14. HRMS (ESI) calcd for $C_{21}H_{21}N_3O_2SCl$ [M+H]$^+$ 414.1043, found 414.1029.

(E)-4-(2-chlorophenyl)-2-[1-(2-amyl)-2-(2-carboxybenzylidene)hydrazino]thiazole 6

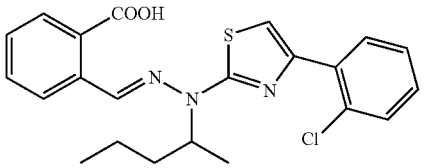 [SMILES: CCCC(C)N(/N=C/c1ccccc1C(=O)O)c1nc(-c2ccccc2Cl)cs1]

Mp. 146.7-147.0° C. $^1$H NMR (400 MHz, DMSO-d6, ppm) δ 13.35 (br, 1H), 8.91 (s, 1H), 7.98 (d, J=7.6 Hz, 1H), 7.94 (d, J=8.0 Hz, 1H), 7.91 (dd, $J_1$=7.6 Hz, $J_2$=1.6 Hz, 1H), 7.67 (t, J=7.6 Hz, 1H), 7.53 (d, J=8.0 Hz, 1H), 7.49 (t, J=7.6 Hz, 1H), 7.46-7.42 (m, 2H), 7.36 (td, $J_1$=7.6 Hz, $J_2$=1.6 Hz, 1H), 5.14-5.06 (m, 1H), 2.34-2.25 (m, 1H), 1.82-1.73 (m, 1H), 1.53 (d, J=6.8 Hz, 3H), 1.34-1.24 (m, 2H), 0.89 (t, J=7.4 Hz, 1H). $^{13}$C NMR (100 MHz, DMSO-d$_6$, ppm) δ 168.68, 168.20, 146.98, 137.04, 135.30, 133.20, 132.14, 131.00, 130.68, 130.59, 130.40, 129.68, 128.99, 127.30, 125.90, 111.09, 53.81, 34.20, 19.46, 16.46, 13.60. HRMS (ESI) calcd for $C_{22}H_{23}N_3O_2SCl$ [M+H]$^+$ 428.1200, found 428.1193.

(E)-4-(2-chlorophenyl)-2-[1-hydroxyethyl-2-(2-carboxybenzylidene)hydrazino]thiazole

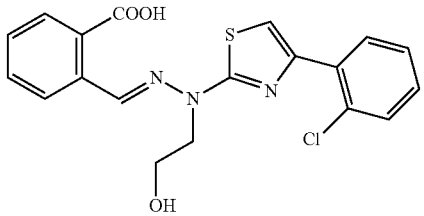 [SMILES: O=C(O)c1ccccc1/C=N/N(CCO)c1nc(-c2ccccc2Cl)cs1]

Mp. 187.9-188.9° C. $^1$H NMR (400 MHz, DMSO-d$_6$, ppm) δ 13.24 (br, 1H), 8.75 (s, 1H), 7.98-7.01 (m, 3H), 7.66 (t, J=7.6 Hz, 1H), 7.54 (d, J=8.0 Hz, 1H), 7.49 (t, J=7.6 Hz, 1H), 7.45-7.41 (m, 2H), 7.36 (td, $J_1$=7.6 Hz, $J_2$=1.6 Hz, 1H), 4.35 (t, J=6.4 Hz, 2H), 3.76 (t, J=6.4 Hz, 2H). $^{13}$C NMR (100 MHz, DMSO-d$_6$, ppm) δ 168.64, 168.23, 146.87, 136.89, 134.91, 133.15, 131.99, 131.19, 130.71, 130.46, 130.32, 130.16, 129.04, 128.79, 127.22, 126.28, 110.78, 56.24, 47.46. HRMS (ESI) calcd for $C_{19}H_{17}N_3O_3SCl$ [M+H]$^+$ 402.0679, found 402.0678.

(E)-4-(2-chlorophenyl)-2-[1-methyl-2-(4-trifluoromethyl-2-carboxybenzylidene)hydrazino]thiazole 8

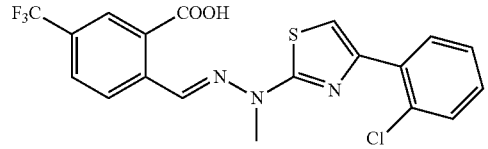 [SMILES: CN(/N=C/c1ccc(C(F)(F)F)cc1C(=O)O)c1nc(-c2ccccc2Cl)cs1]

Mp. 209.3-210.7° C. $^1$H NMR (400 MHz, DMSO-d$_6$, ppm) δ 14.02 (br, 1H), 8.66 (s, 1H), 8.21 (d, J=8.0 Hz, 1H), 8.17 (s, 1H), 8.02 (d, J=8.0 Hz, 1H), 7.95 (d, J=7.6 Hz, 1H), 7.56-7.53 (m, 2H), 7.43 (t, J=7.6 Hz, 1H), 7.37 (t, J=7.6 Hz, 1H), 3.70 (s, 3H). $^{13}$C NMR (100 MHz, DMSO-d$_6$, ppm) δ 168.33, 167.17, 146.79, 138.38, 135.01, 132.91, 131.12, 130.70, 130.37, 129.14, 128.57, 128.25, 128.20, 127.26, 127.04, 125.10, 122.40, 111.51, 32.68. HRMS (ESI) calcd for $C_{19}H_{14}N_3O_2SClF_3$ [M+H]$^+$ 440.0447, found 440.0433.

(E)-4-(2-chlorophenyl)-2-[1-methyl-2-(4-methyl-2-carboxybenzylidene)hydrazino]thiazole 9

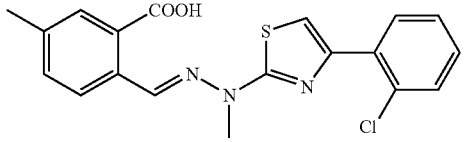 [SMILES: Cc1ccc(/C=N/N(C)c2nc(-c3ccccc3Cl)cs2)c(C(=O)O)c1]

Mp. 231.3-232.5° C. $^1$H NMR (400 MHz, DMSO-d$_6$, ppm) δ 13.30 (br, 1H), 8.59 (s, 1H), 7.96 (d, J=7.6 Hz, 1H), 7.92 (d, J=8.0 Hz, 1H), 7.75 (s, 1H), 7.54 (d, J=7.6 Hz, 1H), 7.49-7.46 (m, 2H), 7.43 (t, J=7.6 Hz, 1H), 7.36 (t, J=7.6 Hz, 1H), 3.66 (s, 3H), 2.38 (s, 3H). $^{13}$C NMR (100 MHz, DMSO-d$_6$, ppm) δ 168.60, 168.35, 146.68, 138.54, 136.64, 133.03, 132.70, 132.07, 131.11, 130.86, 130.67, 130.34, 129.83, 129.00, 127.21, 126.04, 110.84, 32.39, 20.69. HRMS (ESI) calcd for C$_{19}$H$_{17}$N$_3$O$_2$SCl [M+H]$^+$ 386.0730, found 386.0738.

(E)-4-(2-chlorophenyl)-2-[1-methyl-2-(2-carboxyl-4-fluorobenzylidene)hydrazino]thiazole 10

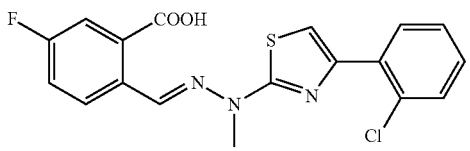 [SMILES: CN(/N=C/c1ccc(F)cc1C(=O)O)c1nc(-c2ccccc2Cl)cs1]

Mp. 228.6-229.7° C. $^1$H NMR (400 MHz, DMSO-d$_6$, ppm) δ 13.28 (br, 1H), 8.14 (s, 1H), 7.93 (dd, J$_1$=7.6 Hz, J$_2$=1.6 Hz, 1H), 7.61 (dd, J$_1$=7.0 Hz, J$_2$=1.8 Hz, 1H), 7.55-7.49 (m, 3H), 7.44-7.41 (m, 1H), 7.36 (td, J$_1$=7.6 Hz, J$_2$=1.6 Hz, 1H), 3.68 (s, 3H). $^{13}$C NMR (100 MHz, DMSO-d$_6$, ppm) δ 168.55, 168.01, 159.74 (d, $^1$J=249 Hz), 146.67, 133.68, 133.10, 131.50, 131.12, 130.72, 130.32, 130.10 (d, $^3$J=8.8 Hz), 129.06, 127.23, 125.53 (d, $^4$J=3.1 Hz), 121.75 (d, $^2$J=11.8 Hz), 118.76 (d, $^2$J=22 Hz), 111.13, 32.28. HRMS (ESI) calcd for C$_{18}$H$_{14}$N$_3$O$_2$FSCl [M+H]$^+$ 390.0479, found 390.0475.

(E)-5-methyl-4-phenyl-2-[1-methyl-2-(4-methyl-2-carboxybenzylidene)hydrazino]thiazole 11

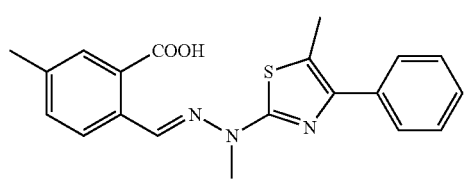 [SMILES: Cc1ccc(/C=N/N(C)c2nc(-c3ccccc3)c(C)s2)c(C(=O)O)c1]

Mp. 243.2-245.2° C. $^1$H NMR (400 MHz, DMSO-d6, ppm) δ 13.24 (br, 1H), 8.54 (s, 1H), 7.91 (d, J=8.0 Hz, 1H), 7.73 (s, 1H), 7.64-7.53 (m, 2H), 7.46-7.42 (m, 3H), 7.33 (t, J=7.4 Hz, 1H), 3.60 (s, 3H), 2.44 (s, 3H), 2.38 (s, 3H). $^{13}$C NMR (100 MHz, DMSO-d$_6$, ppm) δ 168.35, 165.40, 145.43, 138.33, 135.76, 135.16, 132.68, 132.22, 130.86, 129.62, 128.24, 128.24, 127.85, 127.85, 127.06, 125.89, 119.27, 31.85, 20.68, 12.24. HRMS (ESI) calcd for C$_{20}$H$_{20}$N$_3$O$_2$S [M+H]$^+$ 366.1276, found 366.1273.

(E)-5-methyl-4-phenyl-2-[1-methyl-2-(2-carboxybenzylidene)hydrazino]thiazole 12

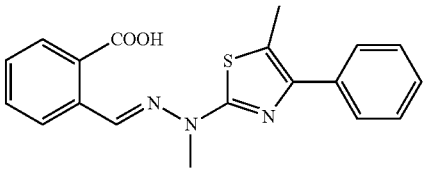 [SMILES: Cc1sc(N(C)/N=C/c2ccccc2C(=O)O)nc1-c1ccccc1]

Mp. 222.7-224.9° C. $^1$H NMR (400 MHz, DMSO-d$_6$, ppm) δ 13.32 (br, 1H), 8.58 (s, 1H), 8.01 (d, J=8.0 Hz, 1H), 7.92 (d, J=7.6 Hz, 1H), 7.68-7.63 (m, 3H), 7.50-7.43 (m, 3H), 7.34 (t, J=7.4 Hz, 1H), 3.62 (s, 3H), 2.44 (s, 3H). $^{13}$C NMR (100 MHz, DMSO-d6, ppm) δ 168.24, 165.36, 145.47, 135.66, 135.13, 134.90, 131.98, 130.58, 129.70, 128.59, 128.25, 128.25, 127.86, 127.86, 127.09, 125.94, 119.44, 31.93, 12.24. HRMS (ESI) calcd for C$_{19}$H$_{16}$N$_3$O$_2$S [M−H]$^−$ 350.0963, found 350.0951.

(E)-4-(2-chlorophenyl)-2-[1-methyl-2-(2-carboxybenzylidene)hydrazino]thiazole 13

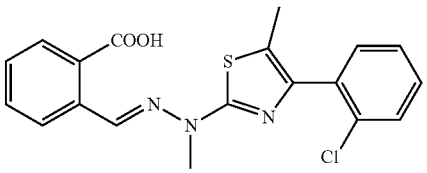 [SMILES: Cc1sc(N(C)/N=C/c2ccccc2C(=O)O)nc1-c1ccccc1Cl]

Mp. 208.8-209.8° C. $^1$H NMR (400 MHz, DMSO-d$_6$, ppm) δ 13.46 (br, 1H), 8.60 (s, 1H), 8.01 (d, J=8.0 Hz, 1H), 7.92 (d, J=8.0 Hz, 1H), 7.64 (t, J=7.4 Hz, 1H), 7.56 (d, J=7.6 Hz, 1H), 7.49-7.39 (m, 4H), 3.56 (s, 3H), 2.15 (s, 3H). $^{13}$C NMR (100 MHz, DMSO-d$_6$, ppm) δ 168.98, 166.46, 144.56, 136.46, 135.29, 134.54, 133.25, 132.50, 132.31, 131.05, 130.72, 130.26, 130.01, 129.09, 127.49, 126.42, 121.85, 32.46, 12.16. HRMS (ESI) calcd for C$_{19}$H$_{17}$N$_3$O$_2$SCl [M+H]$^+$ 386.0730, found 386.0727.

(E)-5-ethyl-4-(2-chlorophenyl)-2-(2-carboxylbenzylidenehydrazino)thiazole 14

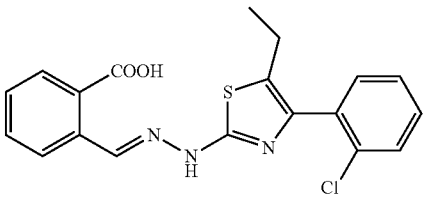 [SMILES: CCc1sc(N/N=C/c2ccccc2C(=O)O)nc1-c1ccccc1Cl]

Mp. 223.9-223.9° C. $^1$H NMR (500 MHz, DMSO-d6, ppm) δ 12.57 (br, 2H), 8.79 (s, 1H), 8.01 (d, J=8.0 Hz, 1H), 7.88 (d, J=8.0 Hz, 1H), 7.62 (t, J=7.5 Hz, 1H), 7.56-7.51 (m, 1H), 7.46 (t, J=7.5 Hz, 1H), 7.44-7.36 (m, 3H), 2.49 (q, J=7.5 Hz, 2H), 1.13 (t, J=7.5 Hz, 3H). $^{13}$C NMR (125 MHz, DMSO-d$_6$, ppm) δ 169.28, 165.92, 144.14, 140.84, 135.89, 135.46, 133.99, 133.03, 133.02, 131.46, 130.81, 130.73, 130.60, 129.73, 128.09, 127.73, 127.01, 20.99, 17.25. HRMS (ESI) calcd for $C_{19}H_{17}N_3O_2SCl$ [M+H]$^+$ 386.0730, found 386.0729.

(E)-5-methyl-4-(2-chlorophenyl)-2-(2-carboxylbenzylidenehydrazino)thiazole 15

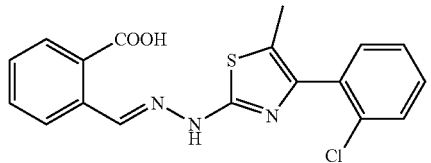 [SMILES: Cc1sc(N/N=C/c2ccccc2C(=O)O)nc1-c1ccccc1Cl]

Mp. 217.6-217.8° C. $^1$H NMR (400 MHz, DMSO-d$_6$, ppm) δ 12.7 (br, 2H), 8.77 (s, 1H), 7.99 (d, J=7.6 Hz, 1H), 7.87 (d, J=7.2 Hz, 1H), 7.62 (t, J=7.4 Hz, 1H), 7.562-7.543 (m, 1H), 7.481-7.397 (m, 4H), 2.14 (s, 3H). $^{13}$C NMR (125 MHz, DMSO-d$_6$, ppm) δ 168.65, 165.18, 144.49, 140.16, 135.25, 134.56, 133.21, 132.46, 130.83, 130.14, 130.03, 129.11, 127.45, 126.37, 119.49, 12.15. HRMS (ESI) calcd for $C_{18}H_{15}N_3O_2SCl$ [M+H]$^+$ 372.0574, found 372.0569.

(E)-5-methyl-4-phenyl-2-(2-carboxylbenzylidenehydrazino)thiazole 17

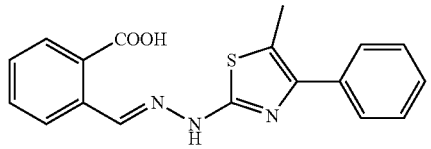 [SMILES: Cc1sc(N/N=C/c2ccccc2C(=O)O)nc1-c1ccccc1]

Mp. 215.9-216.0° C. $^1$H NMR (400 MHz, DMSO-d$_6$, ppm) δ 12.7 (br, 2H), 8.77 (s, 1H), 7.99 (d, J=7.6 Hz, 1H), 7.87 (dd, J$_1$=8.0 Hz, J$_2$=1.2 Hz, 1H), 7.63-7.59 (m, 3H), 7.48-7.43 (m, 3H), 7.33 (t, J=7.2 Hz, 1H), 2.43 (s, 3H). $^{13}$C NMR (125 MHz, DMSO-d$_6$, ppm) δ 168.66, 164.72, 146.00, 140.05, 135.64, 135.24, 132.36, 130.83, 130.12, 129.08, 128.73, 128.73, 128.35, 128.35, 127.51, 126.33, 117.61, 12.74. HRMS (ESI) calcd for $C_{18}H_{16}N_3O_2S$ [M+H]$^+$ 338.0963, found 338.0954.

(E)-4-(2,5-dichlorophenyl)-2-[1-methyl-2-(2-carboxybenzylidene)hydrazino]thiazole

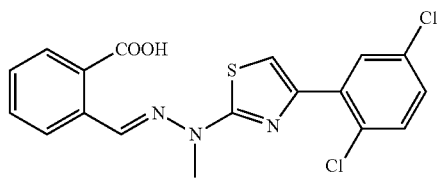 [SMILES: CN(/N=C/c1ccccc1C(=O)O)c1nc(-c2cc(Cl)ccc2Cl)cs1]

Mp. 268.4-269.5° C. $^1$H NMR (400 MHz, DMSO-d$_6$, ppm) δ 13.31 (br, 1H), 8.63 (s, 1H), 8.02-8.00 (m, 2H), 7.93 (d, J=7.2 Hz, 1H), 7.67 (t, J=7.6 Hz, 1H), 7.63 (s, 1H), 7.58 (d, J=7.6 Hz, 1H), 7.50 (t, J=7.2 Hz, 1H), 7.43 (dd, J$_1$=7.2 Hz, J$_2$=2.8 Hz, 1H), 3.68 (s, 3H). $^{13}$C NMR (100 MHz, DMSO-d$_6$, ppm) δ 168.68, 168.15, 145.13, 136.79, 134.70, 134.21, 132.14, 132.06, 131.85, 130.59, 130.17, 129.76, 129.20, 128.84, 128.58, 126.13, 112.31, 32.49. HRMS (ESI) calcd for $C_{18}H_{14}N_3O_2SCl_2$ [M+H]$^+$ 406.0184, found 406.0187.

(E)-4-phenyl-2-[1-methyl-2-(2-carboxybenzylidene)hydrazino]thiazole 20

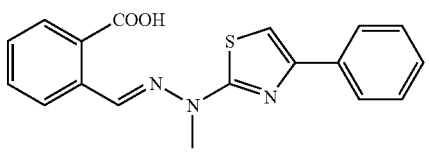 [SMILES: CN(/N=C/c1ccccc1C(=O)O)c1nc(-c2ccccc2)cs1]

Mp. 205.6-206.8° C. $^1$H NMR (400 MHz, DMSO-d$_6$, ppm) δ 13.31 (br, 1H), 8.62 (s, 1H), 8.02 (d, J=7.6 Hz, 1H), 7.94-7.91 (m, 3H), 7.66 (t, J=7.2 Hz, 1H), 7.49 (t, J=7.2 Hz, 1H), 7.45-7.40 (m, 3H), 7.31 (t, J=7.2 Hz, 1H), 3.71 (s, 3H). $^{13}$C NMR (100 MHz, DMSO-d6, ppm) δ 169.45, 168.20, 150.18, 136.35, 134.80, 134.49, 132.07, 130.60, 129.71, 128.76, 128.56, 128.56, 127.59, 126.09, 125.54, 125.54, 105.97, 32.51. HRMS (ESI) calcd for $C_{18}H_{16}N_3O_2S$ [M+H]$^+$ 338.0963, found 338.0963.

(E)-4-(3-chlorophenyl)-2-[1-methyl-2-(2-carboxybenzylidene)hydrazino]thiazole 21

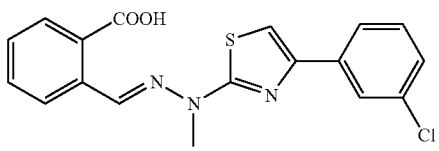 [SMILES: CN(/N=C/c1ccccc1C(=O)O)c1nc(-c2cccc(Cl)c2)cs1]

Mp. 244.7-245.4° C. $^1$H NMR (400 MHz, DMSO-d$_6$, ppm) δ 13.32 (br, 1H), 8.63 (s, 1H), 8.01 (d, J=7.6 Hz, 1H), 7.97 (s, 1H), 7.93 (d, J=7.6 Hz, 1H), 7.88 (d, J=8.0 Hz, 1H), 7.66 (t, J=7.6 Hz, 1H), 7.61 (s, 1H), 7.50 (t, J=7.6 Hz, 1H), 7.45 (t, J=7.6 Hz, 1H), 7.37 (d, J=8.0 Hz, 1H), 3.71 (s, 3H). $^{13}$C NMR (100 MHz, DMSO-d$_6$, ppm) δ 169.57, 168.18, 148.56, 136.64, 136.50, 134.72, 133.48, 132.06, 130.59, 130.44, 129.76, 128.81, 127.28, 126.12, 125.16, 124.05, 107.56, 32.52. HRMS (ESI) calcd for $C_{18}H_{15}N_3O_2SCl$ [M+H]+ 372.0574, found 372.0574.

(E)-5-methyl-4-(2-chlorophenyl)-2-[1-(2-amyl)-2-(2-carboxybenzylidene)hydrazino]thiazole 22

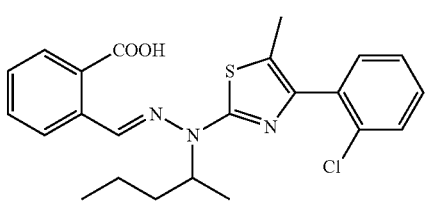 [SMILES: CCCC(C)N(/N=C/c1ccccc1C(=O)O)c1nc(-c2ccccc2Cl)c(C)s1]

Mp. 89.9-90.1° C. $^1$H NMR (400 MHz, DMSO-d6, ppm) δ 13.29 (br, 1H), 8.85 (s, 1H), 7.98 (d, J=8.0 Hz, 1H), 7.92 (d, J=7.6 Hz, 1H), 7.65 (t, J=7.6 Hz, 1H), 7.56-7.54 (m, 1H), 7.51-7.41 (m, 4H), 5.05-4.96 (m, 1H), 2.29-2.22 (m, 1H), 2.16 (s, 3H), 1.75-1.67 (m, 1H), 1.46 (d, J=7.2 Hz, 3H), 1.28-1.23 (m, 2H), 0.87 (t, J=7.6 Hz, 3H). $^{13}$C NMR (100 MHz, DMSO-d$_6$, ppm) δ 168.23, 166.06, 144.08, 136.14, 135.46, 134.09, 132.79, 132.09, 131.93, 130.58, 129.64, 129.60, 129.48, 128.56, 126.95, 125.73, 121.62, 53.39, 34.01, 19.41, 16.35, 13.58, 11.52. HRMS (ESI) calcd for $C_{23}H_{25}N_3O_2SCl$ [M+H]$^+$ 442.1356, found 442.1354.

(E)-2-((2-(4-(2-chlorophenyl)thiazol-2-yl)hydrazono)methyl)-6-fluorobenzoic acid (58)

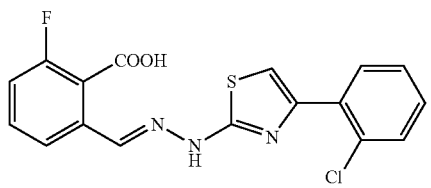 [SMILES: O=C(O)c1c(F)cccc1/C=N/Nc1nc(-c2ccccc2Cl)cs1]

Mp: 211.2-211.7° C. $^1$H NMR (400 MHz, DMSO-d$_6$): δ 12.40 (s, 1H), 8.18 (s, 1H), 7.86 (dd, $J_1$=7.6 Hz, $J_2$=1.6 Hz, 1H), 7.69 (d, J=8.0 Hz, 1H), 7.55-7.50 (m, 2H), 7.41 (t, J=7.6 Hz, 1H), 7.37 (s, 1H), 7.35 (t, J=7.6 Hz, 1H), 7.29 (t, J=8.8 Hz, 1H). $^{13}$C NMR (100 MHz, DMSO-d$_6$): 167.56, 166.14, 160.51, 158.06, 147.64, 138.21, 138.17, 133.94, 133.89, 133.68, 131.54, 131.25, 130.83, 129.53, 127.72, 122.04, 116.51, 116.29, 109.58. HRMS (ESI) calcd for $C_{17}H_{10}N_3O_2SClF$ [M−H]$^-$ 374.0166, found 374.0164. Purity: 97.09% ($t_R$ 12.05 min).

Synthesis of Prodrug of A Series 1-(2-propylidene)thiosemicarbazide 1

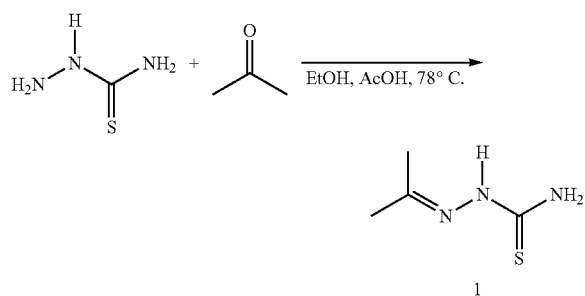

Thiosemicarbazide (10 g, 109.7 mmol) was weighed into a 500 mL three-necked flask, 200 mL of absolute ethanol was added, and acetone (8.1 mL, 109.7 mmol) and 2 mL of acetic acid were added with stirring, and heated to 78° C. The reaction was detected by TLC plate, the reaction was completed after 4 hours, and the heating was stopped. The reaction solution was allowed to stand overnight, and white flaky solids were precipitated, which were filtered to give crude product. The crude product was re-crystallized in water, and filtered to give a pure product of 12.1 g (yield 84%). $^1$H NMR (400 MHz, DMSO-d$_6$, ppm): δ 9.86 (s, 1H), 7.95 (s, 1H), 7.45 (s, 1H), 1.90 (s, 3H), 1.88 (s, 3H).

4-(2-chlorophenyl)-2-(2-propylidenehydrazino)thiazole 2

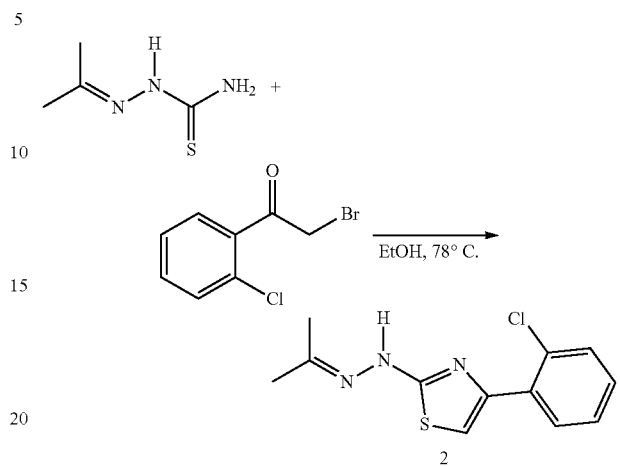

Compound 1 (9 g, 68.6 mmol) was weighed into a 500 mL three-necked flask, 200 mL of absolute ethanol was added, and 2-bromo-2'-chloroacetophenone (17.6 g, 75.5 mmol) was added with stirring at room temperature, and then heated to 78° C. The reaction was monitored by TLC. After 5 hours, the reaction was completed, the heating was stopped, and the reaction solution was allowed to stand and cooled to room temperature for precipitating yellow solids. The solids were filtered, and the filter cake was re-crystallized in ethanol, allowed to stand, filtered, and dried to give yellow powdery solids (14.2 g, yield 78%). $^1$H NMR (400 MHz, DMSO-d$_6$, ppm): δ 7.69 (d, J=7.8 Hz, 1H), 7.50 (d, J=7.8 Hz, 1H), 7.40 (m, 2H), 6.98 (s, 1H), 2.21 (s, 3H), 2.10 (s, 3H).

4-(2-chlorophenyl)-2-hydrazinothiazole 3

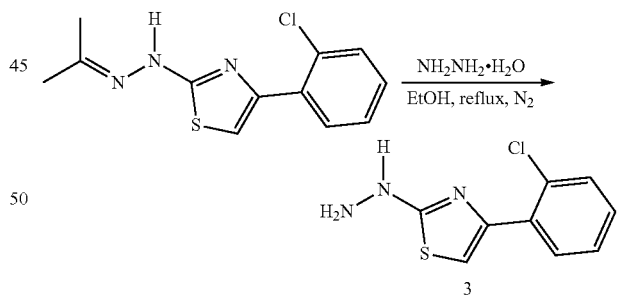

Compound 2 (10 g, 37.7 mmol) was weighed into a 250 mL three-necked flask, 130 mL of absolute ethanol was added, and 80% hydrazine hydrate (5.3 mL, 107.8 mmol) was added and heated to reflux under nitrogen atmosphere. A large amount of solids precipitated during heating. The reaction was quenched, and suction-filtrated to obtain 5 g of crude compound 3. The reaction mixture was refluxed for 12 h, and then the reaction was stopped. The reaction mixture was placed in a refrigerator overnight, and filtered to obtain 2 g of crude product. The crude product was re-crystallized in ethanol to give white flocculent solids (5.1 g, yield 60.7%). $^1$H NMR (400 MHz, DMSO-d$_6$, ppm): δ 8.58 (s, 1H), 7.86 (dd, $J_1$=7.8 Hz, $J_2$=2.0 Hz, 1H), 7.46 (dd, $J_1$=7.8 Hz, $J_2$=1.6 Hz, 1H), 7.38 (td, $J_1$=7.8 Hz, $J_2$=1.6 Hz, 1H), 7.27 (td, $J_1$=7.8 Hz, $J_2$=2.0 Hz, 1H), 7.10 (s, 1H), 4.85 (s, 2H). LC-MS (ESI) calcd for $C_9H_8N_3SCl$ [M+H]$^+$ 226.01, found 226.10.

(E)-4-(2-chlorophenyl)-2-(2-carboxylbenzylidenehydrazino)thiazole A

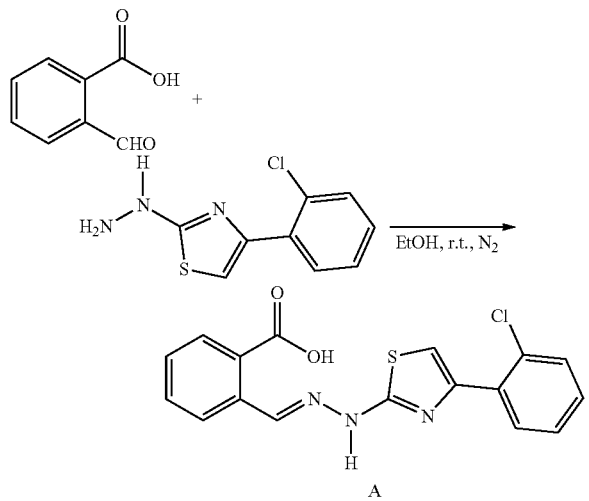

o-carboxybenzaldehyde (150 mg, 1 mmol) was weighed into a 50 mL single-mouth flask, compound 3 (225 mg, 1 mmol) was added, 30 mL of absolute ethanol was added, three drops of acetic acid were added as a catalyst, and stirred at room temperature under nitrogen. The reaction was monitored by TLC until the end of the reaction. The hot reaction mixture was filtered rapidly. The filter cake was rinsed for three times with iced ethanol, and dried to obtain bright yellow powdery solids (250 mg, yield 70%). Mp: 195-196° C. $^1$H NMR (400 MHz, DMSO-$d_6$, ppm): δ 13.30 (br, 1H), 12.05 (br, 1H), 8.84 (s, 1H), 8.02 (d, J=7.6 Hz, 1H), 7.91 (t, J=8.0 Hz, 2H), 7.66 (t, J=7.2 Hz, 1H), 7.55 (d, J=7.6 Hz, 1H), 7.51 (t, J=8 Hz, 1H), 7.44 (t, J=7.2 Hz, 1H), 7.38-7.34 (m, 2H). $^{13}$C NMR (100 MHz, DMSO-$d_6$, ppm): δ 168.12, 167.26, 140.26, 135.03, 134.55, 133.23, 131.94, 131.42, 131.05, 130.72, 130.34, 129.80, 129.01, 128.81, 127.22, 125.96, 109.26. HRMS (ESI) calcd for $C_{17}H_{13}N_3O_2SCl$ [M+H]$^+$ 358.0417, found 358.0419. HPLC purity: 96.88%, Retention time=9.34 min.

Ethyl 2-formylbenzoate 1a

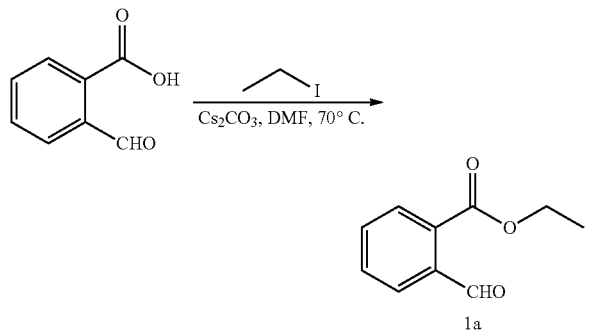

o-carboxybenzaldehyde (1.5 g, 10 mmol) was weighed into a 100 mL three-necked flask, cesium carbonate (6.5 g, 20 mmol) and 20 ml of N,N-dimethylformamide (DMF) were added, and ethyl iodide (4.68 g, 30 mmol) was added with electromagnetic-stirring and heated to 70° C. for 4 h. The reaction was monitored by TLC until the end of the reaction, and the heating was stopped. 20 mL of water was added to the reaction flask. The reaction mixture was extracted for three times with dichloromethane and water. The organic phases were pooled and dried over anhydrous sodium sulfate and suction-filtered, and the filtrate was evaporated to dryness and purified through silica gel column chromatography to give a colorless transparent liquid (1.4 g, yield 79%). $^1$H NMR (400 MHz, DMSO-$d_6$, ppm): δ 10.41 (s, 1H), 7.92-7.90 (m, 1H), 7.88-7.85 (m, 1H), 7.81-7.77 (m, 2H), 4.40 (q, J=7.2 Hz, 2H), 1.34 (t, J=7.2 Hz, 3H). LC-MS (ESI) calcd for $C_{10}H_{10}O_3$ [M+H]$^+$ 179.06, found 179.10.

(E)-4-(2-chlorophenyl)-2-(2-ethoxyformylbenzylidenehydrazino)thiazole A1

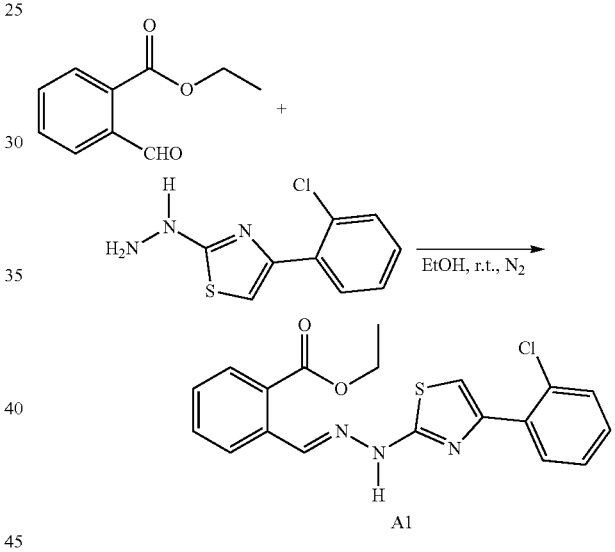

Compound 1a (178 mg, 1 mmol) was weighed into a 50 mL two-necked flask, another compound 3 (225 mg, 1 mmol) was added to the reaction flask, 15 mL of absolute ethanol was added, and the reaction was stirred under nitrogen for 4 h. The reaction was monitored by TLC until the starting materials were completely converted. The reaction mixture was suction-filtered, and the filter cake was rinsed with ethanol and dried to obtain 280 mg of a nearly pure product. After purification through a column, 220 mg of a pale yellow solid powder was obtained (yield 57%). Mp: 172-173° C. $^1$H NMR (400 MHz, DMSO-$d_6$, ppm): δ 13.30 (br, 1H), 12.05 (br, 1H), 8.84 (s, 1H), 8.02 (d, J=7.6 Hz, 1H), 7.91 (t, J=8.0 Hz, 2H), 7.66 (t, J=7.2 Hz, 1H), 7.55 (d, J=7.6 Hz, 1H), 7.51 (t, J=8 Hz, 1H), 7.44 (t, J=7.2 Hz, 1H), 7.38-7.34 (m, 2H). $^{13}$C NMR (100 MHz, DMSO-$d_6$, ppm): δ 167.92, 16.70, 147.26, 141.03, 134.55, 133.23, 131.94, 131.82, 131.06, 130.70, 130.34, 128.80, 128.74, 128.60, 127.22, 125.96, 109.26, 61.23, 14010. HRMS (ESI) calcd for $C_{19}H17N_3O_2SCl$ [M+H]$^+$ 386.0730, found 386.0731. HPLC purity: 98.88%, Retention time=16.14 min.

Propyl 2-formylbenzoate 2a

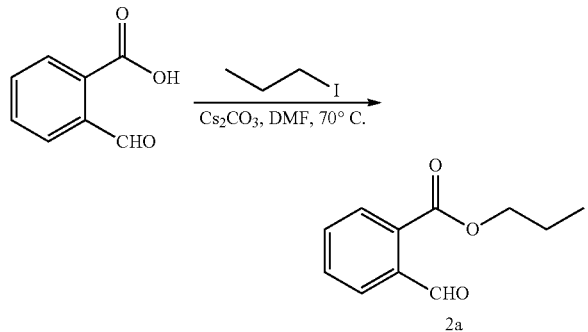

1.5 g of a transparent liquid (yield 78%) was obtained according to the same synthesis method as that for 1a. $^1$H NMR (400 MHz, DMSO-$d_6$, ppm): δ 10.40 (s, 1H), 7.93-7.90 (m, 1H), 7.88-7.84 (m, 1H), 7.81-7.77 (m, 2H), 4.29 (t, J=6.6 Hz, 2H), 1.74 (h, J=7.1 Hz, 2H), 0.97 (t, J=7.4 Hz, 3H). LC-MS (ESI) calcd for $C_{11}H_{12}O_3$ [M+H]$^+$ 193.08, found 193.10.

Isopropyl 2-formylbenzoate 3a

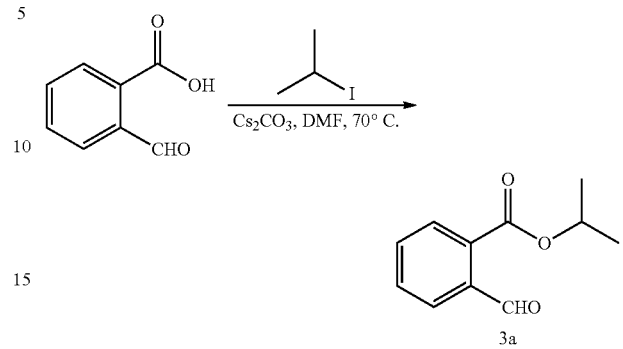

1.7 g of a yellow transparent liquid (yield 88%) was obtained according to the same synthesis method as that for 1a. $^1$H NMR (400 MHz, DMSO-$d_6$, ppm): δ 10.40 (s, 1H), 7.91-7.83 (m, 2H), 7.80-7.75 (m, 2H), 5.20 (hept, J=6.2 Hz, 1H), 1.35 (d, J=6.2 Hz, 6H). LC-MS (ESI) calcd for $C_{11}H_{12}O_3$ [M+H]$^+$ 193.08, found 193.10.

(E)-4-(2-chlorophenyl)-2-(2-propoxyformylbenzylidenehydrazino)thiazole A2

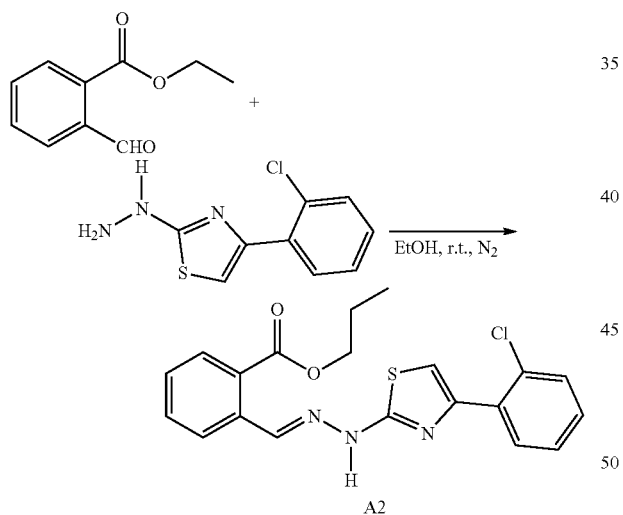

180 mg of a pale yellow solid powder (yield 58%) was obtained according to the same synthesis method as that for A1. Mp: 170-171° C. $^1$H NMR (400 MHz, DMSO-$d_6$, ppm): δ 12.40 (s, 1H), 8.71 (s, 1H), 8.00 (d, J=7.9 Hz, 1H), 7.88 (d, J=7.6, 2.4 Hz, 2H), 7.67 (t, J=7.6 Hz, 1H), 7.52 (q, J=7.9 Hz, 2H), 7.46-7.32 (m, 3H), 4.26 (t, J=6.5 Hz, 2H), 1.76 (h, J=7.1 Hz, 2H), 0.98 (t, J=7.3 Hz, 3H). $^{13}$C NMR (100 MHz, DMSO-$d_6$, ppm): δ 167.68, 167.03, 147.63, 140.16, 134.95, 133.6, 132.71, 131.53, 131.22, 130.85, 130.59, 129.52, 129.4, 129.38, 127.73, 126.74, 109.35, 67.06, 21.96, 10.87. HRMS (ESI) calcd for $C_{20}H_{18}N_3O_2SCl$ [M+H]$^+$ 400.0808, found 400.0888. HPLC purity: 96.95%, Retention time=12.44 min.

(E)-4-(2-chlorophenyl)-2-(2-isopropoxyformylbenzylidenehydrazino)thiazole A3

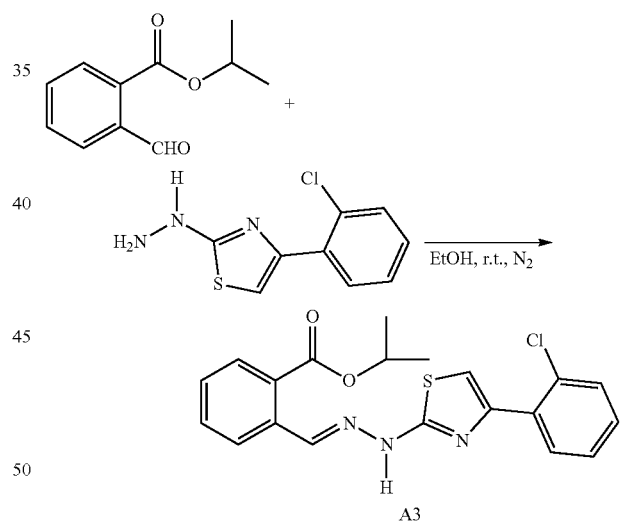

200 mg of a brown solid powder (yield 60%) was obtained according to the same synthesis method as that for A1. Mp: 159-160° C. $^1$H NMR (400 MHz, DMSO-$d_6$, ppm): δ 12.40 (s, 1H), 8.69 (s, 1H), 7.99 (d, J=7.8 Hz, 1H), 7.90-7.81 (m, 2H), 7.65 (t, J=7.6 Hz, 1H), 7.55-7.46 (m, 2H), 7.44-7.32 (m, 3H), 5.16 (hept, J=6.3 Hz, 1H), 1.35 (d, J=6.1 Hz, 6H). $^{13}$C NMR (100 MHz, DMSO-$d_6$, ppm): δ 205.55, 167.21, 166.04, 147.14, 139.59, 134.28, 133.20, 132.07, 131.02, 130.72, 130.35, 130.07, 129.35, 129.00, 128.84, 127.21, 126.11, 108.82, 68.85, 21.53. HRMS (ESI) calcd for $C_{20}H_{18}ClN_3O_2S$ [M+H]$^+$ 400.0808, found 400.0868. HPLC purity: 97.35%, Retention time=10.44 min.

Butyl 2-formylbenzoate 4a

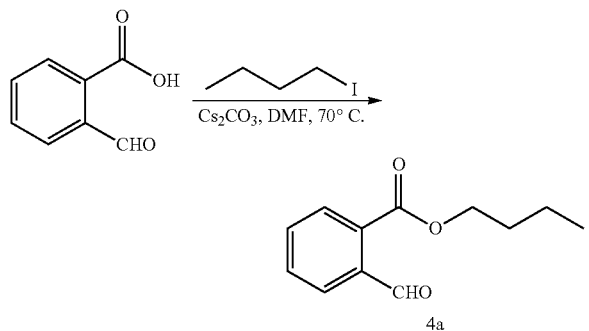

1.7 g of a yellow transparent liquid (yield 86%) was obtained according to the same synthesis method as that for 1a. $^1$H NMR (400 MHz, DMSO-$d_6$, ppm): δ 10.41 (s, 1H), 7.93-7.90 (m, 1H), 7.88-7.85 (m, 1H), 7.81-7.77 (m, 2H), 4.33 (t, J=6.5 Hz, 2H), 1.71 (p, J=8.5, 6.6 Hz, 2H), 1.42 (h, 2H), 0.94 (t, J=7.4 Hz, 3H). LC-MS (ESI) calcd for $C_{12}H_{14}O_3$ [M+H]$^+$ 207.09, found 207.10.

(E)-4-(2-chlorophenyl)-2-(2-butoxyformylbenzylidenehydrazino)thiazole A4

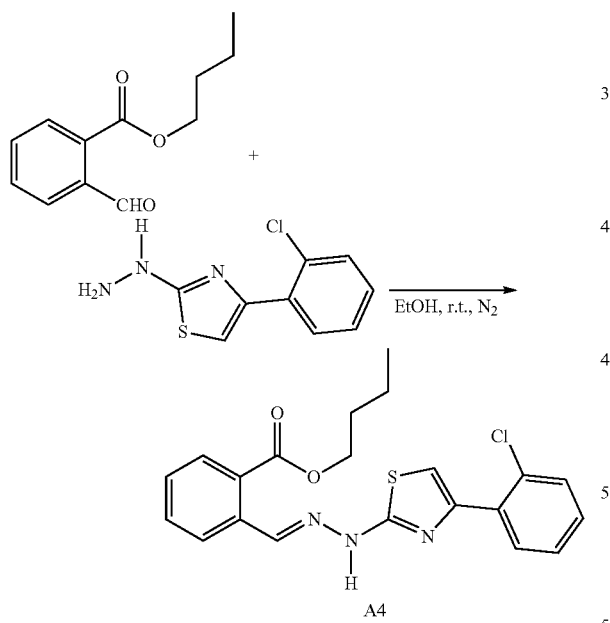

210 mg of a yellow powder (yield 55%) was obtained according to the same synthesis method as that for A1. Mp: 144-145° C. $^1$H NMR (400 MHz, DMSO-$d_6$, ppm): δ 12.40 (s, 1H), 8.71 (s, 1H), 8.00 (dd, J=8.0, 1.2 Hz, 1H), 7.89-7.84 (m, 2H), 7.67 (td, J=7.6, 1.3 Hz, 1H), 7.56-7.48 (m, 2H), 7.42 (td, J=7.5, 1.5 Hz, 1H), 7.39-7.33 (m, 2H), 4.30 (t, J=6.6 Hz, 2H), 1.72 (p, 2H), 1.42 (h, 2H), 0.94 (t, J=7.4 Hz, 3H). $^{13}$C NMR (100 MHz, DMSO-$d_6$, ppm): δ 167.68, 167.02, 147.63, 140.16, 134.95, 133.70, 132.70, 131.53, 131.22, 130.85, 130.58, 129.52, 129.40, 129.37, 127.73, 126.77, 109.35, 65.32, 30.57, 19.23, 14.09. HRMS (ESI) calcd for $C_{21}H_{20}N_3O_2SCl$ [M+H]$^+$ 414.0965, found 414.1044. HPLC purity: 97.15%, Retention time=11.23 min.

2-butyl 2-formylbenzoate 5a

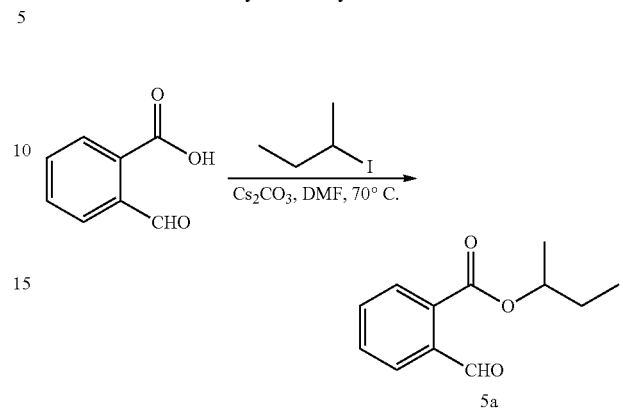

1.8 g of a transparent liquid (yield 91%) was obtained according to the same synthesis method as that for 1a. $^1$H NMR (400 MHz, DMSO-$d_6$, ppm): δ 10.39 (s, 1H), 7.91-7.88 (m, 1H), 7.87-7.84 (m, 1H), 7.81-7.76 (m, 2H), 5.06 (q, J=6.2 Hz, 1H), 1.75-1.64 (m, 2H), 1.32 (d, J=6.3 Hz, 3H), 0.93 (t, J=7.4 Hz, 3H). LC-MS (ESI) calcd for $C_{12}H_{14}O_3$ [M+H]$^+$ 207.09, found 207.10.

(E)-4-(2-chlorophenyl)-2-(2-(2-butoxy)formylbenzylidenehydrazino)thiazole A5

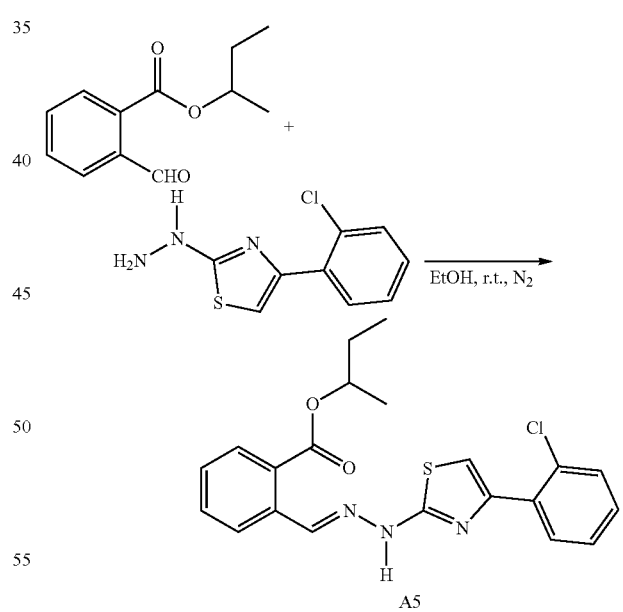

150 mg of a pale yellow powder (yield 52%) was obtained according to the same synthesis method as that for A1. Mp: 137-138° C. $^1$H NMR (400 MHz, DMSO-$d_6$, ppm): δ 12.41 (s, 1H), 8.71 (s, 1H), 8.00 (d, J=7.9, 1.2 Hz, 1H), 7.90-7.84 (m, 2H), 7.69-7.64 (m, 1H), 7.56-7.48 (m, 2H), 7.42 (td, J=7.5, 1.5 Hz, 1H), 7.39-7.33 (m, 2H), 5.03 (h, J=6.3 Hz, 1H), 1.77-1.63 (m, 2H), 1.33 (d, J=6.3 Hz, 3H), 0.93 (t, J=7.4 Hz, 3H). $^{13}$C NMR (100 MHz, DMSO-$d_6$, ppm): δ 167.71, 166.60, 147.64, 140.09, 134.89, 133.70, 132.64, 131.53, 131.22, 130.86, 130.52, 129.74, 129.52, 129.39, 127.73, 126.67, 109.35, 73.65, 28.66, 19.65, 10.07. HRMS (ESI) calcd for $C_{21}H_{20}N_3O_2SCl$ $[M+H]^+$ 414.0965, found 414.0988. HPLC purity: 98.05%, Retention time=11.14 min.

Amyl 2-formylbenzoate 6a

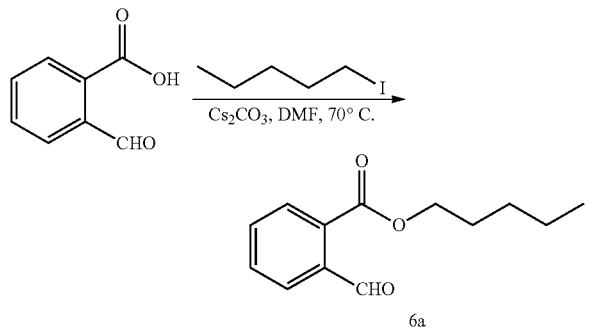

1.6 g of a transparent liquid (yield 77%) was obtained according to the same synthesis method as that for 1a. $^1$H NMR (400 MHz, DMSO-$d_6$, ppm): δ 10.40 (s, 1H), 7.93-7.89 (m, 1H), 7.88-7.84 (m, 1H), 7.81-7.77 (m, 2H), 4.32 (t, J=6.6 Hz, 2H), 1.72 (p, J=6.8 Hz, 2H), 1.42-1.30 (m, 4H), 0.92-0.87 (m, 3H). LC-MS (ESI) calcd for $C_{13}H_{16}O_3$ $[M+H]^+$ 221.11, found 221.10.

(E)-4-(2-chlorophenyl)-2-(2-pentyloxyformylbenzylidenehydrazino)thiazole A6

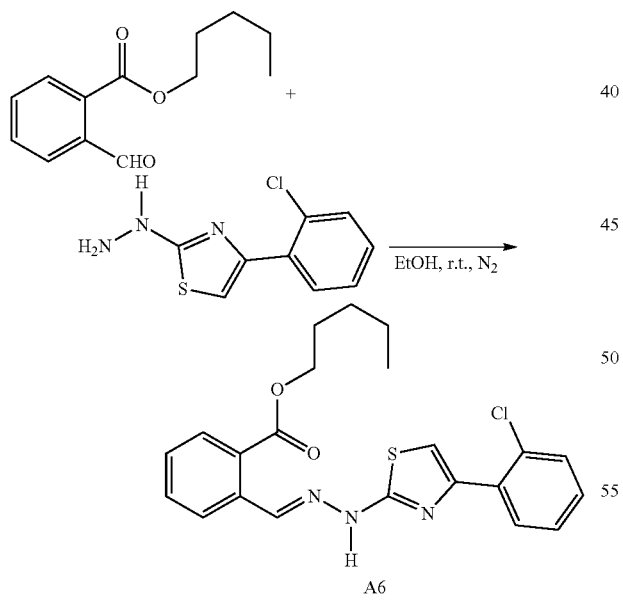

120 mg of a yellow powder (yield 52%) was obtained according to the same synthesis method as that for A1. Mp: 98-99° C. $^1$H NMR (400 MHz, DMSO-$d_6$, ppm): δ 12.39 (s, 1H), 8.71 (s, 1H), 7.99 (dd, J=8.0, 1.2 Hz, 1H), 7.86 (ddd, J=7.8, 6.1, 1.6 Hz, 2H), 7.66 (td, J=7.7, 1.4 Hz, 1H), 7.55-7.48 (m, 2H), 7.42 (td, J=7.5, 1.5 Hz, 1H), 7.38-7.33 (m, 2H), 4.29 (t, J=6.7 Hz, 2H), 1.74 (p, J=6.8 Hz, 2H), 1.42-1.30 (m, 4H), 0.89 (t, J=7.0 Hz, 3H). $^{13}$C NMR (100 MHz, DMSO-$d_6$, ppm): δ 167.68, 167.02, 147.63, 140.19, 134.95, 133.70, 132.69, 131.52, 131.22, 130.85, 130.57, 129.52, 129.40, 129.38, 127.73, 126.80, 109.33, 65.60, 28.21, 28.14, 22.29, 14.34. HRMS (ESI) calcd for $C_{22}H_{22}N_3O_2SCl$ $[M+H]^+$ 428.1121, found 428.1201. HPLC purity: 99.55%, Retention time=7.73 min.

Hexyl 2-formylbenzoate 7a

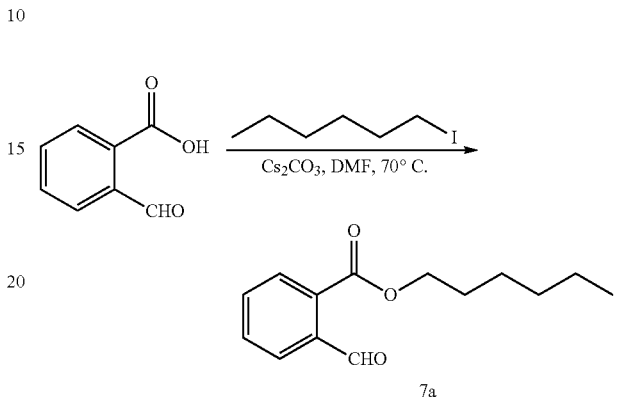

1.9 g of a transparent liquid (yield 81%) was obtained according to the same synthesis method as that for 1a. $^1$H NMR (400 MHz, DMSO-$d_6$, ppm): δ 10.40 (s, 1H), 7.93-7.88 (m, 1H), 7.88-7.83 (m, 1H), 7.82-7.76 (m, 2H), 4.32 (t, J=6.6 Hz, 2H), 1.71 (p, 2H), 1.43-1.25 (m, 6H), 0.90-0.83 (m, 3H). LC-MS (ESI) calcd for $C_{14}H_{18}O_3$ $[M+H]^+$ 235.13, found 235.10.

(E)-4-(2-chlorophenyl)-2-(2-hexyloxyformylbenzylidenehydrazino)thiazole A7

110 mg of a pale yellow powder (yield 59%) was obtained according to the same synthesis method as that for A1. Mp:

92-93° C. $^1$H NMR (400 MHz, DMSO-d$_6$, ppm): δ 12.45 (s, 1H), 8.76 (s, 1H), 8.05 (d, J=8.0 Hz, 1H), 7.96-7.87 (m, 2H), 7.72 (t, J=7.7 Hz, 1H), 7.62-7.53 (m, 2H), 7.51-7.37 (m, 3H), 4.34 (t, J=6.6 Hz, 2H), 1.79 (t, J=7.4 Hz, 2H), 1.49-1.28 (m, 6H), 0.92 (t, J=6.7 Hz, 3H). $^{13}$C NMR (100 MHz, DMSO-d$_6$, ppm): δ 167.56, 166.92, 147.53, 140.10, 134.85, 133.60, 132.56, 131.41, 131.12, 130.74, 130.44, 129.39, 129.30, 129.27, 127.60, 126.71, 109.20, 65.51, 31.27, 28.36, 25.52, 22.36, 14.22. HRMS (ESI) calcd for C$_{23}$H$_{24}$N$_3$O$_2$SCl [M+H]$^+$ 442.1278, found 442.1355. HPLC purity: 98.60%, Retention time=13.41 min.

Cyclohexyl 2-formylbenzoate 8a

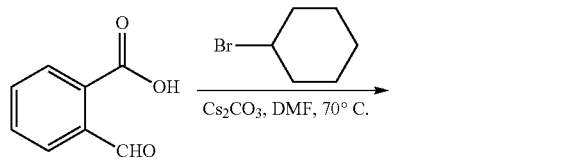

1.8 g of a pale yellow transparent liquid (yield 77%) was obtained according to the same synthesis method as that for 1a. $^1$H NMR (400 MHz, DMSO-d$_6$, ppm): δ 10.41 (s, 1H), 7.93-7.88 (m, 1H), 7.87-7.82 (m, 1H), 7.81-7.75 (m, 2H), 5.05-4.95 (m, 1H), 1.97-1.88 (m, 2H), 1.76-1.66 (m, 2H), 1.61-1.47 (m, 3H), 1.47-1.36 (m, 2H), 1.36-1.25 (m, 1H). LC-MS (ESI) calcd for C$_{14}$H$_{16}$O$_3$ [M+H]$^+$ 233.11, found 233.10.

(E)-4-(2-chlorophenyl)-2-(2-cyclohexyloxyformyl-benzylidenehydrazino)thiazole A8

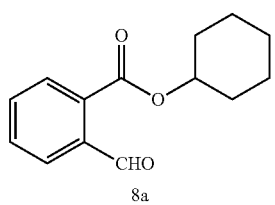

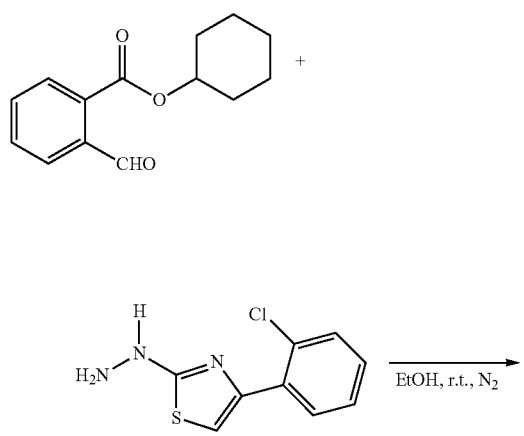

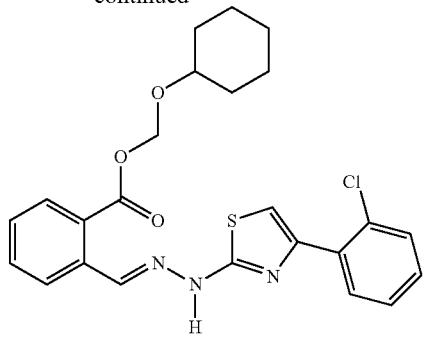

130 mg of a yellow powder (yield 50%) was obtained according to the same synthesis method as that for A1. Mp: 153-155° C. $^1$H NMR (400 MHz, DMSO-d$_6$, ppm): δ 12.42 (s, 1H), 8.70 (s, 1H), 8.00 (d, J=7.8 Hz, 1H), 7.90-7.83 (m, 2H), 7.66 (t, J=7.4 Hz, 1H), 7.56-7.47 (m, 2H), 7.42 (td, J=7.5, 1.2 Hz, 1H), 7.39-7.33 (m, 2H), 5.00-4.91 (m, 1H), 1.98-1.89 (m, 2H), 1.78-1.68 (m, 2H), 1.64-1.49 (m, 3H), 1.47-1.25 (m, 3H). $^{13}$C NMR (100 MHz, DMSO-d$_6$, ppm): δ 167.72, 166.37, 140.10, 134.84, 132.62, 131.52, 131.22, 130.86, 130.60, 129.80, 129.52, 129.39, 127.73, 126.67, 109.34, 73.85, 31.44, 25.34, 23.69. HRMS (ESI) calcd for C$_{23}$H$_{22}$N$_3$O$_2$SCl [M+H]$^+$ 440.1121, found 440.1101. HPLC purity: 98.03%, Retention time=13.03 min.

(Pivaloyloxy)methyl 2-formylbenzoate 9a

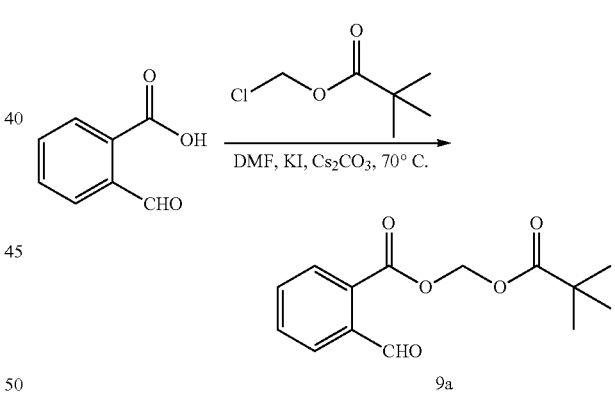

O-carboxybenzaldehyde (1 g, 6.7 mmol) was weighed into a 100 mL three-necked flask, cesium carbonate (4.3 g, 13.3 mmol), potassium iodide (1.1 g, 6.7 mmol) and 15 mL of N,N-dimethylformamide (DMF) were added, and chloromethyl pivalate (1.5 g, 10 mmol) was added under stirring. The reaction mixture was heated to 70° C. for 20 h. The reaction was monitored by TLC until the reaction was completed. The heating was stopped and 20 mL of water was added into the reaction flask. The reaction solution was extracted for three times with dichloromethane and water, and the organic layers were combined, dried over anhydrous sodium sulfate, and suction-filtered. The filtrate was purified through a silica-gel column to obtain a clear transparent liquid (0.9 g, yield 52%). LC-MS (ESI) calcd for C$_{14}$H$_{16}$O$_5$ [M+H]$^+$ 265.08, found 265.10.

(Pivaloyloxy)methyl (E)-2-((2-(4-(2-chlorophenyl)thiazol-2-yl)hydrazono)methyl)benzoate A9

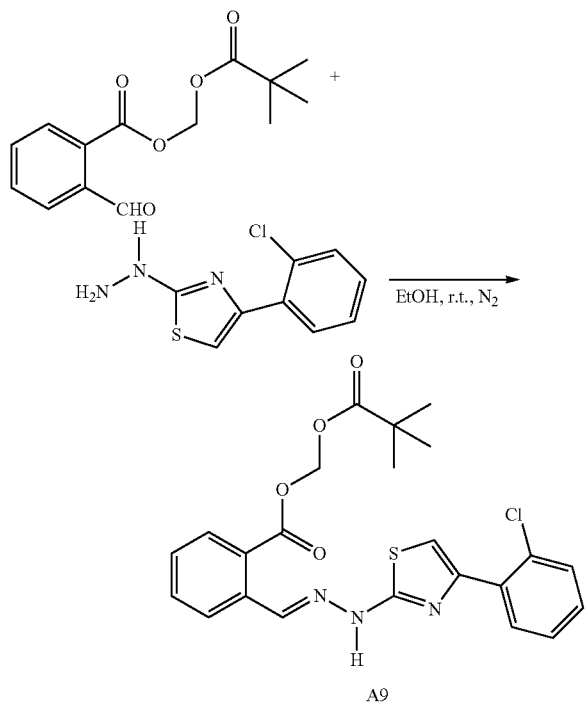

A crude product was obtained according to the same synthesis method as that for A1. Afterwards, a pale yellow powder was obtained through solid precipitation by adding another solvent (the crude product was completely dissolved in an appropriate amount of ethyl acetate, petroleum ether was added with electromagnetic-stirring and rapidly stirred, and solids were precipitated and suction-filtered). (180 mg, yield 49%). Mp: 114-115° C. $^1$H NMR (400 MHz, DMSO-d$_6$, ppm): δ 12.43 (s, 1H), 8.73 (s, 1H), 8.03 (d, J=8.0, 1.2 Hz, 1H), 7.89-7.83 (m, 2H), 7.74-7.68 (m, 1H), 7.56-7.51 (m, 2H), 7.42 (td, J=7.5, 1.4 Hz, 1H), 7.39-7.33 (m, 2H), 5.98 (s, 2H), 1.18 (s, 9H). $^{13}$C NMR (100 MHz, DMSO-d$_6$, ppm): δ 167.13, 164.91, 139.23, 135.19, 133.04, 131.04, 130.73, 130.35, 130.31, 129.04, 129.02, 127.24, 127.06, 126.51, 108.96, 80.13, 38.26, 26.47. HRMS (ESI) calcd for C$_{23}$H$_{22}$N$_3$O$_4$SCl [M+H]$^+$ 472.1020, found 472.1096. HPLC purity: 97.79%, Retention time=9.68 min.

((isopropoxycarbonyl)oxy)methyl 2-formylbenzoate 10a

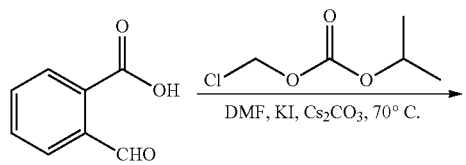

0.8 g of a colorless transparent liquid (yield 45%) was obtained according to the same synthesis method as that for 9a. LC-MS (ESI) calcd for C$_{13}$H$_{14}$O$_6$ [M+NH$_4$]$^+$ 284.08, found 284.10.

((isopropoxycarbonyl)oxy)methyl (E)-2-((2-(4-(2-chlorophenyl)thiazol-2-yl)hydrazono)methyl)benzoate A10

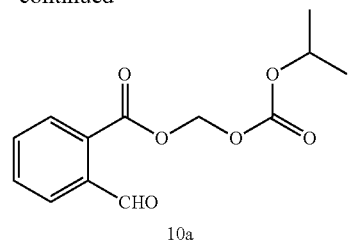

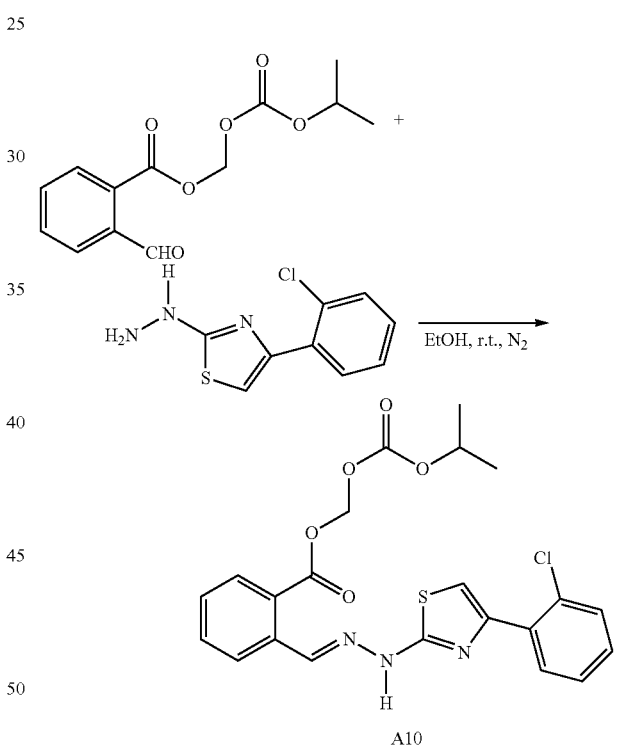

160 mg of a yellow powder (yield 53%) was obtained according to the same synthesis method as that for A9. Mp: 110-111° C. $^1$H NMR (400 MHz, DMSO-d$_6$, ppm): δ 12.44 (s, 1H), 8.76 (s, 1H), 8.04 (d, J=8.0, 1.2 Hz, 1H), 7.93-7.85 (m, 2H), 7.73 (t, J=7.6, 1.3 Hz, 1H), 7.57-7.51 (m, 2H), 7.43 (td, J=7.5, 1.5 Hz, 1H), 7.40-7.33 (m, 2H), 5.96 (s, 2H), 4.85 (hept, J=6.2 Hz, 1H), 1.26 (d, J=6.2 Hz, 6H). $^{13}$C NMR (100 MHz, DMSO-d$_6$, ppm): δ 167.62, 165.32, 153.25, 147.67, 139.76, 135.83, 133.66, 131.54, 131.23, 131.01, 130.85, 129.54, 129.49, 127.74, 127.30, 126.99, 109.47, 83.02, 73.24, 21.80. HRMS (ESI) calcd for C$_{22}$H$_{20}$N$_3$O$_5$SCl [M+H]$^+$ 474.0812, found 474.0889. HPLC purity: 99.25%, Retention time=12.74 min.

Benzoyl 2-formylbenzoate 11a

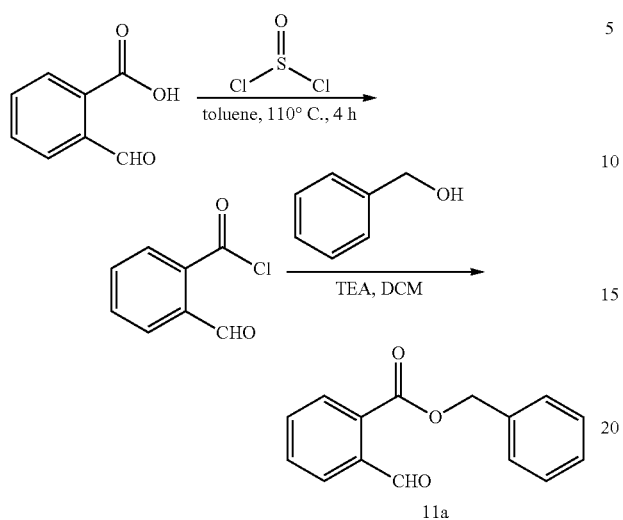

o-carboxybenzaldehyde (1.5 g, 10 mmol) was weighed into a 100 mL three-necked flask B, and 20 mL of anhydrous toluene was added. In an ice bath, thionyl chloride (1.79 g, 15 mmol) was added with electromagnetic-stirring. After 15 minutes, the ice bath was removed, and the three-necked flask B was transferred to an oil bath and heat to reflux at 110° C. for 4 h. The heating was stopped, and the solvent was removed in vacuo to obtain a yellow viscous liquid, which was directly diluted with 10 mL of anhydrous dichloromethane. Benzyl alcohol (1.08 g, 10 mmol), triethylamine (1.52 g, 15 mmol), 15 mL of anhydrous dichloromethane were added into another 100 mL single-mouth reaction flask A and electromagnetic-stirred in an ice salt bath for 15 minutes. An acid chloride solution in dichloromethane was added dropwise to the single-mouth reaction flask A for 30 minutes in an ice bath. Afterwards, the reaction system was warmed to room temperature, and the reaction was detected by TLC. After the reaction was completed, water was added to the reaction solution and stirred for 10 minutes, and the mixture was allowed to stratification. The organic phase was taken, and the aqueous phase was extracted for three times with dichloromethane. Organic phases were combined, dried, evaporated to dryness, and purified through a column, so as to give a colorless transparent liquid (1.1 g, yield 46%). $^1$H NMR (400 MHz, DMSO-$d_6$, ppm): δ 10.42 (s, 1H), 7.95-7.91 (m, 2H), 7.78-7.75 (m, 2H), 7.50-7.48 (m, 2H), 7.42-7.36 (m, 3H), 5.39 (s, 2H). LC-MS (ESI) calcd for $C_{15}H_{12}O_3$ [M+H]$^+$ 241.08, found 241.10.

(E)-4-(2-chlorophenyl)-2-(2-benzyloxyformylbenzylidenehydrazino)thiazole A11

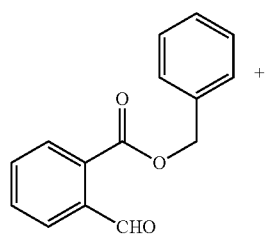

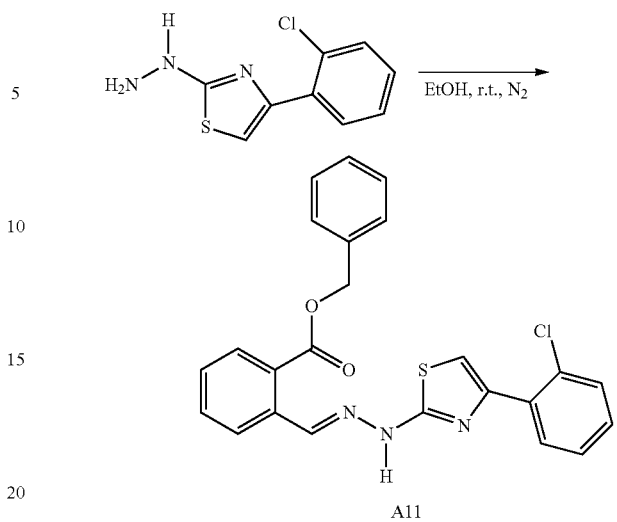

80 mg of a brown powder (yield 46%) was obtained according to the same synthesis method as that for A1. Mp: 168-169° C. $^1$H NMR (400 MHz, DMSO-$d_6$, ppm): δ 12.41 (s, 1H), 8.78 (s, 1H), 8.02 (d, J=7.9 Hz, 1H), 7.92-7.86 (m, 2H), 7.70-7.65 (m, 1H), 7.56-7.49 (m, 4H), 7.45-7.40 (m, 3H), 7.39-7.34 (m, 3H), 5.38 (s, 2H). $^{13}$C NMR (100 MHz, DMSO-$d_6$, ppm): δ 166.20, 147.14, 139.61, 135.86, 134.72, 133.20, 132.41, 131.04, 130.73, 130.35, 130.21, 129.01, 128.92, 128.51, 128.37, 128.16, 128.08, 127.22, 126.35, 108.87, 66.59. HRMS (ESI) calcd for $C_{24}H_{18}N_3O_2SCl$ [M+H]$^+$ 448.0808, found 448.0888. HPLC purity: 98.45%, Retention time=12.14 min.

Phenylethyl 2-formylbenzoate 12a

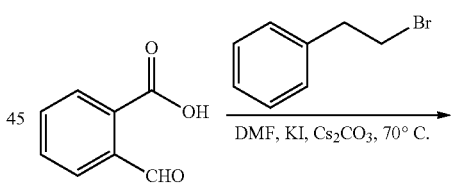

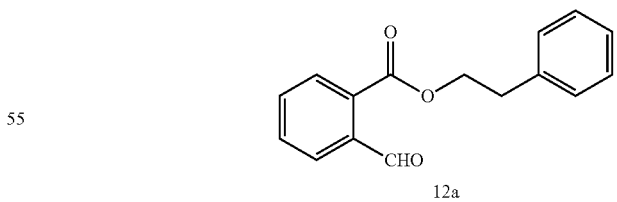

2.5 g of a transparent liquid (yield 70%) was obtained according to the same synthesis method as that for 9a. $^1$H NMR (400 MHz, DMSO-$d_6$, ppm): δ 10.31 (s, 1H), 7.86-7.81 (m, 2H), 7.79-7.74 (m, 2H), 7.32 (d, J=4.4 Hz, 4H), 7.27-7.20 (m, 1H), 4.56 (t, J=6.7 Hz, 2H), 3.06 (t, J=6.7 Hz, 2H). LC-MS (ESI) calcd for $C_{16}H_{14}O_3$ [M+H]$^+$ 255.09, found 255.10.

(E)-4-(2-chlorophenyl)-2-(2-phenylethoxyformyl-benzylidenehydrazino)thiazole A12

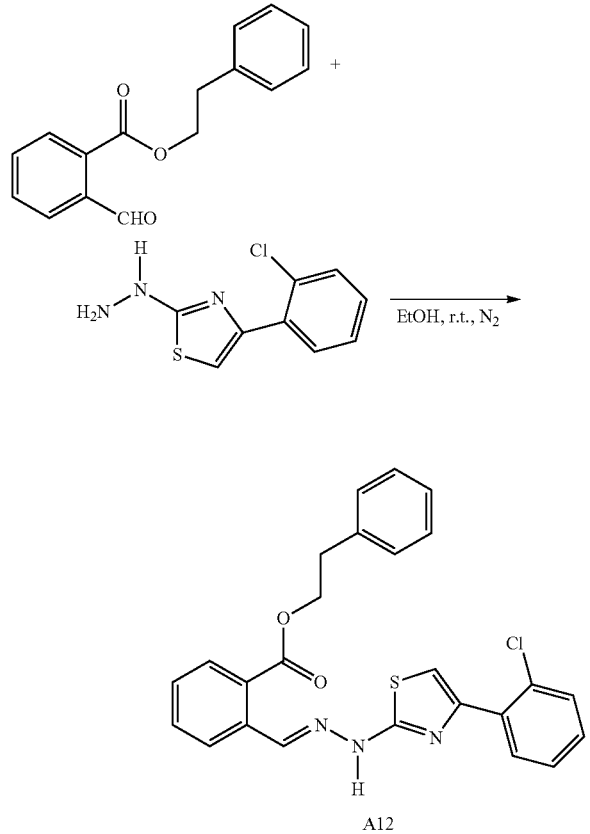

110 mg of a yellow powder (yield 51%) was obtained according to the same synthesis method as that for A1. Mp: 116-118° C. $^1$H NMR (400 MHz, DMSO-d$_6$, ppm): δ 12.46 (s, 1H), 8.79 (s, 1H), 8.05 (d, J=7.9 Hz, 1H), 7.94 (d, J=7.7 Hz, 1H), 7.84 (d, J=7.8 Hz, 1H), 7.71 (t, J=7.7 Hz, 1H), 7.60 (d, J=7.9 Hz, 1H), 7.54 (t, J=7.6 Hz, 1H), 7.48 (t, J=7.6 Hz, 1H), 7.46-7.34 (m, 6H), 7.32-7.25 (m, 1H), 4.57 (t, J=6.8 Hz, 2H), 3.14 (t, J=6.9 Hz, 2H). $^{13}$C NMR (100 MHz, DMSO-d$_6$, ppm): δ 167.58, 166.74, 147.55, 140.03, 138.30, 134.93, 133.61, 132.66, 131.43, 131.13, 130.75, 130.45, 129.41, 129.24, 129.03, 128.78, 127.62, 126.80, 126.67, 109.25, 65.98, 34.61. HRMS (ESI) calcd for C$_{25}$H$_{20}$N$_3$O$_2$SCl [M+H]$^+$ 462.0965, found 462.1041. HPLC purity: 98.60%, Retention time=12.24 min.

2-formylbenzoyl(N,N-dimethyl)amine 13a

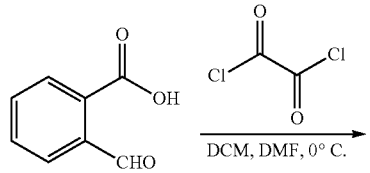

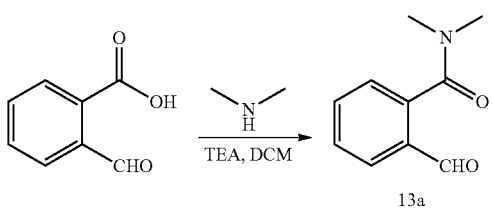

o-carboxybenzaldehyde (1.5 g, 10 mmol) was weighed into a 100 mL three-necked flask, and 30 mL of anhydrous dichloromethane was added. 4 drops of anhydrous DMF were added into the flask in an ice salt bath. Thionyl chloride (1.9 g, 15 mmol) was added with electromagnetic-stirring. After 30 minutes, the ice bath was removed, and the flask was warmed to room temperature for 2 h, and the reaction was detected by TLC. After the reaction was completed, the solvent was removed in vacuo to obtain a yellow viscous liquid, which was directly diluted with 10 mL of anhydrous dichloromethane. Dimethylamine (0.45 g, 10 mmol), triethylamine (1.52 g, 15 mmol), 10 mL of anhydrous dichloromethane were added into another 100 mL single-mouth reaction flask and electromagnetic-stirred in an ice salt bath for 15 minutes. A freshly prepared acid chloride solution in dichloromethane was added dropwise through a constant pressure dropping funnel into the reaction flask for 30 minutes in an ice bath. Afterwards, the reaction system was warmed to room temperature, and the reaction was detected by TLC. After the reaction was completed, water was added to the reaction solution and stirred for 10 minutes, and the mixture was allowed to stratification. The organic phase was taken, and the aqueous phase was extracted for three times with dichloromethane. Organic phases were combined, dried, evaporated to dryness, and purified through a column, so as to give a colorless transparent liquid (0.5 g, yield 26%). $^1$H NMR (400 MHz, DMSO-d$_6$, ppm): δ 9.97 (s, 1H), 7.98-7.94 (m, 1H), 7.75 (td, J=7.5, 1.4 Hz, 1H), 7.67-7.61 (m, 1H), 7.44-7.39 (m, 1H), 3.03 (s, 3H), 2.72 (s, 3H). LC-MS (ESI) calcd for C$_{10}$H$_{11}$NO$_2$ [M+H]$^+$ 178.08, found 178.10.

(E)-4-(2-chlorophenyl)-2-((N,N-Dimethyl)formyl-benzylidenehydrazino)thiazole A13

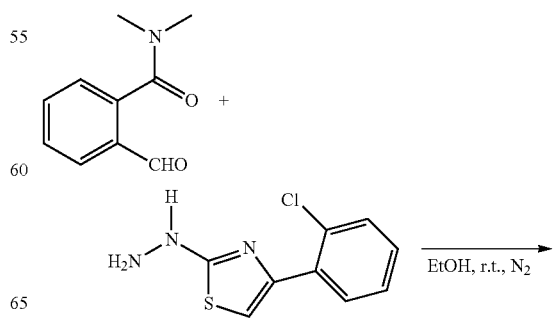

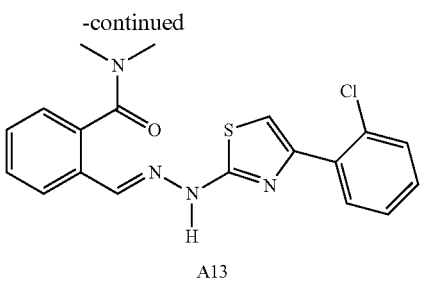

A13

80 mg of a yellow powder (yield 31%) was obtained according to the same synthesis method as that for A1. Mp: 181-182° C. $^1$H NMR (400 MHz, DMSO-d$_6$, ppm): δ 12.25 (s, 1H), 8.07 (s, 1H), 7.94-7.89 (m, 2H), 7.61-7.58 (m, 1H), 7.57-7.53 (m, 1H), 7.52-7.46 (m, 2H), 7.44-7.40 (m, 2H), 7.37-7.32 (m, 1H), 3.13 (s, 3H), 2.85 (s, 3H). $^{13}$C NMR (100 MHz, DMSO-d$_6$, ppm): δ 169.33, 167.36, 147.51, 139.24, 136.34, 133.59, 131.42, 131.12, 130.92, 130.74, 129.47, 129.41, 129.32, 127.61, 127.19, 126.02, 109.19, 38.50, 34.64. HRMS (ESI) calcd for C$_{19}$H$_{17}$N$_4$OSCl [M+H]$^+$ 385.0812, found 385.0802. HPLC purity: 96.13%, Retention time=4.18 min.

Synthesis of Prodrug of B Series 2-methylthiosemicarbazide 4

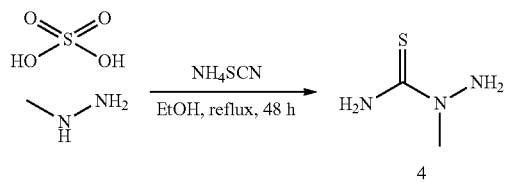

Methyl hydrazine sulfate (12.5 g, 86.5 mmol) was weighed into a 500 ml three-mouth flask, 350 ml of anhydrous ethanol was added, and ammonium thiocyanate (8 g, 104.0 mmol) of was added with electromagnetic-stirring. The reaction mixture was heated to reflux, and detected by TLC for 48 h. The reaction was stopped, cooled to room temperature and suction-filtered. The obtained filtrate was evaporated to dryness and separated through silica gel column chromatography (DCM:MeOH=100:1 v/v) to give white powdery solids (2.2 g, yield 24%). $^1$H NMR (400 MHz, DMSO-d$_6$, ppm): δ 7.38 (s, 2H), 4.88 (s, 2H), 3.40 (s, 3H). LC-MS (ESI) calcd for C$_2$H$_7$N$_3$S [M+H]$^+$ 106.04, found 106.10.

2-methyl-1-(2-carboxybenzylidene)thiosemicarbazide 5

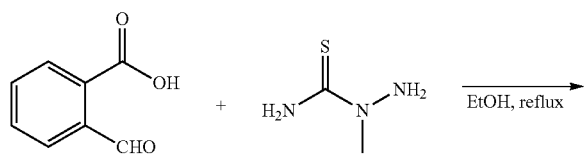

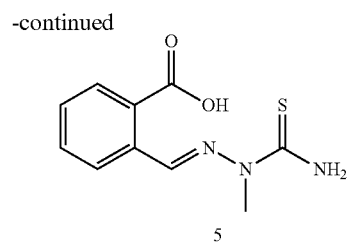

Compound 4 (600 mg, 5.7 mmol) was weighed into a 250 mL three-necked flask, 150 mL of absolute ethanol was added, o-formylbenzoic acid (855 mg, 5.7 mmol) was added with electromagnetic-stirring, heated to reflux, and the reaction was monitored by TLC. After 4 h, the reaction was completed, the heating was stopped, and the reaction solution was cooled to room temperature. The solvent was evaporated to dryness in vacuo and purified through silica gel column chromatography (DCM:MeOH=100:1, v/v) to obtain white powdery solids (700 mg, yield 51.9%). $^1$H NMR (400 MHz, DMSO-d$_6$, ppm): δ 13.32 (br, 1H), 8.54 (s, 1H), 8.50 (s, 1H), 8.33 (d, J=7.6 Hz, 1H), 8.24 (s, 1H), 7.90 (d, J=7.8 Hz, 1H), 7.60 (t, J=7.2 Hz, 1H), 7.52 (t, J=7.2 Hz, 1H), 3.75 (s, 3H). LC-MS (ESI) calcd for C$_2$H$_7$N$_3$S [M+H]$^+$ 238.06, found 238.10.

(E)-4-(2-chlorophenyl)-2-[1-methyl-2-(2-carboxy-benzylidene)hydrazino]thiazole B

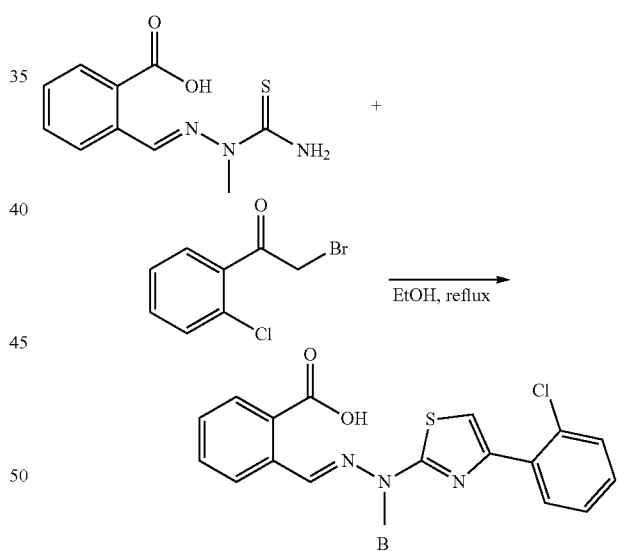

Compound 5 (700 mg, 2.94 mmol) was weighed into a 250 mL three-necked flask, 80 mL of absolute ethanol was added, and 2-bromo-2'-chloroacetophenone (0.46 mL, 2.94 mmol) was added with electromagnetic-stirring, and heated to reflux. The reaction was detected by TLC. After 4 h, the reaction was completed. The heating was stopped and the reaction mixture was cooled to room temperature. The solvent was evaporated to dryness in vacuo and purified through silica gel column chromatography (DCM:MeOH=100:1, v/v) to give 540 mg of yellow powdery solids (yield 49%). Mp: 210-211° C. $^1$H NMR (400 MHz, DMSO-d$_6$, ppm): δ 13.26 (s, 1H), 8.60 (s, 1H), 8.04 (d, J=7.6 Hz, 1H), 7.97-7.89 (m, 2H), 7.64 (t, J=7.8 Hz, 1H), 7.55-7.48

(m, 2H), 7.46 (s, 1H), 7.40 (td, $J_1$=7.6 Hz, $J_2$=1.2 Hz, 1H), 7.32 (td, $J_1$=7.6 Hz, $J_2$=1.6 Hz, 1H), 3.65 (s, 3H). $^{13}$C NMR (100 MHz, DMSO-$d_6$, ppm): δ 168.96, 168.50, 147.22, 136.91, 135.21, 133.40, 132.46, 131.50, 131.02, 130.88, 130.55, 130.14, 129.46, 129.18, 127.62, 126.50, 111.43, 32.90. HRMS (ESI) calcd for $C_{18}H_{15}ClN_3O_2S$ [M+H]$^+$ 372.0574, found 372.0573. HPLC purity: 98.15%, Retention time=9.46 min.

(E)-4-(2-chlorophenyl)-2-[1-methyl-2-(2-ethoxy-formylbenzylidene)hydrazino]thiazole B1

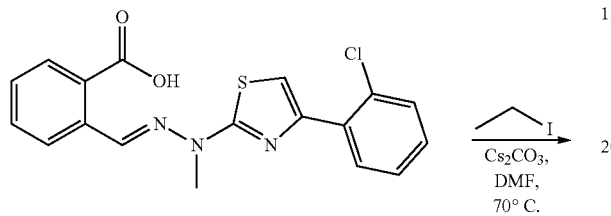

Compound B (0.2 g, 0.54 mmol) was weighed into a 50 mL two-necked flask, cesium carbonate (0.35 g, 1.08 mmol) and 10 mL of N,N-dimethylformamide (DMF) were added, and iodoethane (0.18 g, 1.08 mmol) was added with electromagnetic-stirring. The reaction was heated to 70° C., and detected by TLC during the reaction. After 5 hr, the reaction was completed. The heating was stopped, and 20 mL of water was added to the reaction flask. The reaction solution was extracted with dichloromethane (DCM), and allowed to stand for separating the organic phase. The aqueous phase was extracted for three times with dichloromethane. Organic phases were combined and dried. The solvent was evaporated to dryness in vacuo and purified through column chromatography to give yellow powdery solids (120 mg, yield 58%). Mp: 109-110° C. $^1$H NMR (400 MHz, DMSO-$d_6$, ppm): δ 8.49 (s, 1H), 8.02 (d, J=8.1, 1.2 Hz, 1H), 7.96 (dd, J=7.7, 1.8 Hz, 1H), 7.92-7.88 (m, 1H), 7.69 (t, J=7.6, 1.4 Hz, 1H), 7.56-7.47 (m, 3H), 7.45-7.40 (m, 1H), 7.37 (td, J=7.6, 1.8 Hz, 1H), 4.36 (q, J=7.1 Hz, 2H), 3.69 (s, 3H), 1.35 (t, J=7.1 Hz, 3H). $^{13}$C NMR (100 MHz, DMSO-$d_6$, ppm): δ 168.51, 166.58, 146.72, 136.19, 134.55, 133.00, 132.32, 131.12, 130.69, 130.36, 130.36, 129.08, 129.06, 128.88, 127.25, 126.36, 111.10, 61.16, 32.55, 14.04. HRMS (ESI) calcd for $C_{20}H_{18}N_3O_2SCl$ [M+H]$^+$ 400.0808, found 400.0886. HPLC purity: 98.65%, Retention time=16.44 min.

(E)-4-(2-chlorophenyl)-2-[1-methyl-2-(2-propoxy-formylbenzylidene)hydrazino]thiazole B2

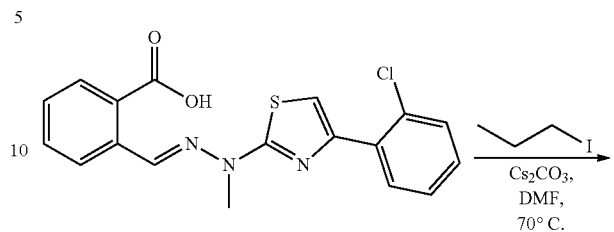

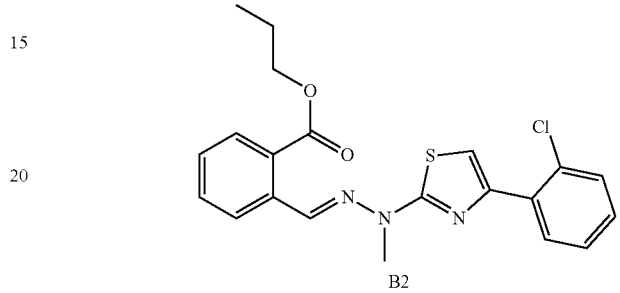

100 mg of yellow powdery solids (yield 51%) was obtained according to the same synthesis method as that for B1. Mp: 96-97° C. $^1$H NMR (400 MHz, DMSO-$d_6$, ppm): δ 8.49 (s, 1H), 8.02 (d, J=8.0, 1.2 Hz, 1H), 7.96 (dd, J=7.7, 1.9 Hz, 1H), 7.91 (dd, J=7.9, 1.4 Hz, 1H), 7.72-7.67 (m, 1H), 7.57-7.46 (m, 3H), 7.43 (td, J=7.5, 1.4 Hz, 1H), 7.37 (td, J=7.6, 1.8 Hz, 1H), 4.27 (t, J=6.6 Hz, 2H), 3.68 (s, 3H), 1.75 (h, J=7.1 Hz, 2H), 0.98 (t, J=7.4 Hz, 3H). $^{13}$C NMR (100 MHz, DMSO-$d_6$, ppm): δ 169.00, 167.14, 147.22, 136.65, 135.11, 133.49, 132.84, 131.62, 131.19, 130.87, 130.81, 129.59, 129.53, 129.42, 127.76, 126.94, 111.61, 67.09, 33.05, 21.99, 10.89. HRMS (ESI) calcd for $C_{21}H_{20}N_3O_2SCl$ [M+H]$^+$ 414.0965, found 414.1042. HPLC purity: 99.75%, Retention time=15.44 min.

(E)-4-(2-chlorophenyl)-2-[1-methyl-2-(2-iso-propoxyformylbenzylidene)hydrazino]thiazole B3

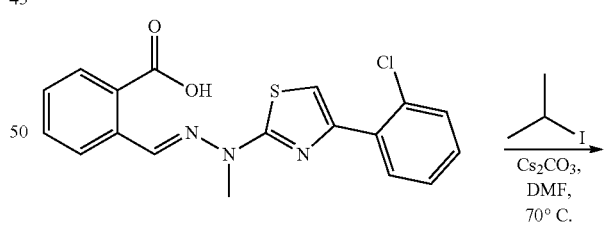

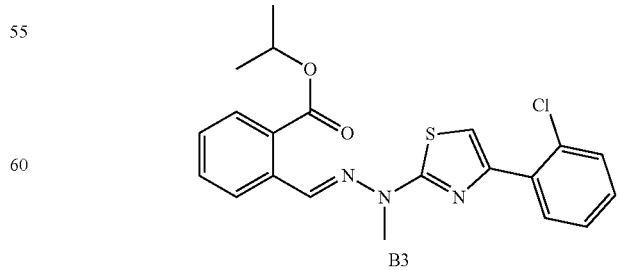

140 mg of pale yellow powder (yield 57%) was obtained according to the same synthesis method as that for B1. Mp:

128-130° C. $^1$H NMR (400 MHz, DMSO-d$_6$, ppm): δ 8.48 (s, 1H), 8.02 (d, J=8.0, 1.2 Hz, 1H), 7.96 (dd, J=7.7, 1.8 Hz, 1H), 7.88 (d, J=7.8, 1.4 Hz, 1H), 7.71-7.65 (m, 1H), 7.56-7.47 (m, 3H), 7.46-7.39 (m, 1H), 7.36 (td, J=7.6, 1.8 Hz, 1H), 5.21 (hept, J=6.3 Hz, 1H), 3.69 (s, 3H), 1.36 (d, J=6.2 Hz, 6H). $^{13}$C NMR (100 MHz, DMSO-d$_6$, ppm): δ 168.52, 166.09, 146.73, 136.11, 134.45, 133.01, 132.24, 131.12, 130.70, 130.36, 129.43, 129.08, 128.87, 127.25, 126.27, 111.10, 68.75, 32.54, 21.59. HRMS (ESI) calcd for C$_{21}$H$_{20}$N$_3$O$_2$SCl [M+H]$^+$ 414.0965, found 414.0955. HPLC purity: 99.65%, Retention time=12.44 min.

(E)-4-(2-chlorophenyl)-2-[1-methyl-2-(2-butoxy-formylbenzylidene)hydrazino]thiazole B4

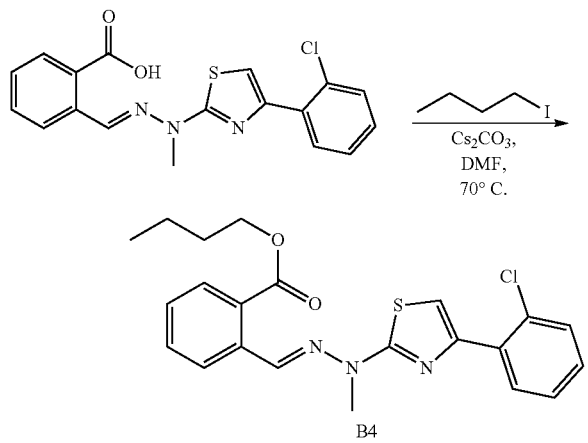

190 mg of yellow powdery solids (yield 61%) was obtained according to the same synthesis method as that for B1. Mp: 135-136° C. $^1$H NMR (400 MHz, DMSO-d$_6$, ppm): δ 8.49 (s, 1H), 8.01 (d, J=7.9, 1.2 Hz, 1H), 7.96 (dd, J=7.7, 1.8 Hz, 1H), 7.90 (dd, J=7.8, 1.3 Hz, 1H), 7.72-7.66 (m, 1H), 7.56-7.46 (m, 3H), 7.43 (td, J=7.5, 1.4 Hz, 1H), 7.36 (td, J=7.6, 1.9 Hz, 1H), 4.31 (t, J=6.6 Hz, 2H), 3.68 (s, 3H), 1.71 (p, 2H), 1.42 (h, 2H), 0.93 (t, J=7.4 Hz, 3H). $^{13}$C NMR (100 MHz, DMSO-d$_6$, ppm): δ 168.98, 167.14, 147.21, 136.62, 135.11, 133.49, 132.81, 131.62, 131.18, 130.86, 130.80, 129.58, 129.50, 129.40, 127.75, 126.95, 111.60, 65.33, 33.03, 30.60, 19.26, 14.06. HRMS (ESI) calcd for C$_{22}$H$_{22}$N$_3$O$_2$SCl [M+H]$^+$ 428.1121, found 428.1131. HPLC purity: 98.65%, Retention time=20.44 min.

(E)-4-(2-chlorophenyl)-2-[1-methyl-2-(2-(2-butoxy)formylbenzylidene)hydrazino]thiazole B5

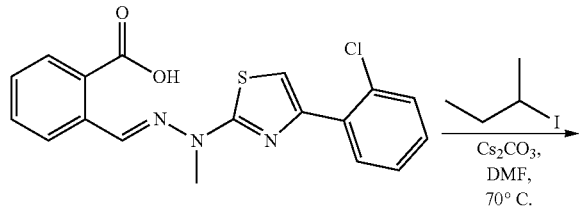

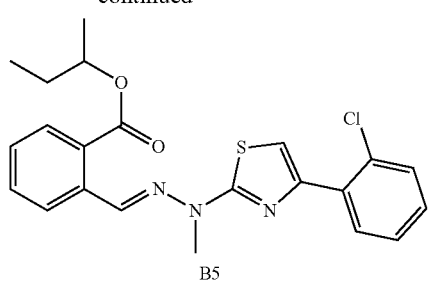

160 mg of pale yellow powder (yield 56%) was obtained according to the same synthesis method as that for B1. Mp: 131-132° C. $^1$H NMR (400 MHz, DMSO-d$_6$, ppm): δ 8.49 (s, 1H), 8.02 (dd, J=8.0, 1.2 Hz, 1H), 7.96 (dd, J=7.7, 1.8 Hz, 1H), 7.90 (dd, J=7.8, 1.4 Hz, 1H), 7.72-7.66 (m, 1H), 7.56-7.46 (m, 3H), 7.43 (td, J=7.5, 1.4 Hz, 1H), 7.37 (td, J=7.6, 1.9 Hz, 1H), 5.06 (h, J=6.3 Hz, 1H), 3.69 (s, 3H), 1.76-1.62 (m, 2H), 1.33 (d, J=6.3 Hz, 3H), 0.93 (t, J=7.5 Hz, 3H). $^{13}$C NMR (100 MHz, DMSO-d$_6$, ppm): δ 169.02, 166.68, 147.22, 136.57, 135.04, 133.49, 132.80, 131.62, 131.19, 130.87, 130.79, 129.81, 129.60, 129.43, 127.76, 126.84, 111.62, 73.57, 33.04, 28.71, 19.66, 10.04. HRMS (ESI) calcd for C$_{22}$H$_{22}$N$_3$O$_2$SCl [M+H]$^+$ 428.1121, found 428.1131. HPLC purity: 98.95%, Retention time=11.42 min.

(E)-4-(2-chlorophenyl)-2-[1-methyl-2-(2-pentyloxy-formylbenzylidene)hydrazino]thiazole B6

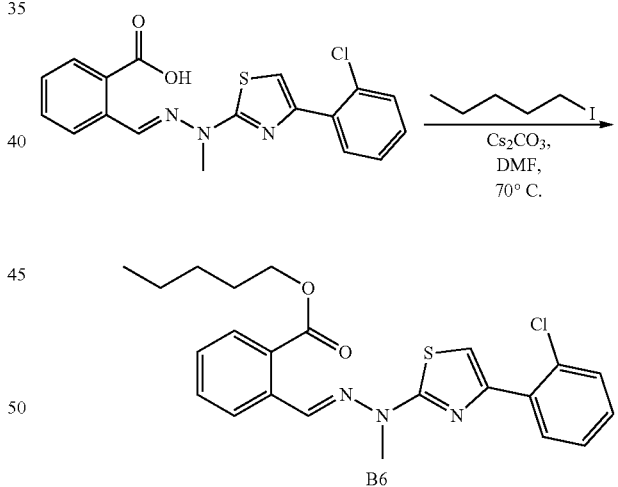

130 mg of pale yellow powder (yield 55%) was obtained according to the same synthesis method as that for B1. Mp: 117-118° C. $^1$H NMR (400 MHz, DMSO-d$_6$, ppm): δ 8.48 (s, 1H), 8.04-7.85 (m, 3H), 7.69 (t, J=7.6 Hz, 1H), 7.59-7.31 (m, 5H), 4.30 (t, J=6.5 Hz, 2H), 3.68 (s, 3H), 1.78-1.64 (m, 2H), 1.35 (s, 4H), 0.88 (t, J=6.7 Hz, 3H). $^{13}$C NMR (100 MHz, DMSO-d$_6$, ppm): δ 168.99, 167.18, 147.22, 136.69, 135.08, 133.50, 132.80, 131.62, 131.19, 130.87, 130.77, 129.60, 129.57, 129.42, 127.76, 127.01, 111.60, 65.64, 33.05, 28.26, 28.19, 22.28, 14.33. HRMS (ESI) calcd for C$_{23}$H$_{24}$N$_3$O$_2$SCl [M+H]$^+$ 442.1278, found 442.1265. HPLC purity: 98.21%, Retention time=22.10 min.

(E)-4-(2-chlorophenyl)-2-[1-methyl-2-(2-hexyloxy-formylbenzylidene)hydrazino]thiazole B7

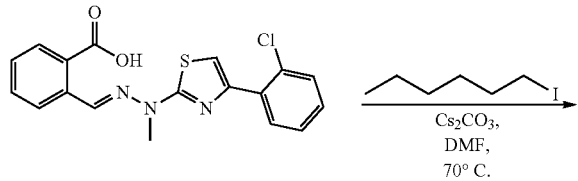

170 mg of pale yellow powder (yield 49%) was obtained according to the same synthesis method as that for B1. Mp: 88-89° C. $^1$H NMR (400 MHz, DMSO-d$_6$, ppm): δ 8.48 (s, 1H), 8.02-7.94 (m, 2H), 7.88 (dd, J=7.8, 1.3 Hz, 1H), 7.72-7.66 (m, 1H), 7.58-7.46 (m, 3H), 7.43 (td, J=7.6, 1.4 Hz, 1H), 7.36 (td, J=7.6, 1.9 Hz, 1H), 4.30 (t, J=6.6 Hz, 2H), 3.68 (s, 3H), 1.75-1.66 (m, 2H), 1.41-1.25 (m, 6H), 0.88-0.82 (m, 3H). $^{13}$C NMR (100 MHz, DMSO-d$_6$, ppm): δ 237.52, 235.49, 158.25, 145.81, 132.69, 131.51, 131.35, 131.07, 130.76, 129.48, 129.31, 127.65, 126.94, 125.32, 124.37, 91.91, 65.55, 32.94, 31.27, 28.41, 25.58, 22.38, 14.24. HRMS (ESI) calcd for C$_{24}$H$_{26}$N$_3$O$_2$SCl [M+H]$^+$ 456.1434, found 456.1410. HPLC purity: 97.55%, Retention time=13.12 min.

(E)-4-(2-chlorophenyl)-2-[1-methyl-2-(2-cyclohexy-loxyformylbenzylidene)hydrazino]thiazole B8

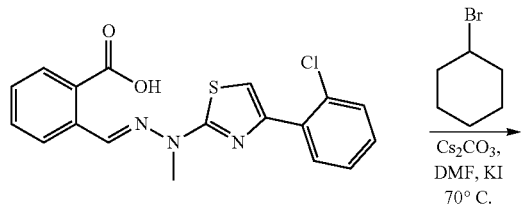

130 mg of pale yellow powder (yield 53%) was obtained according to the same synthesis method as that for B1. Mp: 134-136° C. $^1$H NMR (100 MHz, DMSO-d$_6$, ppm): δ 8.50 (s, 1H), 8.02 (d, J=8.0, 1.3 Hz, 1H), 7.96 (dd, J=7.7, 1.8 Hz, 1H), 7.90 (dd, J=7.9, 1.4 Hz, 1H), 7.72-7.66 (m, 1H), 7.56-7.47 (m, 3H), 7.43 (td, J=7.5, 1.5 Hz, 1H), 7.37 (td, J=7.6, 1.9 Hz, 1H), 5.03-4.95 (m, 1H), 3.69 (s, 3H), 1.98-1.90 (m, 2H), 1.79-1.65 (m, 2H), 1.61-1.49 (m, 3H), 1.47-1.29 (m, 3H). $^{13}$C NMR (100 MHz, DMSO-d$_6$, ppm): δ 169.02, 166.44, 147.22, 136.65, 135.03, 133.50, 132.81, 131.62, 131.20, 130.87, 129.89, 129.61, 129.43, 127.77, 126.82, 111.62, 73.78, 33.06, 31.51, 25.32, 23.69. HRMS (ESI) calcd for C$_{24}$H$_{24}$N$_3$O$_2$SCl [M+H]$^+$ 454.1278, found 454.1294. HPLC purity: 97.32%, Retention time=11.53 min.

(E)-4-(2-chlorophenyl)-2-[1-methyl-2-(2-pheny-lethoxyformylbenzylidene)hydrazino]thiazole B9

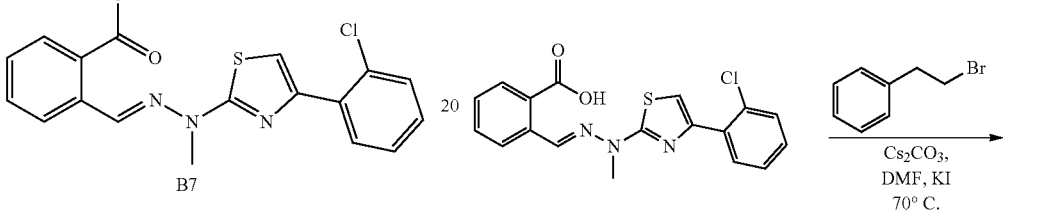

100 mg of yellow powder (yield 46%) was obtained according to the same synthesis method as that for B1, except that an equimolar amount of potassium iodide was added. Mp: 125-126° C. $^1$H NMR (400 MHz, DMSO-d$_6$, ppm): δ 8.40 (s, 1H), 8.02-7.93 (m, 2H), 7.84-7.80 (m, 1H), 7.71-7.66 (m, 1H), 7.56-7.47 (m, 3H), 7.43 (td, J=7.5, 1.5 Hz, 1H), 7.37 (td, J=7.6, 1.9 Hz, 1H), 7.31 (d, J=4.3 Hz, 4H), 7.26-7.19 (m, 1H), 4.54 (t, J=6.7 Hz, 2H), 3.61 (s, 3H), 3.06 (t, J=6.7 Hz, 2H). $^{13}$C NMR (100 MHz, DMSO-d$_6$, ppm): δ 168.88, 166.89, 147.13, 138.34, 136.45, 135.03, 133.42, 132.77, 131.52, 131.10, 130.76, 130.60, 129.49, 129.24, 128.77, 127.65, 126.90, 126.80, 111.49, 65.95, 34.67, 32.92. HRMS (ESI) calcd for C$_{26}$H$_{22}$N$_3$O$_2$SCl [M+H]$^+$ 476.1121, found 476.1201. HPLC purity: 99.01%, Retention time=9.75 min.

(pivaloyloxy)methyl

(E)-2-((2-(4-(2-chlorophenyl)thiazol-2-yl)-2-methyl-hydrazono)methyl)benzoate B10

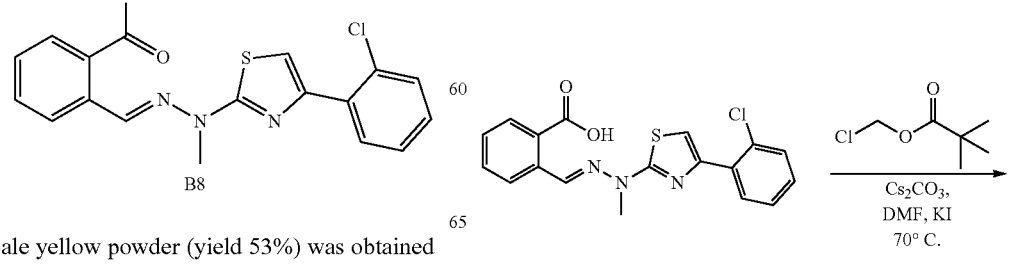

-continued

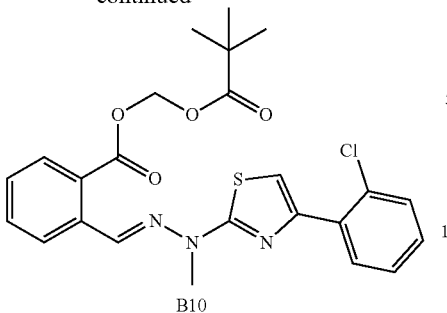

B10

120 mg of bright yellow powder (yield 57%) was obtained according to the same synthesis method as that for B9. Mp: 126-127° C. $^1$H NMR (400 MHz, DMSO-$d_6$, ppm): δ 8.44 (s, 1H), 8.03 (d, J=8.0, 1.2 Hz, 1H), 7.96 (dd, J=7.7, 1.9 Hz, 1H), 7.89-7.85 (m, 1H), 7.77-7.71 (m, 1H), 7.57-7.53 (m, 2H), 7.49 (s, 1H), 7.43 (td, J=7.5, 1.4 Hz, 1H), 7.37 (td, J=7.6, 1.9 Hz, 1H), 5.99 (s, 2H), 3.69 (s, 3H), 1.17 (s, 9H). $^{13}$C NMR (100 MHz, DMSO-$d_6$, ppm): δ 176.91, 168.94, 165.74, 147.24, 136.17, 135.56, 133.60, 133.48, 131.64, 131.20, 130.97, 130.87, 129.62, 129.56, 128.04, 127.77, 127.18, 111.73, 89.14, 80.79, 33.07, 26.96. HRMS (ESI) calcd for $C_{24}H_{24}N_3O_4SCl$ [M+H]$^+$ 486.1176, found 486.1256. HPLC purity: 97.64%, Retention time=13.15 min.

((isopropoxycarbonyl)oxy)methyl (E)-2-((2-(4-(2-chlorophenyl)thiazol-2-yl)-2-methyl-hydrazono)methyl)benzoate B11

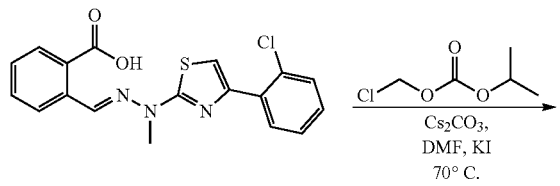

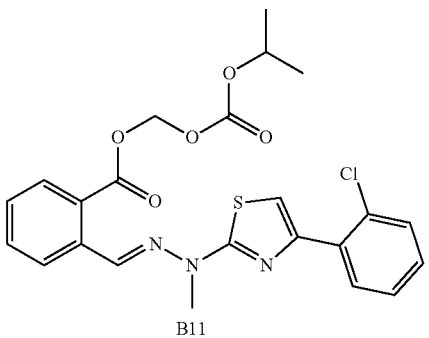

B11

90 mg of firefly yellow powder (yield 54%) was obtained according to the same synthesis method as that for B9. Mp: 122-123° C. $^1$H NMR (400 MHz, DMSO-$d_6$, ppm): δ 8.74 (s, 1H), 8.30 (d, J=8.0, 1.3 Hz, 1H), 8.15 (dd, J=8.0, 1.4 Hz, 1H), 8.09 (dd, J=7.8, 1.8 Hz, 1H), 7.74-7.67 (m, 1H), 7.54-7.47 (m, 2H), 7.44-7.36 (m, 2H), 7.36-7.28 (m, 2H), 6.10 (s, 2H), 5.07-5.00 (m, 1H), 3.86 (s, 3H), 1.42 (d, J=6.2 Hz, 6H). $^{13}$C NMR (100 MHz, DMSO-$d_6$, ppm): δ 169.03, 165.22, 153.36, 147.30, 136.67, 134.75, 133.43, 133.13, 131.72, 131.21, 131.12, 130.39, 128.36, 128.31, 126.86, 126.71, 126.38, 110.68, 82.11, 73.18, 32.67, 21.57. HRMS (ESI) calcd for $C_{23}H_{22}N_3O_5SCl$ [M+H]$^+$ 488.0969, found 488.1046. HPLC purity: 95.65%, Retention time=6.77 min.

(E)-4-(2-chlorophenyl)-2-[1-methyl-2-(2-(chloro-formylbenzylidene)hydrazino]thiazole 12b

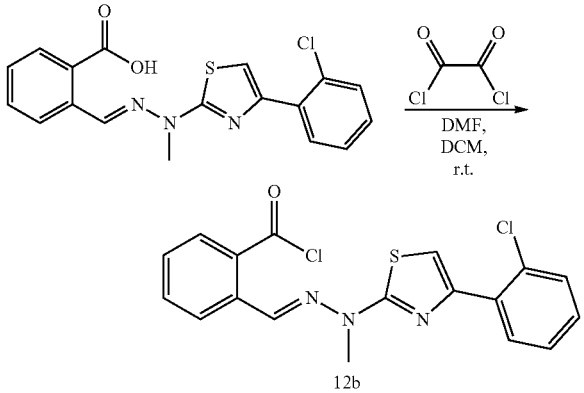

12b

Compound B (0.2 g, 0.54 mmol) was weighed into a 50 mL two-necked flask, and 10 mL of dichloromethane and 2 drops of N,N-dimethylformamide (DMF) were added, and stirred for 10 minutes in an ice bath. Oxalyl chloride (0.13 g, 1.08 mmol) was dissolved in 5 mL of dichloromethane and added dropwise to the reaction flask. The reaction mixture was placed in the ice bath for another half an hour, the ice bath was removed, the reaction mixture was warmed to room temperature for 2 h, and the reaction was detected: the reaction solution was taken into a tube, methanol was added with shaking, then water and ethyl acetate were added and allowed to stand, the upper organic phase was taken and detected by TLC to determine that the raw material point basically disappeared. The preparation of acid chloride was successful. The solvent of the reaction solution was evaporated to dryness in vacuo to give a yellow liquid, which was directly used in the next step.

(E)-4-(2-chlorophenyl)-2-[1-methyl-2-(2-((N,N-dimethyl)formylbenzylidene)hydrazino]thiazole B12

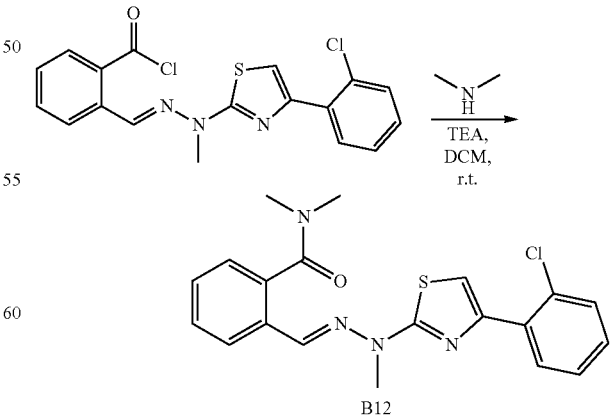

B12

Dimethylamine (24 mg, 0.54 mmol), triethylamine (55 mg, 0.54 mmol) and 10 mL of anhydrous dichloromethane were added into a 50 mL single-mouth reaction flask and electromagnetic-stirred for 15 minutes in an ice bath. The freshly prepared acid chloride solution in dichloromethane was added dropwise to the reaction flask, and maintained in an ice bath for 30 minutes. The reaction was warmed to room temperature for 10 hours, and detected by TLC. After the reaction was completed, 5 ml of water and 5 ml of dichloromethane were added into the reaction mixture, and stirred for 10 minutes. The mixture was allowed to stand for stratification. The organic phase was taken, the aqueous phase was extracted for three times with dichloromethane, and organic phases were combined and dried. The solvent was evaporated to dryness in vacuo and purified through column chromatography to give 50 mg of off-white solid powder (yield 25%). Mp: 160-161° C. $^1$H NMR (400 MHz, DMSO-d$_6$, ppm): δ 7.96 (dd, J=8.0, 2 Hz, 1H), 7.87 (d, J=7.6 Hz, 1H), 7.73 (s, 1H), 7.55-7.29 (m, 7H), 3.65 (s, 3H), 3.07 (s, 3H), 2.80 (s, 3H). $^{13}$C NMR (100 MHz, DMSO-d$_6$, ppm): δ 169.57, 168.91, 147.14, 136.30, 135.65, 133.52, 131.62, 131.34, 131.19, 130.86, 129.58, 129.46, 127.76, 127.59, 127.22, 111.59, 38.62, 34.90, 32.95. HRMS (ESI) calcd for $C_{20}H_{19}N_4OSCl$ $[M+H]^+$ 399.0968, found 399.1048. HPLC purity: 99.75%, Retention time=4.61 min.

Example 2

Culture and Purification of hsDHODH Protein

Culture of protein: hsDHODH protein was obtained according to hsDHODH gene sequence in GenBank and the conditions described in a conventional method, for example, Sambrook et al., Molecular Cloning: A Laboratory Guide (New York: Cold Spring Harbor Laboratory Press, 1989).

The correctly sequenced recombinant plasmid pET-19b-DHODH was transformed into competent E. coli BL21 (DE3), and cultured on LB plate containing ampicillin. Colonies were randomly selected, inoculated into LB medium containing 100 μM ampicillin, and incubate overnight at 37° C., 230 rpm. The cells were inoculated at a ratio of 1:200 in 500 mL of LB medium containing 100 μL of ampicillin and expanded at 37° C., 230 rpm. When the OD value of the cells reached 0.8-1, IPTG was added into the medium to a final concentration of IPDG of 0.5 mM, and expression was induced overnight at 25° C. The induced cells were collected by centrifugation at 4000° C., 4° C., washed with deionized water, and centrifuged again to collect the bacterial pellet, which was stored at −80° C.

Purification of protein: cells were re-suspended in lysis liquid containing 50 mM HEPES (pH 8.0), 0.15 M NaCl, 10 mM imidazole, 10% glycerol, 0.1% Triton X-100, and a small amount of soy protease inhibitor added. After re-suspended and mixed homogeneously, cells were ultrasonically disrupted. The disruption solution was centrifuged for 30 min, and the supernatant and precipitate were taken for protein electrophoresis to determine the form of protein. The supernatant was loaded onto a Ni-NTA column, and the pass-through liquid was collected, and then the resin was washed for 3-4 times with a lysis liquid containing 20 mM imidazole, and finally eluted with a lysis liquid containing 300 mM imidazole. After elution, protein solution was collected. 10 μL of the above protein sample was taken for SDS-PAGE electrophoresis to determine the content of target protein. Finally, the eluted protein solution is dialyzed in the dialysis liquid to remove imidazole, thereby obtaining a pure protein.

Method for Testing Activities of Compounds at Enzyme Level

Principles of activity test at enzyme level: firstly, dihydroorotate (DHO) is oxidatively dehydrogenated by DHODH to form orotic acid (Orotate, OA), accompanied by reduction of Flavin mononucleotide (FMN) into reduced flavin mononucleotide (FMNH$_2$) by accepting 2H+ and 2e−, then coenzyme Q (CoQ) as hydrogen acceptor accepting electron and proton from FMNH$_2$ is reduced into reduced coenzyme Q (CoQH$_2$), reduced coenzyme Q transfers electrons to a chromogenic substrate, diclofenac sodium salt (DCIP), and finally DCIP was reduced. DCIP shows maximum absorption at 600 nm, while the reduced DCIP does not show absorption at 600 nm. The degree to which the substrate DHO is oxidized can be judged based on the degree of decrease in absorbance. The degree of oxidation of the substrate DHO per unit time is the initial rate of the enzymatic reaction. Upon addition of a inhibitor, the initial rate of the enzymatic reaction is reduced.

The purified DHODH was diluted to 10 nM with a test buffer (50 mM HEPES, pH 8.0, 150 mM KCl, 0.1% Triton X-100), and coenzyme Q and DCIP were added to a final concentration of 100 μM and 120 μM, respectively, mixed well, added into a 96-well plate and incubated for 5 min at room temperature. Substrate DHO was added to start the reaction with a DHO final concentration of 500 μM. The absorbance was read at 600 nm using a BioTek microplate reader and read every 30 s for 6 min. For inhibitor activity test, different concentrations of inhibitors were added into the above reaction system, the initial rate of enzymatic reaction when no inhibitor was added was $V_0$, and the initial rate of enzymatic reaction after an inhibitor was added was $V_i$, and the inhibition rate of a compound was calculated by the formula $(1-V_i/V_0) \times 100\%$. For calculating $IC_{50}$ of a compound, Origin 8.0 was used to test the inhibition rate at least 8 concentrations. In the experimental procedure, Brequinar (purchased from Sigma-Aldrich Reagent) was used as a positive control and at least three parallels were set in each experiment. The results are shown as follows:

| No. of Compound | $IC_{50}$ (μM) hsDHODH |
|---|---|
| 1 | 0.0097 ± 0.0001 |
| 2 | 0.0587 ± 0.0016 |
| 3 | 0.0086 ± 0.0001 |
| 4 | 0.0931 ± 0.0011 |
| 5 | 0.0244 ± 0.0002 |
| 6 | 0.0191 ± 0.0006 |
| 7 | 0.4253 ± 0.0092 |
| 8 | 0.0868 ± 0.0009 |
| 9 | 0.0084 ± 0.0001 |
| 10 | 0.0018 ± 0.0001 |
| 11 | 0.0136 ± 0.0005 |
| 12 | 0.0088 ± 0.0001 |
| 13 | 0.0355 ± 0.0009 |
| 14 | 0.3557 ± 0.0064 |
| 15 | 0.0662 ± 0.0002 |
| 17 | 0.0811 ± 0.0001 |
| 19 | 0.0282 ± 0.0000 |
| 20 | 0.0244 ± 0.0005 |
| 21 | 0.0106 ± 0.0000 |
| 22 | 0.0154 ± 0.0002 |
| 23 | 0.0044 ± 0.0000 |
| 24 | 0.0214 ± 0.0005 |
| 25 | 0.0316 ± 0.0001 |
| 58 | 0.2342 ± 0.0068 |
| Brequinar | 0.00845 ± 0.00005 |

Similarly, test results of pharmaceutically acceptable esters of a compound of the invention are shown in the following table:
| No. 2 | Structure | Molecular weight | IC$_{50}$ (μM) |
|---|---|---|---|
| A1 | 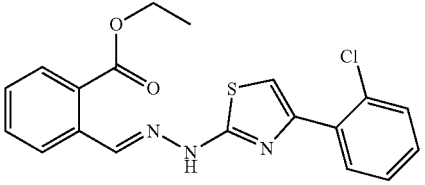 [SMILES: CCOC(=O)c1ccccc1/C=N/Nc1nc(-c2ccccc2Cl)cs1] | 385.87 | 2.33622 ± 0.04680 |
| A2 | 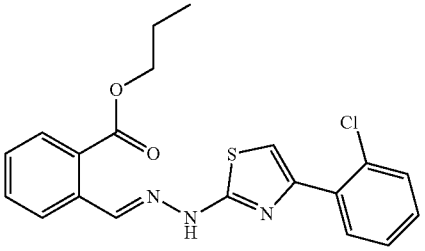 [SMILES: CCCOC(=O)c1ccccc1/C=N/Nc1nc(-c2ccccc2Cl)cs1] | 399.08 | 1.40452 ± 0.06606 |
| A3 | 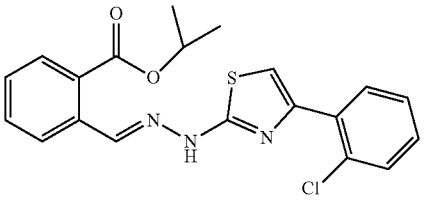 | 399.08 | 1.85794 ± 0.02135 |
| A4 | 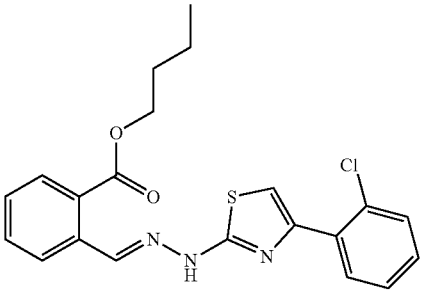 [SMILES: CCCCOC(=O)c1ccccc1/C=N/Nc1nc(-c2ccccc2Cl)cs1] | 413.10 | 3.53302 ± 0.14798 |
| A5 | 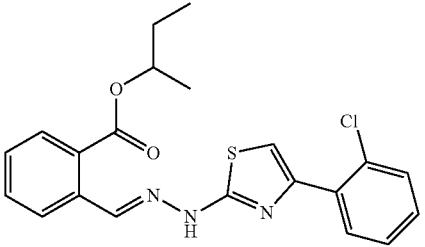 [SMILES: CCC(C)OC(=O)c1ccccc1/C=N/Nc1nc(-c2ccccc2Cl)cs1] | 413.10 | 4.65095 ± 0.02643 |

-continued
| No. 2 | Structure | Molecular weight | IC$_{50}$ (μM) |
|---|---|---|---|
| A6 | 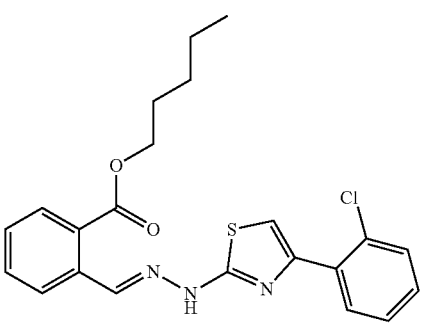 [SMILES: CCCCCOC(=O)c1ccccc1/C=N/Nc1nc(-c2ccccc2Cl)cs1] | 427.11 | >50 |
| A7 | 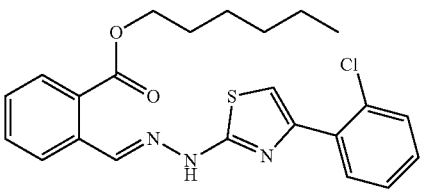 [SMILES: CCCCCCOC(=O)c1ccccc1/C=N/Nc1nc(-c2ccccc2Cl)cs1] | 441.13 | >50 |
| A8 | 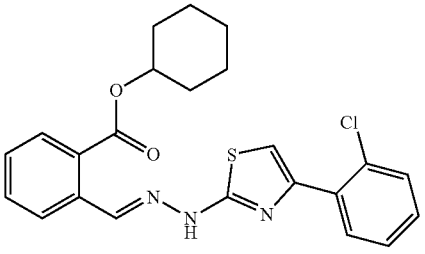 [SMILES: O=C(OC1CCCCC1)c1ccccc1/C=N/Nc1nc(-c2ccccc2Cl)cs1] | 439.11 | >50 |
| A9 | 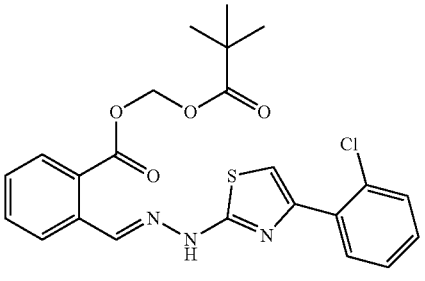 [SMILES: CC(C)(C)C(=O)OCOC(=O)c1ccccc1/C=N/Nc1nc(-c2ccccc2Cl)cs1] | 471.10 | >50 |
| A10 | 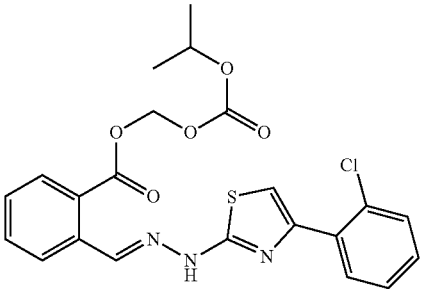 [SMILES: CC(C)OC(=O)OCOC(=O)c1ccccc1/C=N/Nc1nc(-c2ccccc2Cl)cs1] | 473.08 | >50 |

-continued

| No. 2 | Structure | Molecular weight | IC$_{50}$ (μM) |
|---|---|---|---|
| A11 | 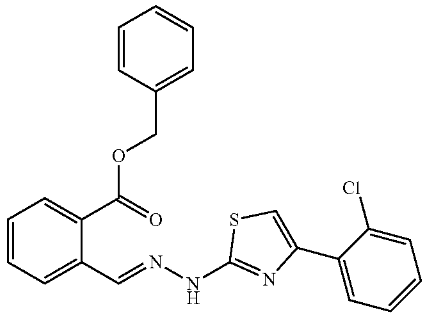 [SMILES: O=C(OCc1ccccc1)c1ccccc1/C=N/Nc1nc(-c2ccccc2Cl)cs1] | 447.08 | >50 |
| A12 | 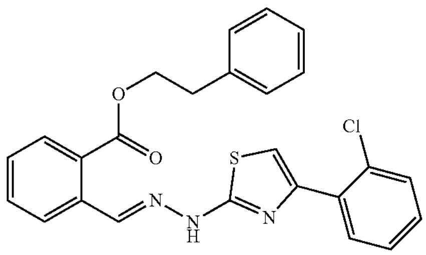 [SMILES: O=C(OCCc1ccccc1)c1ccccc1/C=N/Nc1nc(-c2ccccc2Cl)cs1] | 461.10 | >50 |
| A13 | 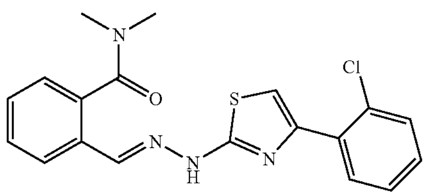 [SMILES: CN(C)C(=O)c1ccccc1/C=N/Nc1nc(-c2ccccc2Cl)cs1] | 384.08 | >50 |
| B1 | 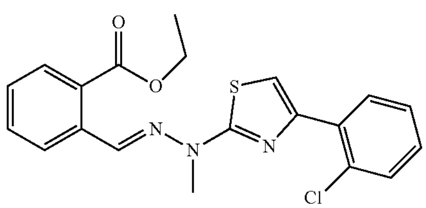 [SMILES: CCOC(=O)c1ccccc1/C=N/N(C)c1nc(-c2ccccc2Cl)cs1] | 399.08 | 2.78515 ± 0.04653 |
| B2 | 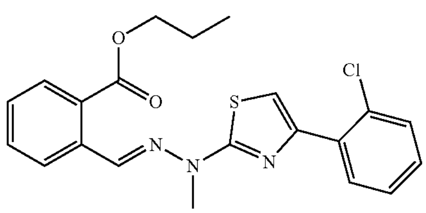 [SMILES: CCCOC(=O)c1ccccc1/C=N/N(C)c1nc(-c2ccccc2Cl)cs1] | 413.10 | 1.95561 ± 0.11059 |
| B3 | 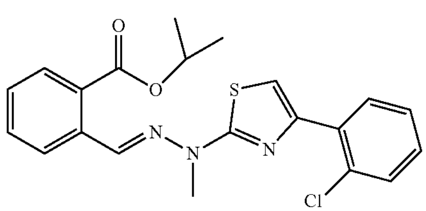 [SMILES: CC(C)OC(=O)c1ccccc1/C=N/N(C)c1nc(-c2ccccc2Cl)cs1] | 413.10 | 3.3655 ± 0.15427 |

-continued

| No. 2 | Structure | Molecular weight | IC$_{50}$ (μM) |
|---|---|---|---|
| B4 | 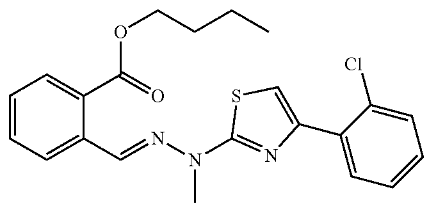 [SMILES: CCCCOC(=O)c1ccccc1/C=N/N(C)c1nc(-c2ccccc2Cl)cs1] | 427.11 | >50 |
| B5 | 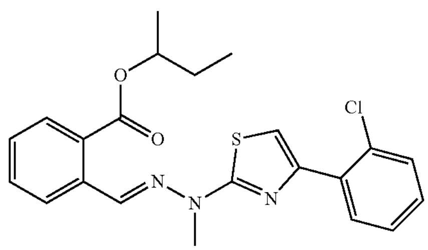 [SMILES: CCC(C)OC(=O)c1ccccc1/C=N/N(C)c1nc(-c2ccccc2Cl)cs1] | 427.11 | >50 |
| B6 | 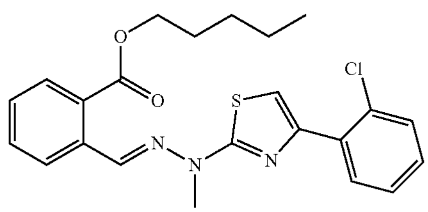 [SMILES: CCCCCOC(=O)c1ccccc1/C=N/N(C)c1nc(-c2ccccc2Cl)cs1] | 441.13 | >50 |
| B7 | 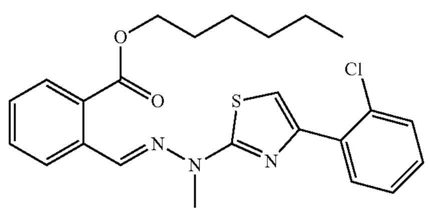 [SMILES: CCCCCCOC(=O)c1ccccc1/C=N/N(C)c1nc(-c2ccccc2Cl)cs1] | 455.14 | >50 |
| B8 | 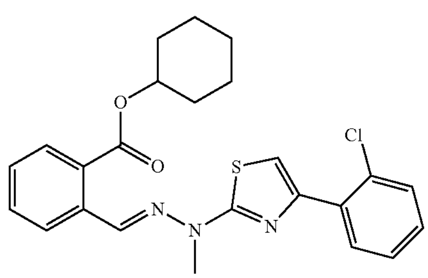 [SMILES: CN(/N=C/c1ccccc1C(=O)OC1CCCCC1)c1nc(-c2ccccc2Cl)cs1] | 453.13 | >50 |
| B9 | 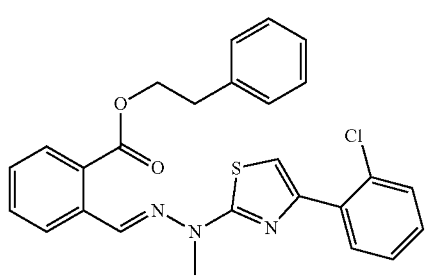 [SMILES: CN(/N=C/c1ccccc1C(=O)OCCc1ccccc1)c1nc(-c2ccccc2Cl)cs1] | 475.11 | >50 |

-continued

| No. 2 | Structure | Molecular weight | IC$_{50}$ (μM) |
|---|---|---|---|
| B10 | 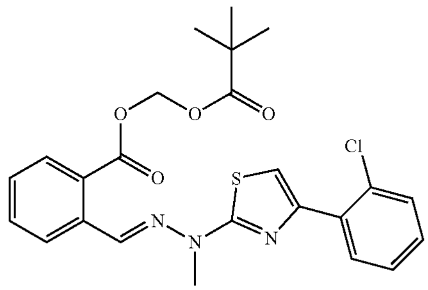 [SMILES: CN(/N=C/c1ccccc1C(=O)OCOC(=O)C(C)(C)C)c1nc(-c2ccccc2Cl)cs1] | 485.12 | >50 |
| B11 | 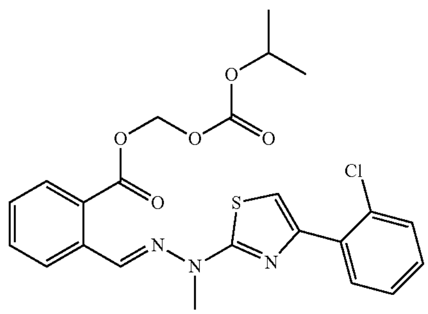 [SMILES: CC(C)OC(=O)OCOC(=O)c1ccccc1/C=N/N(C)c1nc(-c2ccccc2Cl)cs1] | 487.10 | >50 |
| B12 | 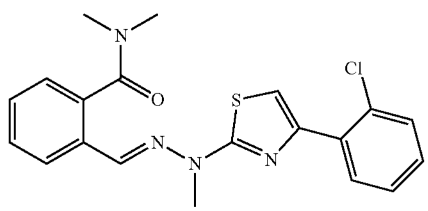 [SMILES: CN(C)C(=O)c1ccccc1/C=N/N(C)c1nc(-c2ccccc2Cl)cs1] | 398.10 | >50 |

Discussion:

From the results of the activity assay of the compound of the present invention carried out at the enzyme level, it is understood that the compounds of the present invention have excellent DHODH inhibitory activity, and IC$_{50}$ values for some compounds for inhibiting DHODH can even reach 1-10 nM.

Therefore, the compound of the present invention shows a prospect of becoming a novel DHODH inhibitor with low toxicity and high safety.

Example 3

Pharmacodynamic Evaluation of Compound 1 on Rheumatoid Arthritis Model 1.1 Division of Animals

TABLE A-1

Wistar rat division for compound 1

| Group No. | Group | Number of rat | Administration and dosage | Administration mode |
|---|---|---|---|---|
| 1 | Normal Control group | 6 | Solvent system | Intraperitoneal injection |
| 2 | Model group | 11 | Solvent system | Intraperitoneal injection |
| 3 | Low dosage group | 11 | 5 mg/kg compound 1 | Intraperitoneal injection |
| 4 | High dosage group | 11 | 30 mg/kg compound 1 | Intraperitoneal injection |
| 5 | Positive drug control group | 10 | 0.3 mg/kg Methotrexate | Intraperitoneal injection |

1.2 Solution Preparation

The animal model used in this experiment was a type II collagen-induced arthritis animal model (CIA) established by using Wistar rat. On the 0 and 7th day of the experiment, rats were subcutaneously injected with a mixed solution of Bovine II Collagen (CII) and Incomplete Freund's Adjuvant (IFA) to establish a rat model of arthritis.

In the pharmacodynamic test of Compound 1, Compound 1 and the positive drug, methotrexate were dissolved in a solvent system consisting of dimethyl sulfoxide (DMSO), polyethylene glycol 400 (PEG 400) and physiological saline at a volume ratio of 1:10:9.

1.3 the Schedule is Shown in FIG. 1

1.4 Experiment Results

1.4.1 Arthritis Assessment Index

During the administration to the rats (day 0 to 27 of the experiment), the body weight of a rat was weighed every three days, and the growth was observed. After the joints of the rat began to swell, the degree of joint swelling was scored every two days. The specific scoring criteria are shown in Table B.

TABLE B

Score standard for joint swelling of rat

| Score | Symptom |
|---|---|
| 0分 | No redness |
| 1 | redness and swelling in small toe joint |
| 2 | Swelling in toe joint and ankle |
| 3 | Swelling in the part below the ankle joint |
| 4 | Swelling in ankle joint and below part |

Because the incidence of inflammation in fore paw is low and the hind paws are more prone to swelling and the degree of swelling is more serious, the sum of the scores of two hind paws is used to evaluate the incidence of arthritis in rats. The maximum sum of score is 8 points.

1.4.2 Effects of Compound 1 on Body Weight and Joint Swelling of CIA Rats

In this experiment, Wistar rats were used to establish a CIA animal model. Joints were taken on the 28th day for subsequent fixation, paraffin embedding, section, staining and histopathological observation. The experiment results are shown as follows: During the experiment, the weight of rats in the control group continued to increase.

Compared with the model group, the weight gain of the rats in the model group was slightly slower. Administration of Compound 1 and methotrexate can improve the condition of the rats and the slow gain of body weight (FIG. 2A).

On the 10th day of the experiment, i.e., the third day after booster immunization, the rats in the model group began to develop gradually. On the 18th day of the experiment, the joint swelling of the rats in the model group was the most serious, and afterwards the situation became stable. The administration of positive drug methotrexate (0.3 mg/kg) can significantly reduce the degree of joint swelling in rats, and in the rats given compound 1 (5 mg/kg, 30 mg/kg), compared with the model group, the degree of joint swelling was also significantly reduced. Especially, when a higher dosage (30 mg/kg) was given, the swelling was more significantly reduced. On the 28th day, scores of joint swelling in the high-dose group and positive drug group were similar (FIG. 2B).

Figure 2:
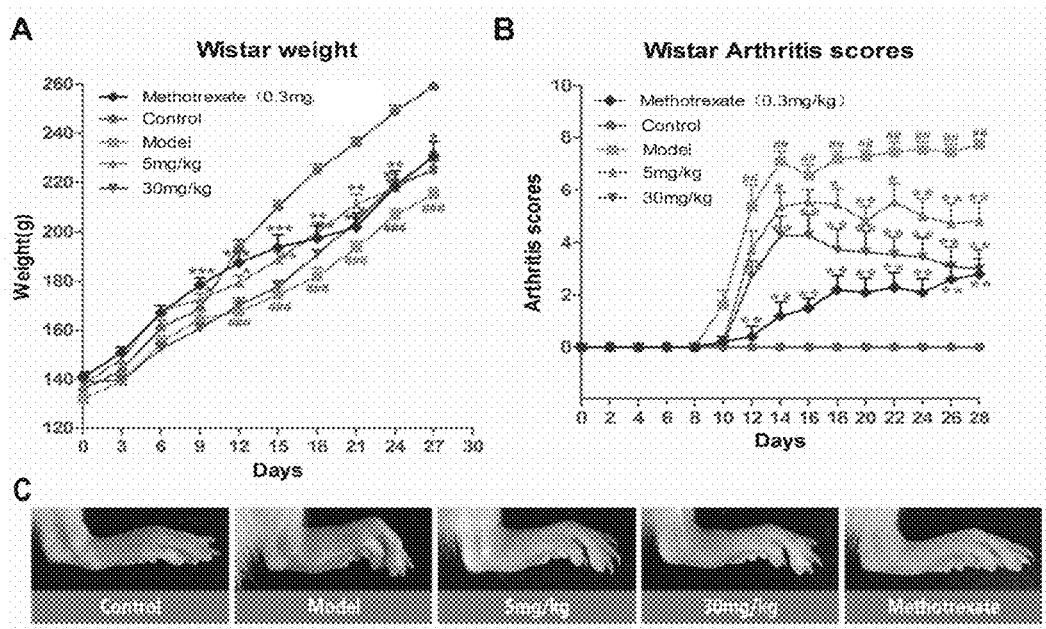
FIG. 2 shows effects of Compound 1 on body weight and joint swelling of CIA model rats. Among them, Figure A shows the trend of change in the body weight of rats (weighed once every three days). Figure B shows the trend of change in the score of rat joint swelling (scored every two days). Figure C shows representative photographs of rat foot from different experiment groups. The data are expressed as mean±SEM, ##$P<0.01$, compared with the control; * $P<0.05$, ** $P<0.01$, compared with the model.

FIG. 2C shows representative photographs for the foot of rats in each of the different treatment groups on day 28 of the experiment. It can be seen from FIG. 2C that the foot swelling of rats in the model group is the most serious, and the swelling degree of the foot, after the administration of the positive drug and two different concentrations of compound 1, was improved, and the effects of high dose of compound 1 is more significant than those of low dose.

The above results of weight gain and joint swelling scores indicate that Compound 1 may have a strong effect on improving joint swelling in CIA animal model.

1.4.3 Effects of Compound 1 on Histopathology of CIA Rats

Figure 3:
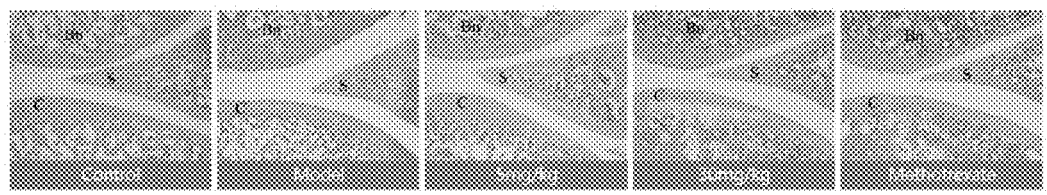
FIG. 3 is a representative photograph of HE staining of joint tissue sections, and shows effects of Compound 1 on the histopathology of CIA model rats; wherein S means synovial membrane; C means cartilage; Bn means bone; and magnification is 40×.

Results of effects of Compound 1 on histopathology of arthritic rats are shown in FIG. 3. There was a significant inflammatory cell infiltration in the joint tissues of the model group, accompanied by severe cartilage damage and bone erosion. In the rats treated with Compound 1, the histopathological features were significantly alleviated, and in the higher dose group, improvement was more significant, indicating that Compound 1 may have a significant anti-arthritic effect, and the effect has a dose-dependent relationship.

1.5 Conclusion

In the experiment, an animal model of type II collagen-induced arthritis was established using Wistar rats, and therapeutic effects of DHODH inhibitor, Compound 1 on arthritis were tested. Results showed that after the arthritis model was established and treated with Compound 1, the weight loss caused by the establishment of the model can be improved and the swelling of the joints in rats can be reduced.

In addition, the results of tissue sections also showed that the synovial hyperplasia and inflammatory cell infiltration in rats treated with Compound 1 were greatly improved compared with the model group.

The above results indicate that Compound 1 has anti-inflammatory effects and is a potential compound for RA treatment with a dose-dependent relationship.

All documents mentioned in the present application are hereby incorporated by reference in their entireties as if each document is separately cited as a reference. In addition, it is to be understood that various modifications and changes may be made by a skilled person in the art, after reading the above teachings of the present invention, and the equivalent forms also fall within the scope defined by the claims appended hereto.

The invention claimed is:

1. A compound or a pharmaceutically acceptable salt or ester thereof, wherein the compound is selected from the following group:

| No. | Structure |
|---|---|
| 1 | (structure with COOH, thiazole, Cl-phenyl) |
| 3 | (structure with COOH, thiazole, Cl-phenyl) |
| 8-1 | (structure with $F_3C$, COOH, thiazole, Cl-phenyl) |

| No. | Structure |
|---|---|
| 9 | 5-methyl-2-[(E)-{[methyl-(4-(2-chlorophenyl)thiazol-2-yl)amino]imino}methyl]benzoic acid |
| 9-1 | 5-methyl-2-[(E)-{[(4-(2-chlorophenyl)thiazol-2-yl)amino]imino}methyl]benzoic acid |
| 10 | 5-fluoro-2-[(E)-{[methyl-(4-(2-chlorophenyl)thiazol-2-yl)amino]imino}methyl]benzoic acid |
| 10-1 | 5-fluoro-2-[(E)-{[(4-(2-chlorophenyl)thiazol-2-yl)amino]imino}methyl]benzoic acid |
| 11 | 5-methyl-2-[(E)-{[methyl-(5-methyl-4-phenylthiazol-2-yl)amino]imino}methyl]benzoic acid |
| 12 | 2-[(E)-{[methyl-(5-methyl-4-phenylthiazol-2-yl)amino]imino}methyl]benzoic acid |
| 12-1 | 2-[(E)-{[(5-methyl-4-phenylthiazol-2-yl)amino]imino}methyl]benzoic acid |
| 21 | 2-[(E)-{[methyl-(4-(3-chlorophenyl)thiazol-2-yl)amino]imino}methyl]benzoic acid |
| 22 | 2-[(E)-{[(pentan-2-yl)-(5-methyl-4-(2-chlorophenyl)thiazol-2-yl)amino]imino}methyl]benzoic acid |

| No. | Structure |
|---|---|
| 23 | 4,5-difluoro-2-[(E)-{[methyl-(4-(2-chlorophenyl)thiazol-2-yl)amino]imino}methyl]benzoic acid |
| 23-1 | 4,5-difluoro-2-[(E)-{[(4-(2-chlorophenyl)thiazol-2-yl)amino]imino}methyl]benzoic acid |
| A1 | ethyl 2-[(E)-{[(4-(2-chlorophenyl)thiazol-2-yl)amino]imino}methyl]benzoate |
| A2 | propyl 2-[(E)-{[(4-(2-chlorophenyl)thiazol-2-yl)amino]imino}methyl]benzoate |
| A3 | isopropyl 2-[(E)-{[(4-(2-chlorophenyl)thiazol-2-yl)amino]imino}methyl]benzoate |
| A4 | butyl 2-[(E)-{[(4-(2-chlorophenyl)thiazol-2-yl)amino]imino}methyl]benzoate |
| A5 | sec-butyl 2-[(E)-{[(4-(2-chlorophenyl)thiazol-2-yl)amino]imino}methyl]benzoate |

| No. | Structure |
|---|---|
| A6 | |
| A7 | |
| A8 | |
| A9 | |
| A10 | |
| A11 | 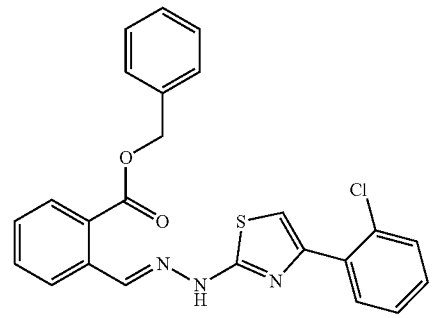 [SMILES: O=C(OCc1ccccc1)c1ccccc1/C=N/Nc1nc(-c2ccccc2Cl)cs1] |
| A12 | 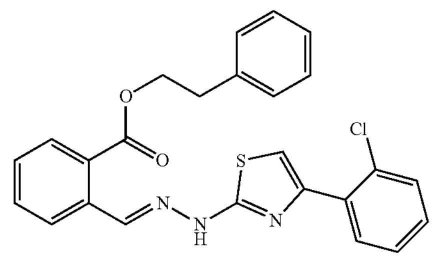 [SMILES: O=C(OCCc1ccccc1)c1ccccc1/C=N/Nc1nc(-c2ccccc2Cl)cs1] |
| A13 | 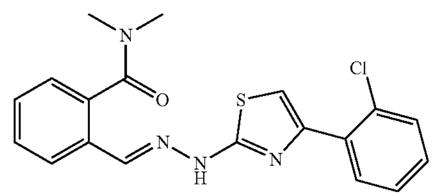 [SMILES: CN(C)C(=O)c1ccccc1/C=N/Nc1nc(-c2ccccc2Cl)cs1] |
| B1 | 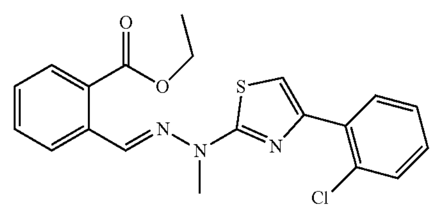 [SMILES: CCOC(=O)c1ccccc1/C=N/N(C)c1nc(-c2ccccc2Cl)cs1] |
| B2 | 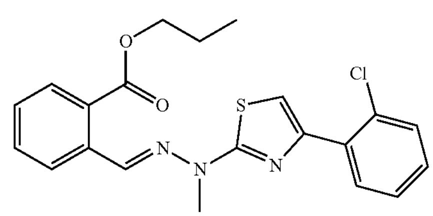 [SMILES: CCCOC(=O)c1ccccc1/C=N/N(C)c1nc(-c2ccccc2Cl)cs1] |
| B3 | 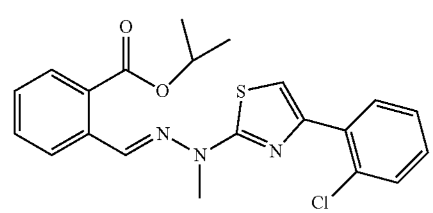 [SMILES: CC(C)OC(=O)c1ccccc1/C=N/N(C)c1nc(-c2ccccc2Cl)cs1] |

-continued

| No. | Structure |
|-----|-----------|
| B4 | 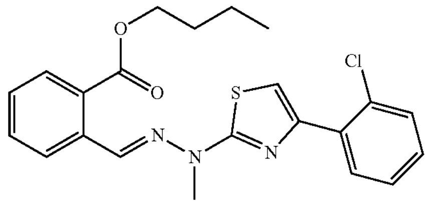 [SMILES: CCCCOC(=O)c1ccccc1/C=N/N(C)c1nc(-c2ccccc2Cl)cs1] |
| B5 | 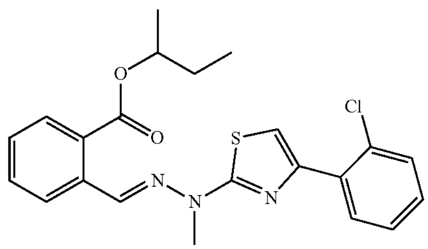 [SMILES: CCC(C)OC(=O)c1ccccc1/C=N/N(C)c1nc(-c2ccccc2Cl)cs1] |
| B6 | 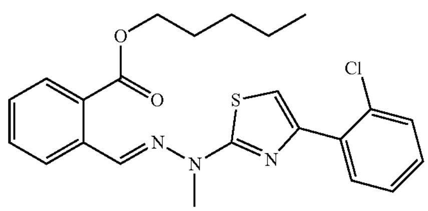 [SMILES: CCCCCOC(=O)c1ccccc1/C=N/N(C)c1nc(-c2ccccc2Cl)cs1] |
| B7 | 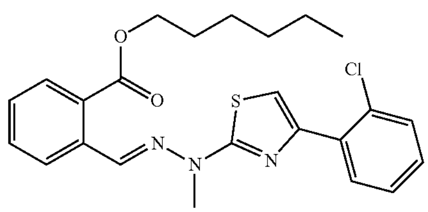 |
| B8 | 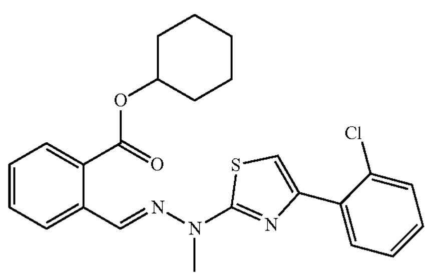 [SMILES: CN(/N=C/c1ccccc1C(=O)OC1CCCCC1)c1nc(-c2ccccc2Cl)cs1] |
| B9 | 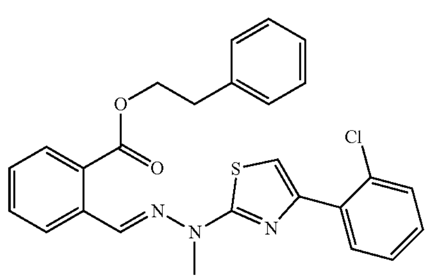 [SMILES: CN(/N=C/c1ccccc1C(=O)OCCc1ccccc1)c1nc(-c2ccccc2Cl)cs1] |

-continued

| No. | Structure |
|-----|-----------|
| B10 | 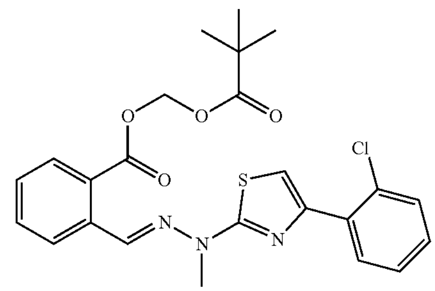 [SMILES: CN(/N=C/c1ccccc1C(=O)OCOC(=O)C(C)(C)C)c1nc(-c2ccccc2Cl)cs1] |
| B11 | and |
| B12 | . |

2. A pharmaceutical composition, comprising a compound of claim 1 or a pharmaceutically acceptable salt or ester thereof, and a pharmaceutically acceptable carrier or excipient.

3. A method for treating a DHODH-mediated disease, comprising administering the compound of claim 1 or a pharmaceutically acceptable salt or ester thereof, or the pharmaceutical composition of claim 2 to a subject in need thereof, wherein the DHODH-mediated disease is rheumatoid arthritis, organ transplant rejection, psoriasis, breast cancer, juvenile idiopathic arthritis, myeloma, polymyalgia rheumatic, systemic lupus erythematosus, or uveitis.

* * * * *